US012544502B2

(12) United States Patent
Batarilo et al.

(10) Patent No.: US 12,544,502 B2
(45) Date of Patent: Feb. 10, 2026

(54) MODULAR FLUID DELIVERY SYSTEM

(71) Applicant: ACIST MEDICAL SYSTEMS INC., Eden Prairie, MN (US)

(72) Inventors: Zvonimir Batarilo, Lausanne (CH); Dieter Heidmann, Geretsried (DE); Jan Sievertsen, Munich (DE)

(73) Assignee: ACIST MEDICAL SYSTEMS INC., Eden Prairie, MN (US)

( * ) Notice: Subject to any disclaimer, the term of this patent is extended or adjusted under 35 U.S.C. 154(b) by 875 days.

(21) Appl. No.: 17/787,766

(22) PCT Filed: Sep. 10, 2020

(86) PCT No.: PCT/EP2020/075316
§ 371 (c)(1),
(2) Date: Jun. 21, 2022

(87) PCT Pub. No.: WO2021/129960
PCT Pub. Date: Jul. 1, 2021

(65) Prior Publication Data

US 2023/0084243 A1 Mar. 16, 2023

(30) Foreign Application Priority Data

Dec. 23, 2019 (EP) .................................... 19219206

(51) Int. Cl.
*A61M 5/14* (2006.01)
*A61M 5/142* (2006.01)
*A61M 5/145* (2006.01)

(52) U.S. Cl.
CPC ...... *A61M 5/1413* (2013.01); *A61M 5/14216* (2013.01); *A61M 5/1452* (2013.01)

(58) Field of Classification Search
CPC ........ A61M 5/142; A61M 5/145; A61M 5/14; A61M 5/1413; A61M 5/14216;
(Continued)

(56) References Cited

U.S. PATENT DOCUMENTS 4,065,230 A 12/1977 Gezari
4,191,184 A * 3/1980 Carlisle ............ A61M 5/16809 222/61
(Continued)

FOREIGN PATENT DOCUMENTS

DE 102011120105 A1 6/2013
EP 1035882 B1 6/2004
(Continued)

OTHER PUBLICATIONS

International Search Report and Written Opinion for PCT/EP2020/075316, mailed Sep. 25, 2020.

*Primary Examiner* — Cris L. Rodriguez
(74) *Attorney, Agent, or Firm* — VIVICAR Law, PLLC

(57) ABSTRACT

A modular fluid delivery system is disclosed which comprises at least one supply station for supplying at least one fluid, and a pressurizing unit for pressurizing the at least one fluid, the pressurizing unit comprising at least one driving unit and at least one disposable pump module assembly. The disposable pump module assembly comprises at least one disposable pump module and a fluid circuit tubing. The disposable pump module comprises a supporting element which defines at least one chamber, at least one inlet fluid circuit pathway, at least one outlet fluid circuit pathway and at least one recirculation fluid circuit pathway. The fluid circuit tubing comprises at least one inlet fluid circuit tubing, at least one outlet fluid circuit tubing and at least one recirculation fluid circuit tubing.

9 Claims, 17 Drawing Sheets

(58) Field of Classification Search
CPC .............. A61M 5/1452; A61M 5/1422; A61M 2205/12; F04B 15/06; F04B 19/06; F04B 19/022
See application file for complete search history.

(56) References Cited

U.S. PATENT DOCUMENTS

| | | | | |
|---|---|---|---|---|
| 4,898,579 | A * | 2/1990 | Groshong | A61M 5/1422 604/152 |
| 5,411,374 | A | 5/1995 | Gram | |
| 5,551,488 | A | 9/1996 | Gram | |
| 5,787,940 | A * | 8/1998 | Bonn | F04B 19/06 141/2 |
| 6,135,719 | A | 10/2000 | Yoder et al. | |
| 7,566,320 | B2 * | 7/2009 | Duchon | A61M 5/14546 604/232 |
| 9,333,293 | B2 * | 5/2016 | Williams, Jr. | A61M 5/20 |
| 2007/0112297 | A1 * | 5/2007 | Plahey | A61M 1/155 604/28 |
| 2007/0196219 | A1 | 8/2007 | Hofling et al. | |
| 2012/0053557 | A1 * | 3/2012 | Abal | A61M 5/14216 604/151 |
| 2018/0266405 | A1 * | 9/2018 | Foege | F04B 39/06 |
| 2022/0409808 | A1 | 12/2022 | Batarilo et al. | |
| 2023/0011814 | A1 | 1/2023 | Batarilo et al. | |

FOREIGN PATENT DOCUMENTS

| | | | | |
|---|---|---|---|---|
| EP | 3669908 | A1 * | 6/2020 | A61M 1/362265 |
| WO | 9015632 | A1 | 12/1990 | |
| WO | 2008126035 | A1 | 10/2008 | |
| WO | 2015084302 | A1 | 6/2015 | |
| WO | 2016033351 | A2 | 3/2016 | |
| WO | 2017114706 | A1 | 7/2017 | |
| WO | WO-2019236972 | A1 * | 12/2019 | A61M 5/1408 |

* cited by examiner

MODULAR FLUID DELIVERY SYSTEM

CROSS-REFERENCE TO RELATED APPLICATIONS

This application is the national stage application of corresponding international application number PCT/EP2020/075316, filed Sep. 10, 2020, which claims priority to and the benefit of European application no. 19219206.0, filed Dec. 23, 2019.

TECHNICAL FIELD

The present disclosure relates to the field of fluid delivery. More specifically, the present disclosure relates to a modular fluid delivery system which allows delivery of at least one fluid under predetermined and desired operating conditions. Even more specifically, the present disclosure relates to a modular injection system for injecting at least one medical fluid and to methods of operating thereof.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Delivery systems for administering a liquid composition by injection or by infusion are known in the art.

In the medical field, for instance, a liquid medicament or a diagnostically active contrast agent is injected or infused into a patient's body, generally into a patient's blood vessel that reaches a body portion or a patient's body organ to be treated and/or analyzed (e.g. during scan examinations like X-ray, CT, MRI or ultrasound exams). In some specific applications, the liquid composition to be injected may comprise a suspension of microparticles homogeneously distributed in a liquid carrier, the homogeneity of which is requested to be preserved throughout the delivery thereof. Typically, the liquid composition comprises an aqueous suspension of gas filled microvesicles, namely microbubbles bounded by a surfactant stabilized gas/liquid interface, or microballoons bounded by a tangible material envelope.

Power injectors and mechanically assisted infusion systems for controllably dispensing therapeutically active medications or diagnostically active substances are well known in the art. Typically, such devices include an automatic injector with syringes containing an injectable liquid and a piston movable within the barrel of the syringe to expel said liquid through a tip thereof and then injecting it into a patient via a tubing connected to the syringe tip and to an injecting needle or catheter. For controlling the injections parameters, the piston is driven by means of an electromechanical arrangement that pushes the piston at a desired rate, continuously or at chosen intervals, so that the amount of medication is delivered to the patient's body under strictly determined conditions. For instance, in case of intravenous dispensing contrast agent formulations for diagnostic purposes (during X-ray, CT, MRI or ultrasound exams), the rate and the mode of injection can be accurately controlled to match the requirements of the imaging methods and detector systems used for investigating the circulation or a specific organ in the body.

It is important for the power injectors to control the homogeneity of the liquid composition stored within the syringe barrel during its administration, and this aspect becomes even more important when the injectable formulation is a suspension or dispersion of active particles which tend to settle, coalesce or segregate with time in the syringe. Indeed, even some modest separation of the particles by gravity or otherwise from the carrier liquid in the course of administration of the formulation may have very important influence on reproducibility and reliability of the injection results.

EP 1,035,882B1 and WO 2017/114706 disclose methods and means for keeping the syringe content homogeneous during injection. In details, these documents disclose methods of administering to patients by injection or by infusion a suspension of microparticles homogeneously distributed in a liquid carrier by means of an injector system comprising a syringe containing said suspension and a power-driven piston for injecting said suspension into a patient. According to these methods, the suspension contained in the syringe is subjected to a rotation or rocking motion, thereby maintaining the suspension homogeneous by preventing segregation of the microparticles by gravity or buoyancy, and without damaging said particles or disturbing their distribution.

WO 2016/033351 discloses an infusion system which comprises a double action infusion pump. The pump includes a cylinder and a reciprocating piston received within the cylinder, the reciprocating piston separating a first pump chamber from a second pump chamber of the cylinder. A reciprocating motor is coupled with the reciprocating piston, and the first and second pump chambers alternate between filling and evacuating conditions with reciprocation of the reciprocating piston through operation of the reciprocating motor, and the speed of reciprocation is varied to provide a continuous output of fluid between the first and second pump chambers. A fluid source and a catheter are optionally coupled with the double action infusion pump. The catheter includes one or more infusion ports near a catheter distal portion, and the one or more infusion ports receive and expel the continuous output of fluid from the double action infusion pump.

WO 1990/015632 discloses an infusion pump for administering fluid from a fluid source to a patient, said infusion pump comprising a base member having an electric motor for driving a fluid pump housed within a cassette detachably mountable on said base member. The cassette houses a reciprocate piston which pumps the fluid to the patient while simultaneously drawing fluid from the fluid source so as to maintain a continuous flow rate. The cassette houses deformable tubes connecting each of the pump's two fluid chambers to the cassette inlet and outlet to provide the necessary valving. The fluid flow rate is adjustably controlled by a microcomputer which regulates the motor by repeatedly initiating electric motor driving pulses at a predetermined time rate, and terminating them in response to the advancement of the motor beyond one of a plurality of predetermined positions so as to maximize accuracy of flow rate while maximizing the power efficiency.

DE 10 2011 120 105 discloses a device having a container with an opening, in which a movable piston is arranged. A piston rod is provided to displace the piston in the container. The container is divided into chambers. A flexible sealing element is provided to close the opening of the container. Two inlet ducts are communicated with a media feed line and the chambers respectively. Two outlet ducts are communicated with the media feed line and the chambers respectively.

With reference to the medical field, the injection of fluids into patients is commonplace in several medical procedures. For example, a contrast agent (or contrast medium) may be injected, possibly along with a saline solution, to enhance contrast of target (body) features (for example, human body's structures or organs) within the patients during scan examinations thereof. Particularly, in imaging applications (wherein a visual representation of the interior of the patients is created in a non-invasive way without turning to surgery techniques) the use of a contrast agent makes the target features more conspicuous. As a result, target features that would otherwise be less distinguishable from other nearby features (for example, surrounding tissues) are advantageously highlighted. This significantly facilitates the task of clinicians in diagnostic applications, and particularly in the identification and/or characterization of lesions, the monitoring of their evolution or the response to medical treatments. For example, iodine-based contrast agents (such as comprising iopamidol) are commonly used in Computed Tomography (CT) applications (such as angiography investigations).

The contrast agent is usually injected into a blood vessel of a patient by a preferably automated injection system. The injection system pressurizes the contrast agent and injects it into the patient's vasculature or organ under predetermined injection conditions, for example at a predetermined flow rate and volume. In this way, the contrast agent may be injected in a controlled, safe and efficient manner.

Therefore, an injection system is typically provided with one or more supply stations for supplying the contrast agent and/or the saline solution from a corresponding container (e.g. a bottle, a bag or a pouch). The injection system is further provided with a delivery arrangement (i.e. a combination of tubing lines) that is in fluid communication with the at least one supply station and a pressurizing unit. Since the delivery arrangement is positioned upstream of the pressurizing unit and, therefore, it is not in direct connection with a patient, with substantially no risk or a very low risk of cross-contamination, generally the delivery arrangement is a disposable element that is discarded periodically (for example, every 10 or 12 hours). This means that the delivery arrangement is not changed when a new patient undergoes an examination and it is typically kept in place for multiple successive injections (and thus multiple successive patients), till the predetermined period of time designed for that delivery arrangement is fully elapsed.

The powered injection systems known in the art and presently available on the market are categorized into two major groups: syringe injectors (like Empower CTA® or Empower CTA®+ manufactured by Bracco Injeneering SA) and syringe-less injectors (like CT Exprès® manufactured by Bracco Injeneering SA).

Syringe injectors can benefit from the syringe/piston technology which guarantees remarkably high-pressure fluid injection as well as fluid delivery accuracy and precision. Nevertheless, syringe injectors have some drawbacks which are mainly related to a cumbersome syringe workflow (in terms of loading and unloading of the syringes at the injector head, filling of the syringes with the fluid to be injected, priming and purging the syringes), to syringes (i.e. disposables) cost which is far from being negligible, and to troublesome waste management (i.e. inevitably discarding the expensive contrast agent that has not been injected to the patient and that has remained in the non-reusable syringes).

On the contrary, syringe-less injectors can benefit from a more efficient and lean workflow since the use of bottles/bags (in place of syringes) provides for higher quantities of contrast agent which is rendered available for serving multiple patients, thereby making waste management easier because only a disposable patient line is discarded every new incoming patient and contrast agent waste is remarkably reduced. Nevertheless, since the main technology used in the syringe-less injectors is a peristaltic pump—either as a disposable peristaltic pump or as a reusable peristaltic pump—due to its intrinsic nature, this technology does not allow to achieve significantly high pressures and flow rates (especially in the peristaltic pump disposable version) in comparison with the syringe injectors, and in operation it may also generate some disadvantageous fluctuations of the flow rate and/or of the pressure which, at some extent, may contribute in decreasing the delivery accuracy of the fluid delivery system.

Recently, some specific medical procedures have also required that the powered injectors can provide for high demanding hydraulic performances, in particular in terms of pressure and flow rate of the fluid to be injected into a patient.

For example, it has become more and more frequent that a powered injector is requested to be connected to implantable devices (e.g. PICC & PORT) which are already implanted in a patient's vasculature and which are used for establishing an intravascular access to a patient.

PICC is a Peripherally Inserted Central Catheter that is typically placed in a patient's arm to allow for a prolonged intravenous access, such as for extended antibiotic treatment or chemotherapy. A PICC is inserted in a peripheral vein (e.g. the cephalic vein, the basilic vein or the brachial vein) and then advanced through increasingly larger veins towards the heart, until the catheter tip rests in the distal superior vena cava or cave-atrial junction while the proximal end of the PICC remains outside of the body. A PICC is typically left in place in the patient's arm for periods ranging from six weeks to one year.

A PORT usually comprises a reservoir (the portal)—that is provided with a septum for needle insertion—and a catheter that goes from the reservoir into a patient's vein. The reservoir is surgically inserted under the skin in the upper chest or in the arm, and the catheter is fully inserted into the vein, i.e. there's no catheter tail outside of the patient's body.

Therefore, some patients that need to undergo an imaging examination (e.g. a computed tomography—CT) may already have a PICC & PORT in place for other purposes. Thus, already in place multi-lumen PICCs may be advantageously used by the healthcare personnel for power injection of diagnostic and/or therapeutic agents. However, the presence of said implanted devices inevitably represents a technical constraint for a powered injector (especially for a powered syringe-less injector) that is requested to generate pressure and flow rate values sufficiently high for still ensuring the desired and predetermined injection performances, even when said implanted devices are interposed between the injection system and the patient.

Technical fields different from medical applications may as well require delivery of compositions under specific and predetermined conditions.

For instance, a glue formulation may require to be delivered only when suitable operating conditions are guaranteed, e.g. when a given homogeneity of the glue formulation components is achieved. Therefore, a dedicated delivery system for applying the glue formulation in a given environment should ensure that the glue formulation is actually delivered only when said desired homogeneity is obtained, so that efficient and correct functioning of the glue can be obtained.

Ensuring a desired homogeneity is required, for instance, also in the processes for the preparation of a painting composition or of a coating composition that are carried out immediately before application thereof, particularly in the automotive, aerospace, housing fixtures industries.

According to further possible applications, a delivery system may be required to start delivering a given composition only when a specific property threshold thereof is achieved, for instance when a predetermined temperature value has been reached. Therefore, the delivery system should ensure that said temperature value is effectively obtained and, moreover, that a proper (typically slow) heat distribution has occurred within said composition.

The aspects mentioned above are applicable not only to traditional industries (like pharma, chemical, automotive, aerospace industries) where a mixing or shaking step is requested to be performed before a final delivery/application step is executed. Indeed, also cellular/biological applications may require that predetermined conditions are maintained or achieved before moving to a successive step. For instance, many experiments involving cells cultures make use of bovine serum which is typically required to be regularly mixed by careful swirling before use in order to keep its native structural state.

The Applicant has thus perceived the need of improving the capability of a fluid delivery system to deliver a fluid which satisfies specific and predetermined fluid properties that are requested for a proper use of that fluid.

In other words, the Applicant has perceived the need of providing a fluid delivery system which can satisfy and guarantee the required delivery conditions for the specific fluid to be delivered, meanwhile ensuring that the delivery system is accurate, efficient, reliable and simple as far as easiness of use and manufacturing process thereof are concerned.

Moreover, the Applicant has perceived the need of providing a fluid delivery system which allows, if needed, to reach sufficiently high fluid pressures and to deliver the fluid at sufficiently high flow rates while avoiding, or at least significantly limiting, the necessity of setting up complex structural solutions of the delivery system for guaranteeing that said sufficiently high fluid pressures and flow rates can be finally achieved.

With specific reference to the medical field, and more particularly with reference to the injection or infusion into a patient's body (generally into a patient's blood vessel that reaches a body portion or a patient's body organ to be treated and/or analyzed, e.g. through scan examinations like X-ray, CT, MRI or ultrasound exams) of liquid medicaments or of diagnostically active contrast agents, the Applicant has perceived the need of improving the hydraulic performance of a powered injector (mainly in terms of maximum pressure and maximum flow rate of the injected fluid) so that a predetermined injection procedure is not affected by any possible additional medical device (e.g. PICC & PORT) already implanted in the patient's body and to which the powered injector is requested to be connected.

Moreover, the need of improving the hydraulic performance of a powered injector is also correlated to the fact that more and more viscous contrast agents are made available on the market, such increased viscosity generally decreasing the injector delivery performance in terms of maximum pressure and maximum flow rate of the injected fluid. Even worst, sometimes said delivery performance is adversely affected also by the habit in some specific countries of injecting the fluid at room temperature, i.e. without pre-warming it at about body temperature before injection, said pre-warming indeed advantageously contributing in reducing the viscosity of said contrast agents.

The Applicant has also perceived the need of improving the delivery performance and accuracy of a fluid delivery system that is requested to sequentially and/or alternately deliver at least two different fluids having different characteristics/properties (e.g. contrast agents with different viscosities, a saline solution, a mixture thereof). In fact, delivering at least two different fluids in alternate sequence requires corresponding alternate opening/closing steps of the different fluid pathways through which said fluids are made to flow, said steps possibly causing the generation of air bubbles within said fluid pathways due to cavitation phenomena, and possibly generating also under- or over-pressure events that may negatively impact the fluid flow rate, for instance in terms of the desired flow rate value to be provided by the fluid delivery system and/or in terms of ensuring regularity and continuity of the fluids flows. Moreover, the alternate opening/closing steps of the different fluid pathways require that valves or clamps are operated on the high-pressure side of the fluid flow, said aspect being very challenging and demanding for a very precise and accurate functioning of the fluid delivery system.

The Applicant has also perceived the need of providing a single fluid delivery system which is able to comply with the various operative applications requested by a given customer. For instance, in case the fluid delivery system is an injector suitable for being used in the medical field, the Applicant has perceived the need of providing a single device which can be selectively operated to perform, for instance, CT, MR and/or Angiography examinations, as well as drugs/medicaments delivery according to the specific medical needs of a predetermined patient, said examinations and fluid delivery being traditionally carried out by using distinct dedicated medical devices (e.g. a CT injector, an MRI injector, an Angiographic injector, an infusion system).

SUMMARY

A simplified summary of the present disclosure is herein presented to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In order to ensure that predefined delivery requirements of a given fluid are achieved before the fluid is started to be delivered, the Applicant has found that a proper recirculation of the fluid within the fluid delivery system allows to guarantee the desired efficiency and quality thereof.

Moreover, the Applicant has found that suitably re-directing the fluid within the fluid delivery system before being delivered outside thereof provides for a pressure equalization within the fluid delivery system which advantageously contributes in easily managing the fluid circulation and also in reducing the technical constraints which are inevitably faced when high pressures are generated.

Furthermore, the Applicant has found that recirculation of the fluid within the fluid delivery system before being delivered outside thereof advantageously allows to remarkably reduce or even completely remove the risk of pressure pulsations, especially at the beginning of the fluid delivery procedure.

The Applicant has also found that recirculation of the fluid within the fluid delivery system before being delivered outside thereof advantageously allows to remarkably reduce or even completely eliminate the latency time of the fluid delivery system, as it will be described in more detail in the following of the present description.

Moreover, in order to provide a fluid delivery system which can ensure to deliver at least two different fluids, and to accurately and precisely achieve for each fluid the desired/predetermined delivery conditions (e.g. in terms of pressure and flow rate), the Applicant has found to provide a fluid delivery system with at least two pump modules, each pump module processing at least one fluid, at least one pump module comprising a dedicated recirculation fluid circuit (sometimes also defined in the present description as recirculation fluid pathway) for recirculating at least one fluid internally to the corresponding pump module when, during operation of the fluid delivery system, said at least one fluid is requested not to be delivered outside of the fluid delivery system (i.e. not to be discharged from said pump module and thus not to be delivered by the fluid delivery system).

The Applicant has also found that a single fluid delivery system which is advantageously versatile and able to conform to customers' different needs can be designed to be adjustable (i.e. of a modular configuration) by providing one or more disposable pump module assemblies, each distinct disposable pump module assembly comprising at least one recirculation fluid circuit as indicated above and being dedicated to satisfying predetermined specific requirements. For instance, in case the fluid delivery system is applied to the medical field and two distinct fluids are requested to be injected into a patient's vascular system, the Applicant has found to provide a modular fluid delivery system (i.e. a modular injector) which comprises at least one disposable pump module assembly whose technical features (e.g. in terms of geometry, size, fluids pathways distribution, . . . ) are suitable for achieving the desired requisites. The Applicant has also found to provide a modular fluid delivery system (i.e. a modular injector) which can be adjusted to perform remarkably different operations (e.g. CT, MRI or angiographic examinations) by making use of one or more dedicated disposable pump module assemblies.

According to the present disclosure, the term "disposable" is meant to indicate a fluid delivery system component that is kept in place and/or used for a limited number of applications or for a limited period of time. For instance, in case the modular fluid delivery system of the present invention is an injector suitable for being applied to the medical field, the term "disposable" indicates a fluid delivery system component which is used for a predetermined maximum number of patients (e.g. from 20 to 60 patients, or even more), or which is discarded at a predetermined maximum period of time (e.g. 24 hours) after installation thereof. It is worthy pointing out that such indicated time limitation is not directly depending on the disposable per se (which could potentially have a substantially unlimited lifetime), but it mainly depends on the characteristics of the fluids to be delivered (drawbacks like crystallization or solidification of the fluid after a given period of time can remarkably impact on disposable lifetime). Alternatively, a disposable fluid delivery system component can be mono-use, i.e. a new component is requested to be installed after each injection procedure, which means that a new component is used for any new patient who is in need of an examination procedure. Such mono-use application can be indicated, for instance, in case of the delivery of a specifically customized mixture (which cannot run the risk of being contaminated by or to contaminate other different substances being delivered to previous or successive patients), or in case of the delivery of a mixture which requires to be immediately delivered since it cannot undergo even short waiting times.

Therefore, an aspect of the present disclosure provides for a modular fluid delivery system comprising:

- at least one supply station for supplying at least one fluid, and
- a pressurizing unit for pressurizing said at least one fluid, said pressurizing unit comprising at least one driving unit and at least one disposable pump module assembly,
- characterized in that said at least one disposable pump module assembly comprises:
- at least one disposable pump module which comprises a supporting element defining:
  - at least one chamber receiving a piston therein, said piston having a plunger that, in cooperation with internal walls of said chamber, defines first and second variable-volume sub-chambers;
  - at least one inlet fluid circuit pathway;
  - at least one outlet fluid circuit pathway, and
  - at least one recirculation fluid circuit pathway, and
- a fluid circuit tubing which comprises:
  - at least one inlet fluid circuit tubing at least partially received within said at least one inlet fluid circuit pathway, said at least one inlet fluid circuit tubing being in fluid communication with said at least one supply station and with said at least one chamber for supplying said at least one fluid to said first and second variable-volume sub-chambers;
  - at least one outlet fluid circuit tubing at least partially received within said at least one outlet fluid circuit pathway, said at least one outlet fluid circuit tubing being in fluid communication with said at least one chamber for discharging the fluid alternatively from said first and second variable-volume sub-chambers, said outlet fluid circuit tubing being separate from said inlet fluid circuit tubing, and
  - at least one recirculation fluid circuit tubing at least partially received within said at least one recirculation fluid circuit pathway, said at least one recirculation fluid circuit tubing fluidically connecting said first and second variable-volume sub-chambers.

More specifically, one or more aspects of the present disclosure are set out in the independent claims, and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solutions of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
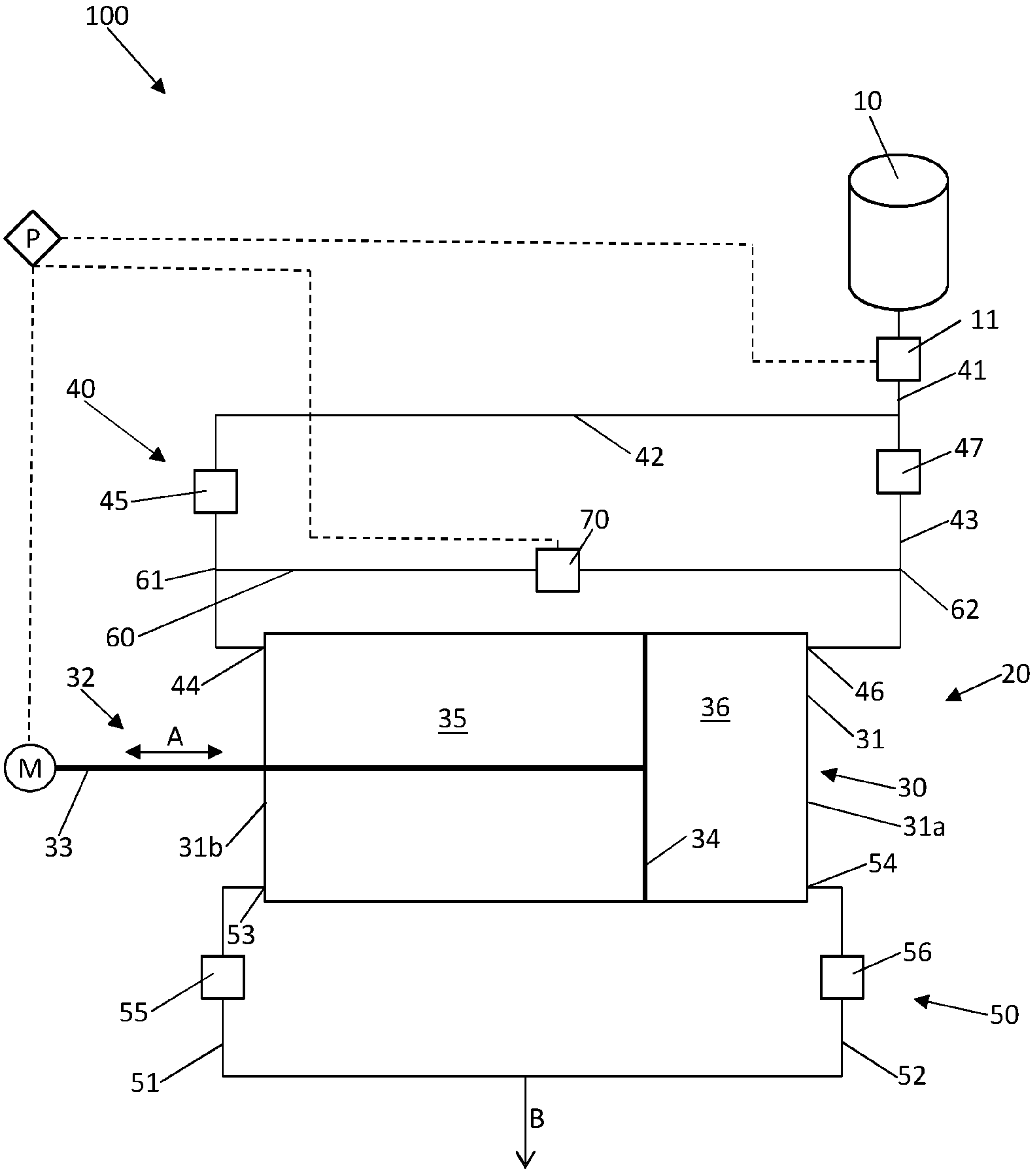
FIG. 1 shows a schematic representation of a fluid delivery system to which an embodiment of the present disclosure can be applied.

With reference to FIG. 1, a schematic representation of a fluid delivery system 100 is shown according to an embodiment of the present disclosure. Fluid delivery system 100 is used for delivering a fluid contained in a supply station 10, said fluid being of different nature based on the specific technical field wherein the fluid delivery system is implemented.

For instance, in case fluid delivery system 100 is an injection system for being used in the medical field, the fluid contained in supply station 10 and to be injected into the patient's vascular system can be a contrast agent which is administered for enhancing contrast of target (body) features (for example, human body's structures or organs) within the patients during scan examinations thereof, e.g. during CT, MRI or ultrasound exams. Particularly, in imaging applications (wherein a visual representation of the interior of the patients is created in a non-invasive way without turning to surgery techniques) the use of a contrast agent makes the target features more conspicuous. As a result, target features that would otherwise be less distinguishable from other nearby features (for example, surrounding tissues) are advantageously highlighted. This significantly facilitates the task of clinicians in diagnostic applications, and particularly the identification and/or characterization of lesions, the monitoring of their evolution or response to medical treatments. For example, in CT applications the contrast agent may be an iodine-based contrast agent comprising diatrizoate, ioxaglate, iopamidol, iohexol, ioxilan, iopromide or iodixanol. An example of a commercial contrast agent comprising iopamidol is ISOVUE®, manufactured by Bracco Diagnostics Inc.®.

According to an embodiment of the present disclosure, fluid delivery system 100 is configured for delivering Ultrasound Contrast Agents (USCA) in a continuous injection/infusion mode and/or as a bolus. In particular, fluid delivery system 100 is used for delivering a liquid composition which comprises a suspension of microparticles homogeneously distributed in a liquid carrier, preferably an aqueous liquid carrier, said microparticles containing entrapped pure gases or gas mixtures including at least one physiologically acceptable halogenated gas. This halogenated gas is preferably selected among CF4, C2F6, C3F8, C4F8, C4F10, C5F12, C6F14 or SF6. The gas mixtures can also contain gases such as air, oxygen, nitrogen, helium, xenon or carbon dioxide. In a number of cases said microparticles (microbubbles or microballoons) contain mixtures of nitrogen or air with at least one perfluorinated gas in proportions which may vary between 1 and 99%. An example of a commercial contrast agent that is used in Contrast Enhanced Ultrasound (CEUS) applications is SonoVue® (Sulphur hexafluoride microbubbles), manufactured by Bracco Suisse®.

Still referring to the medical field, the fluid contained in supply station 10 and to be injected into the patient's vascular system can also be a saline solution comprising a physiological or isotonic solution (e.g. sodium chloride). Alternatively, said fluid can be a liquid medicament or a drug.

As already mentioned above, delivery system 100 of the present disclosure can be used for delivering fluids in many technological fields, not necessarily correlated to the medical/diagnostic field. For instance, the fluid contained in supply station 10 can be a glue formulation, a painting formulation, a coating formulation, or a substance/formulation for which a delivery property (e.g. temperature) is requested to be properly reached/controlled.

Fluid delivery system 100 comprises a pressurizing unit 20 which operates on the fluid so that it will exit the fluid delivery system (and thus it will be delivered) at a predetermined pressure and flow rate, previously set up based on the requirements correlated to the specific delivery use. In detail, pressurizing unit 20 comprises a pump module 30 and a driving unit M, said driving unit being associated to the pump module for the operation thereof. Pump module 30 comprises a chamber 31 within which a piston 32 is reciprocated (i.e. moved back and forth—see double arrow A) by driving unit M. According to the embodiment shown in the figures, chamber 31 is represented as a cylindrical barrel (e.g. like a syringe barrel); however, other different configurations suitable for the purpose can be envisaged as well. Piston 32 comprises a piston rod 33 and a plunger 34, the plunger being arranged to be substantially perpendicular to the piston rod and having a radial extension which substantially corresponds to the chamber radial extension, i.e. to the chamber width. Therefore, in cooperation with internal walls of chamber 31, plunger 34 defines a first sub-chamber 35 on one side of the plunger (on the left side of the plunger in the embodiment of FIG. 1) and a second sub-chamber 36 on the opposite side of the plunger (on the right side of the plunger in the embodiment of FIG. 1). During operation of the fluid delivery system, piston 32 is moved back and forth (see double arrow A) and thus the overall volume of said first and second sub-chambers 35, 36 is continuously and alternately changing, thus these sub-chambers being variable-volume sub-chambers. For instance, when piston 32 is moved to the right in FIG. 1, the volume of first sub-chamber 35 is increased while the volume of second sub-chamber 36 is decreased; on the contrary, when piston 32 is moved to the left in FIG. 1, the volume of second sub-chamber 36 is increased while the volume of first sub-chamber 35 is decreased. According to the embodiment shown in FIG. 1, plunger 34 is provided at an axial end of piston rod 33 (i.e. at the axial end opposite to the axial end connected to driving unit M). Alternatively, plunger 34 can be provided at a different position along the longitudinal extension of piston rod 33 (embodiment not shown in the figures) with the proviso that both base walls 31*a*,31*b* of chamber 31 allow a sealed axial movement of piston rod 33 therethrough.

Fluid delivery system 100 of the present disclosure further comprises an inlet fluid circuit 40 which is in fluid communication with supply station 10 and with pump module 30. Inlet fluid circuit 40 comprises fluid pathways which supply the fluid (contained in supply station 10) to first variable-volume sub-chamber 35 and to second variable-volume sub-chamber 36 so that chamber 31 is filled with a suitable fluid volume amount to be delivered (arrow B).

In detail, inlet fluid circuit 40 comprises a first inlet fluid pathway 41 which is in fluid communication with supply station 10, said first inlet fluid pathway 41 including a supply station valve 11 that allows the fluid to be discharged from supply station 10. Supply station valve 11 is an active valve that is operated by the fluid delivery system, as it will be explained in detail in the following of the present description.

Downstream from supply station valve 11, inlet fluid circuit 40 branches into a second inlet fluid pathway 42 and a third inlet fluid pathway 43 which are in fluid communication with first sub-chamber 35 and second sub-chamber 36, respectively. First sub-chamber 35 is provided with a first inlet port 44 which allows second inlet fluid pathway 42 to be in fluid communication with first sub-chamber 35. Analogously, second sub-chamber 36 is provided with a second inlet port 46 which allows third inlet fluid pathway 43 to be in fluid communication with second sub-chamber 36.

Upstream from the first inlet port 44, second inlet fluid pathway 42 is provided with a first inlet fluid circuit valve 45 which allows the fluid to flowing into first sub-chamber 35 through second inlet fluid pathway 42. According to an embodiment of the present disclosure, first inlet fluid circuit valve 45 is a check valve, i.e. a one-way valve which allows the fluid to flow through it in only one direction, specifically from supply station 10 towards first sub-chamber 35, thereby avoiding that the fluid flows back towards supply station 10.

Analogously, upstream from second inlet port 46, third inlet fluid pathway 43 is provided with a second inlet fluid circuit valve 47 which allows the fluid to flowing into second sub-chamber 36 through third inlet fluid pathway 43. According to an embodiment of the present disclosure, second inlet fluid circuit valve 47 is a check valve, i.e. a one-way valve which prevents reverse flow allowing the fluid to flow through it in only one direction, specifically from supply station 10 towards second sub-chamber 36, thereby avoiding that the fluid flows back towards supply station 10.

Preferably, first and second inlet fluid circuit valves 45, 47 are ball check valves wherein a ball is present inside the body valve for regulating the fluid flow.

Fluid delivery system 100 further comprises an outlet fluid circuit 50 which is separate from inlet fluid circuit 40. Outlet fluid circuit 50 is in fluid communication with pump module 30 and it comprises a first outlet fluid pathway 51 and a second outlet fluid pathway 52 that allow fluid delivery system 100 to discharge the fluid from chamber 31 and to deliver it outside the fluid delivery system (see arrow B). In detail, first sub-chamber 35 is provided with a first outlet port 53 which allows first outlet fluid pathway 51 to be in fluid communication with first sub-chamber 35. Analogously, second sub-chamber 36 is provided with a second outlet port 54 which allows second outlet fluid pathway 52 to be in fluid communication with second sub-chamber 36. As it will be described in detail in the following of the present disclosure, in operation first and second outlet fluid pathways 51, 52 of outlet fluid circuit 50 discharge the fluid alternatively from first sub-chamber 35 and from second sub-chamber 36.

Downstream from first outlet port 53, first outlet fluid pathway 51 is provided with a first outlet fluid circuit valve 55 which allows the fluid to being discharged from first sub-chamber 35 through first outlet fluid pathway 51. According to an embodiment of the present disclosure, first outlet fluid circuit valve 55 is a check valve, i.e. a one-way valve which prevents reverse flow allowing the fluid to flow through it in only one direction, specifically exiting from first sub-chamber 35, thereby avoiding that the fluid flows back into said first sub-chamber 35.

Analogously, downstream from second outlet port 54, second outlet fluid pathway 52 is provided with a second outlet fluid circuit valve 56 which allows the fluid to being discharged from second sub-chamber 36 through second outlet fluid pathway 52. According to an embodiment of the present disclosure, second outlet fluid circuit valve 56 is a check valve, i.e. a one-way valve which allows the fluid to flow through it in only one direction, specifically exiting from second sub-chamber 36, thereby avoiding that the fluid flows back into said second sub-chamber 36.

Preferably, first and second outlet fluid circuit valves 55, 56 are spring loaded check valves wherein a spring component is used to support valve operation by eliminating the effect of gravity on the check valve function. More preferably, first and second outlet fluid circuit valves 55, 56 are spring loaded ball check valves.

According to the present disclosure, fluid delivery system 100 further comprises a recirculation fluid circuit 60 fluidically connecting said first and second variable-volume sub-chambers 35, 36, said recirculation fluid circuit 60 cooperating with an actuator 70 for managing the fluid passage in both directions between said first and second variable-volume sub-chambers 35, 36. Recirculation fluid circuit 60 is an additional fluid circuit, i.e. a further fluid pathway which allows a direct fluid communication between first and second variable-volume sub-chambers 35, 36. Therefore, in the present description the terms recirculation fluid circuit or additional fluid circuit or recirculation fluid pathway are equivalent to each other and meant to indicate the same component of the fluid delivery system.

According to the embodiment shown in FIG. 1, recirculation fluid circuit 60 is external to chamber 31 and it fluidically connects separate branches of inlet fluid circuit 40 upstream from the inlet ports of sub-chambers 35, 36 and downstream from inlet fluid circuit valves 45, 47. In detail, a first axial end 61 of recirculation fluid circuit pathway 60 fluidically connects with second inlet fluid pathway 42 of inlet fluid circuit 40 downstream from first inlet fluid circuit valve 45. Analogously, a second axial end 62 of recirculation fluid circuit 60 fluidically connects with third inlet fluid pathway 43 of inlet fluid circuit 40 downstream from second inlet fluid circuit valve 47.

Actuator 70 is an active valve that is operated by the fluid delivery system, as it will be explained in detail in the following of the present description. Preferably, actuator 70 is an electro-mechanical driven valve that is automatically controlled and operated by a processor P of fluid delivery system 100. As schematically shown in the figures, processor P controls and operates actuator 70, driving unit M and supply station valve 11. In other words, processor P is a control unit which governs and actuates some components of the fluid delivery system in accordance with a predetermined delivery (injection) protocol selected by the operator.

Figure 2:
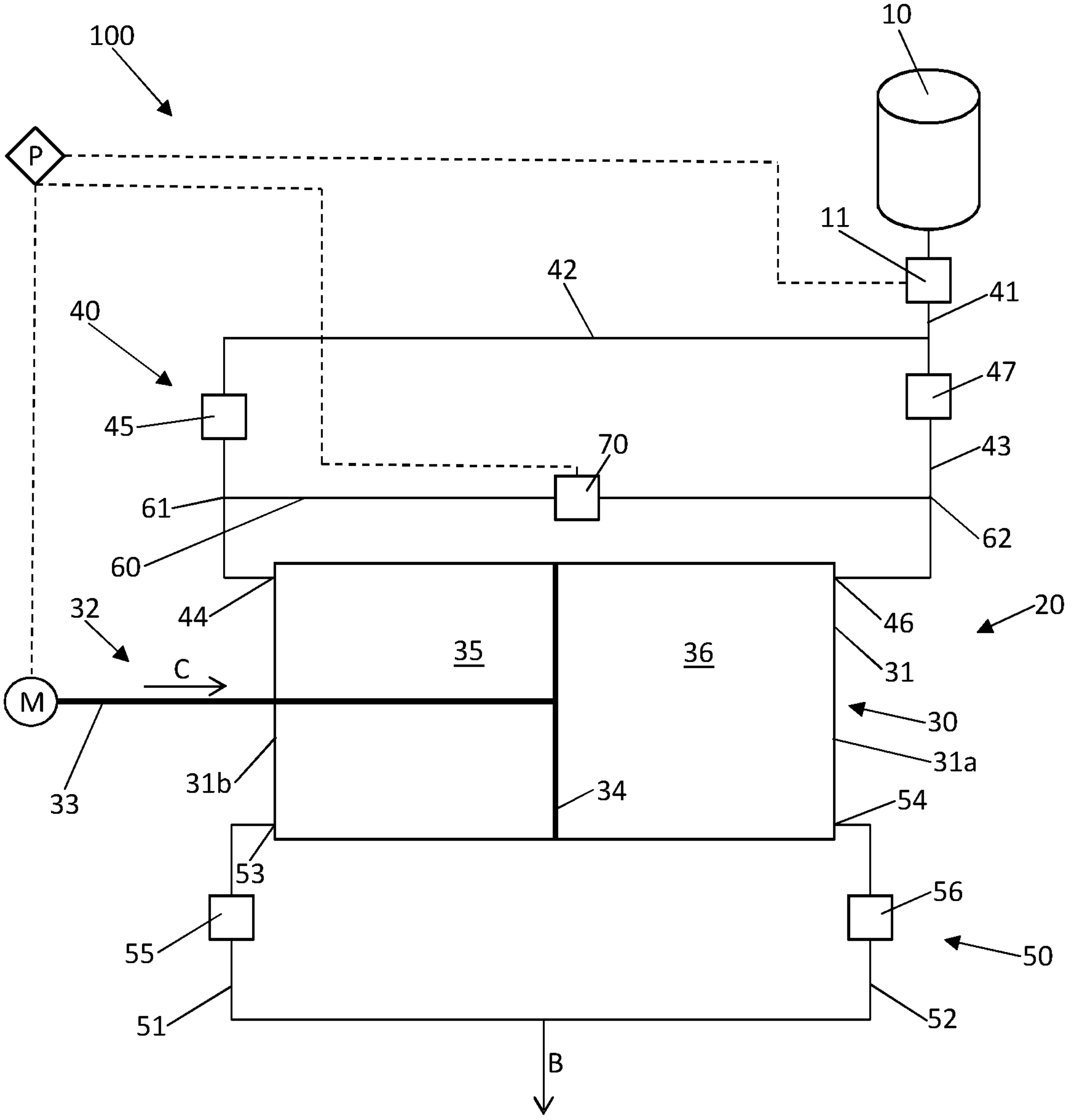
FIG. 2 to FIG. 4 show a schematic representation of the operation steps of the fluid delivery system shown in FIG. 1.

Operation of the delivery system according to the first embodiment (shown in FIG. 1) of the present disclosure is described in the following with reference to FIG. 2-FIG. 4.

Supply station 10 contains the fluid (not shown) which has to be delivered by delivery system 100 (arrow B).

As a first initiation step, the method of fluid delivery according to the present disclosure comprises the step of filling first and second sub-chambers 35, 36 with the fluid to be delivered. In order to perform said filling step, processor P opens supply station valve 11, it closes actuator 70 of recirculation fluid circuit 60 and it acts on driving unit M for moving piston 32 within chamber 31, thereby allowing the fluid to exit supply station 10 and to flow through inlet fluid circuit 40. In detail, as soon as piston 32 is axially translated along a first direction (e.g. arrow C of FIG. 2), under pressure is generated in the first sub-chamber (e.g. sub-chamber 35) which is increasing its volume due to the piston axial movement, and the fluid flows through first inlet fluid pathway 41 and through second inlet fluid pathway 42 of inlet fluid circuit 40, through the corresponding first inlet fluid circuit valve (e.g. first inlet fluid circuit valve 45), and then it enters and fills said first sub-chamber. At the same time, the air contained within the second sub-chamber (e.g. sub-chamber 36)—which is decreasing its volume due to the piston axial movement—is primed away from the delivery system through venting means possessed by the opposite second inlet fluid circuit valve (e.g. second inlet fluid circuit valve 47). Successively, in order to fill the second sub-chamber and prime the first sub-chamber, processor P acts on driving unit M for inverting the piston movement so that the piston is axially translated along a second direction opposite to the first direction (e.g. arrow D of FIG. 3). Since actuator 70 is kept closed while the piston is moving, under pressure is generated in the second sub-chamber (e.g. sub-chamber 36) which is increasing its volume due to the piston axial movement, and the fluid flows through first inlet fluid pathway 41 of inlet fluid circuit 40, through the corresponding second inlet fluid circuit valve (e.g. second inlet fluid circuit valve 47), and then it enters and fills said second sub-chamber. At the same time, the air still contained within the first sub-chamber (e.g. sub-chamber 35)—which is decreasing its volume due to the piston axial movement—is primed away from the delivery system through venting means possessed by the corresponding first inlet fluid circuit valve (e.g. first inlet fluid circuit valve 45). During the priming step some fluid exits the delivery system so that priming of the outlet fluid circuit 50 is performed too.

Alternatively, air priming of the fluid delivery system is performed by dedicated venting means (not shown in the drawings) which is separate from the fluid circuit valves. According to an alternative embodiment, a dedicated venting means is associated with each valve of the fluid delivery system. According to a further embodiment, only one dedicated venting means is possessed by the fluid delivery system. Preferably said only one dedicated venting means is associated with the actuator of the recirculation fluid pathway.

As soon as chamber 31 is filled up with the fluid and priming of the delivery system is completed, processor P closes supply station valve 11 and opens actuator 70 of recirculation fluid circuit 60, while driving unit M is still activated and keeps piston 32 axially translating within chamber 31.

Alternatively, processor P opens actuator 70 of recirculation fluid circuit 60 while still keeping supply station valve 11 open.

While piston 32 is moving towards base wall 31*a* of chamber 31 (see arrow C of FIG. 2), translation of plunger 34 causes a volume increase of first sub-chamber 35 and a corresponding volume decrease of second sub-chamber 36. Moreover, since actuator 70 is in an open state at this stage of the procedure, the fluid initially contained within second sub-chamber 36 is pushed by plunger 34 out of chamber 31 passing through second inlet port 46 and then, by flowing into recirculation fluid circuit 60 and, by passing through open actuator 70, it enters first sub-chamber 35 by accessing first inlet port 44.

It has to be pointed out that the fluid contained inside second sub-chamber 36 and pushed by plunger 34 is allowed neither flowing back into supply station 10 nor accessing second fluid pathway 52 of outlet fluid circuit 50. In fact, supply station valve 11 is closed and both first and second inlet fluid circuit valves 45, 47 are one-way valves which allow the fluid flowing from supply station 10 into chamber 31, but not vice versa, thereby avoiding the fluid discharged from sub-chamber 36 flowing back through first and second inlet fluid pathways 41, 42 of inlet fluid circuit 40. Moreover, since second outlet fluid circuit valve 56 automatically opens only when the fluid discharged from second sub-chamber 36 has a sufficiently high pressure for overcoming the internal resilience of said valve (preferably, second outlet fluid circuit valve 56 is a ball spring-loaded check valve), when actuator 70 is in the open state the fluid discharged from second sub-chamber 36 does not have enough force to overcome the internal resilience of second outlet fluid circuit valve 56, and thus the fluid is not delivered outside of fluid delivery system 100, on the contrary the fluid discharged from second sub-chamber 36 re-fills first sub-chamber 35.

Figure 3:
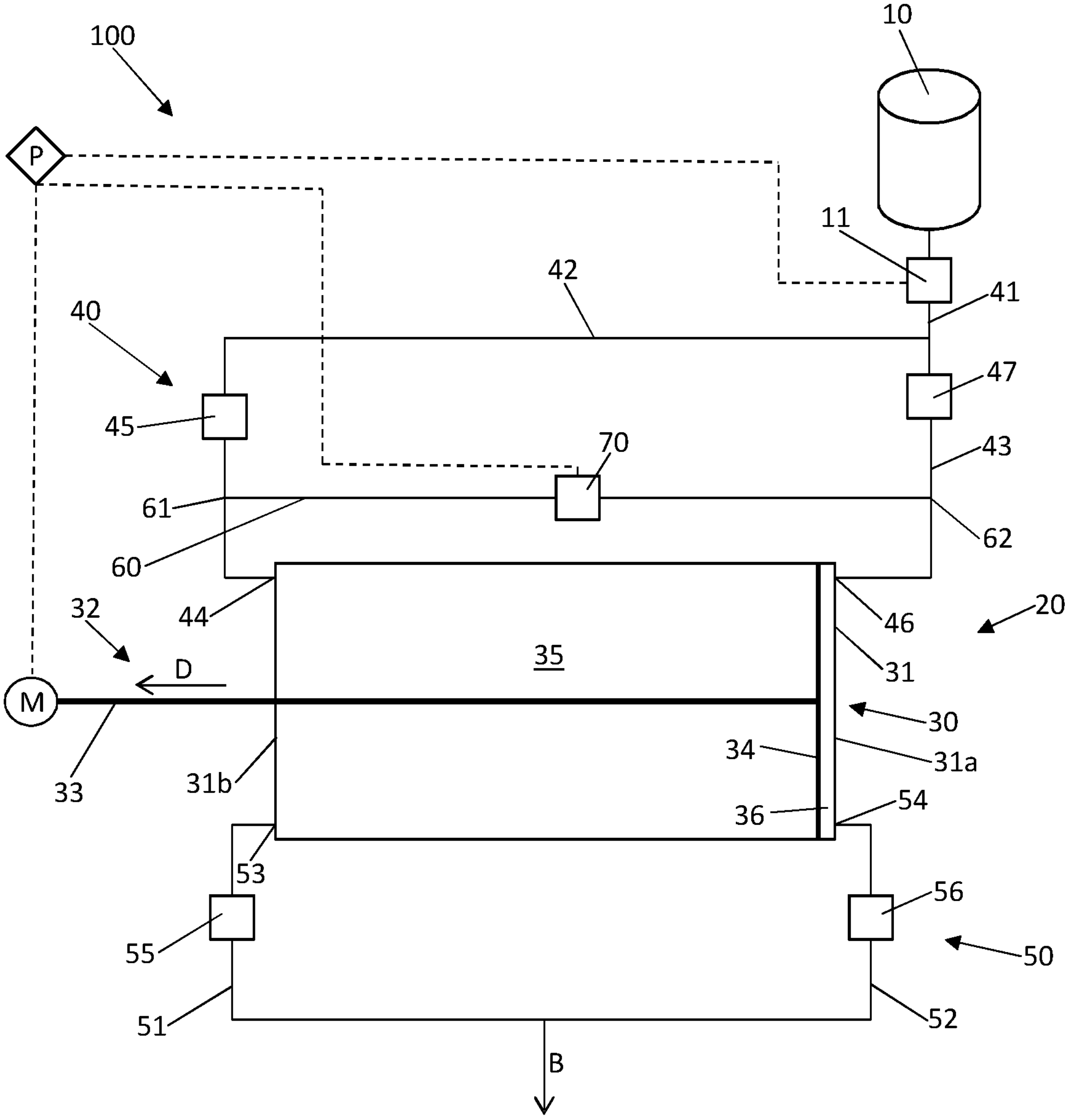
Figure 4:
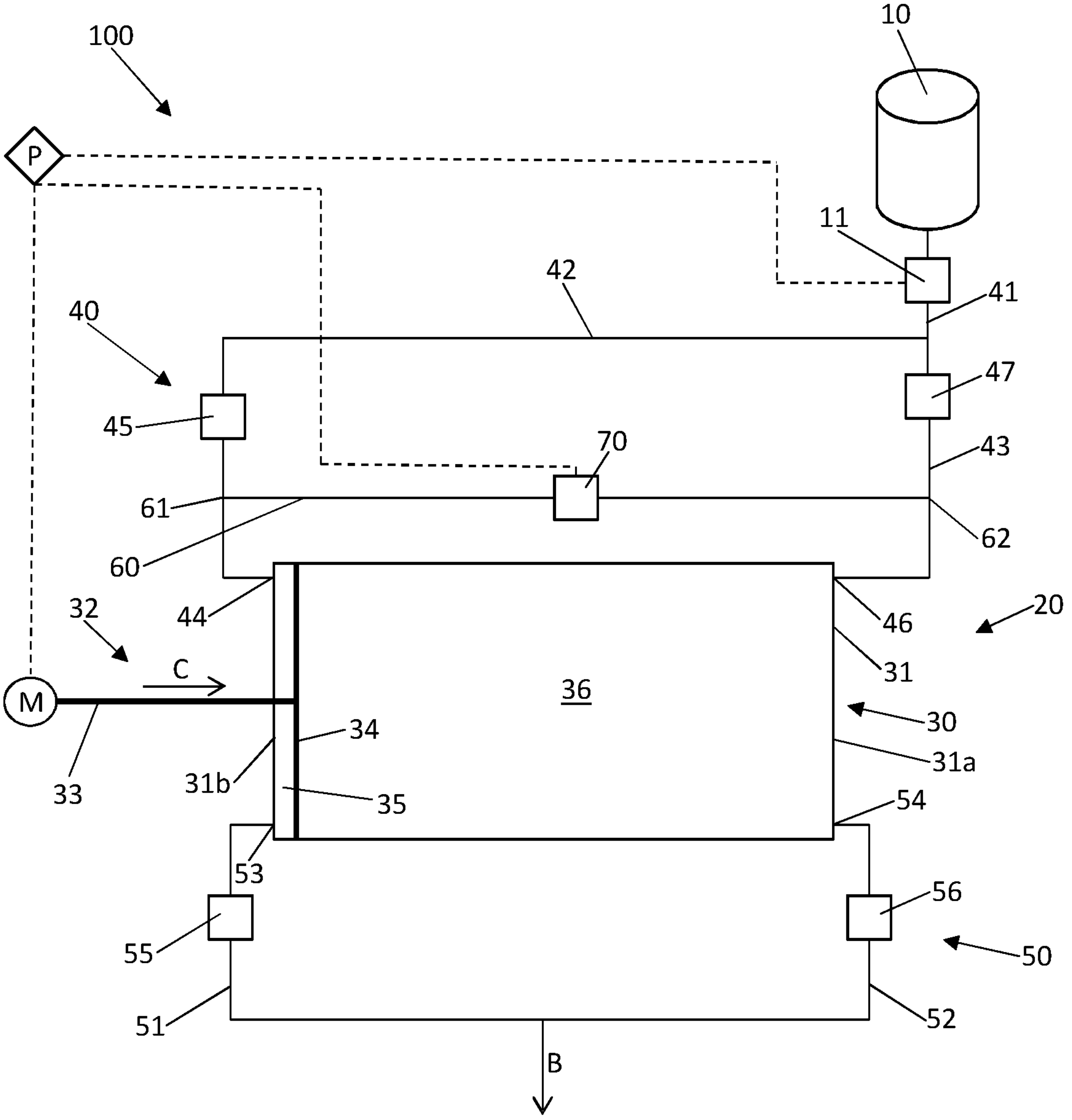

As soon as piston 32 has reached its first end-stop, i.e. plunger 34 has completed its axial translation in a first direction (right direction in FIG. 2—see arrow C) and it arrives in proximity of base wall 31*a* of chamber 31 so that second sub-chamber 36 contains a substantially small volume of fluid while first sub-chamber 35 contains a large volume of fluid, processor P acts on driving unit M to reverse piston axial translation (left direction in FIG. 3—see arrow D). During reverse movement of piston 32 within chamber 31 the same operative conditions mentioned above still apply, i.e. actuator 70 is kept in its open state while supply station valve 11 is kept in its closed state.

Axial translation of the plunger in the reverse direction causes a volume increase of second sub-chamber 36 and a corresponding volume decrease of first sub-chamber 35. Thanks to actuator 70 being in its open state, the fluid initially contained within first sub-chamber 35 is pushed by plunger 34 out of chamber 31 passing through first inlet port 44 and then, flowing into recirculation fluid circuit 60 and through open actuator 70, it enters second sub-chamber 36 passing through second inlet port 46.

The considerations provided above with reference to piston translation in a first direction (right direction of FIG. 2—see arrow C) still apply also to piston translation in a second direction, opposite to first direction (left direction of FIG. 3—see arrow D). Therefore, the fluid contained inside first sub-chamber 35 and pushed by plunger 34 is allowed neither flowing back into supply station 10 nor accessing first outlet fluid pathway 51 of outlet fluid circuit 50. In fact, supply station valve 11 is closed and both first and second inlet fluid circuit valves 45, 47 are one-way valves which allow the fluid flowing from supply station 10 into chamber 31, but not vice versa, thereby avoiding the fluid discharged from first sub-chamber 35 flowing back through first and second inlet fluid pathways 41, 42 of inlet fluid circuit 40. Moreover, since first outlet fluid circuit valve 55 automatically opens only when the fluid discharged from first sub-chamber 35 has a sufficiently high pressure for overcoming the internal resilience of said valve (preferably, first outlet fluid circuit valve 55 is a ball spring-loaded check valve), when actuator 70 is in the open state the fluid discharged from first sub-chamber 35 does not have enough force to overcome the internal resilience of first outlet fluid circuit valve 55, and thus the fluid is not delivered outside of fluid delivery system 100, on the contrary the fluid discharged from first sub-chamber 35 re-fills second sub-chamber 36.

As soon as piston 32 has reached its second end-stop, i.e. plunger 34 has completed its axial translation in the second direction (left direction in FIG. 3—see arrow D) and it arrives in proximity of base wall 31*b* of chamber 31 so that first sub-chamber 35 contains a substantially small volume of fluid while second sub-chamber 36 contains a large volume of fluid, processor P acts on driving unit M to reverse again piston axial translation (right direction in FIG. 4—see arrow C), thereby starting a new charge/discharge cycle of chamber 31 of fluid delivery system 100. Of course, any number of cycles can be arranged for, said number depending on the requirements of the specific fluid to be delivered and on the requirements of the specific application where the delivery system is implemented.

It is apparent from the above that the fluid delivery system of the present disclosure allows a continuous and predefined movement (e.g. in terms of volumes, piston translational speed) of the fluid before exiting the fluid delivery system. As already mentioned above, this aspect of the present disclosure is particularly advantageous in case a specific fluid property (e.g. composition homogeneity, temperature, viscosity, mixture, fluidity) is requested to be achieved and/or maintained before starting delivery of the fluid. In fact, the fluid delivery system according to the present disclosure allows the fluid introduced into chamber 31 to be continuously recirculated by being alternately charged/discharged between first and second sub-chambers 35, 36 when fluid delivery system 100 is not delivering, i.e. the fluid is not definitely exiting the fluid delivery system. Thanks to recirculation fluid circuit 60 and actuator 70 associated thereto, recirculation of the fluid and redistribution thereof between the two sub-chambers contributes in balancing the pressure therein. This aspect is particularly advantageous since it allows to operate the system at a limited (low) pressure, at least in the initial stage when the delivery system is not yet delivering the fluid outside the system, thereby limiting the technical constraints which would need to be implemented if the system were required to operate at higher pressure values.

Furthermore, the method of delivery according to the present disclosure comprises the step of starting delivery (i.e. outside of the fluid delivery system) of the fluid contained within chamber 31. In order to perform said step, processor P closes actuator 70 of recirculation fluid circuit 60 and it opens supply station valve 11. Therefore, during delivery of the fluid (fluid exiting the delivery system—see arrow B), supply station valve 11 is maintained in its open state because it is important to refill the sub-chambers with new fluid in order to avoid fluidic perturbations possibly impacting on the correct functioning of the piston and, consequently, of the overall delivery system. Since closing actuator 70 prevents any fluid to flow through recirculation fluid circuit 60 (while, as already mentioned above, first and second inlet fluid circuit valves 45, 47 do not allow any flow back of the fluid towards supply station 10), pushing plunger 34 in the first direction (arrow C) and in the second opposite direction (arrow D) allows the fluid to exit, respectively, second outlet port 54 and first outlet port 53. Therefore, when the fluid is pushed to pass through second outlet port 54 (arrow C), the fluid flows into second outlet fluid pathway 52 of outlet fluid circuit 50 and then it passes through second outlet fluid circuit valve 56 because at this stage of the procedure, since actuator 70 is closed, the fluid pressure is sufficiently high to overcome the internal resilience of said second outlet fluid circuit valve 56. Analogously, when the fluid is pushed to pass through first outlet port 53 (arrow D), the fluid flows into first outlet fluid pathway 51 of outlet fluid circuit 50 and then it passes through first outlet fluid circuit valve 55 because at this stage of the procedure, since actuator 70 is closed, the fluid pressure is sufficiently high to overcome the internal resilience of said first outlet fluid circuit valve 55. Consequently, the fluid is finally delivered (arrow B) by sequentially discharging it from first and second sub-chambers 35, 36. In fact, since first and second outlet fluid circuit valves 55, 56 are one-way valves, the fluid cannot flow back through the under-pressurized pathway and thus it is forced to be delivered (arrow B).

As mentioned above, during the step of delivering the fluid (arrow B), supply station valve 11 is kept open so that new fluid can alternately enter the two sub-chambers and undesired perturbations effects would not take place while the piston is axially translating within chamber 31. Even though the new fluid entering the system during the step of delivering has not passed through actuator 70 and recirculation fluid circuit 60, it should be noted that the new fluid is not instantly delivered. In fact, the new fluid enters the sub-chamber that is under pressure, while the fluid that is delivered by the system is the one contained in the pressurized sub-chamber. Therefore, before being delivered, the new fluid is permanently moving and mixing within the respective sub-chamber thanks to the piston axial translation, thereby ensuring that the desired delivery conditions are reached before finally exiting the system.

As already mentioned above, the Applicant has found that recirculation of the fluid within chamber 31, by letting the fluid flowing through recirculation fluid circuit 60 and actuator 70 associated thereto, can remarkably reduce or even completely remove the risk of pressure pulsations when the fluid is being delivered, especially at the beginning of the fluid delivery procedure. Indeed, the fluid delivery system according to the present disclosure can properly control pressure drops or pressure spikes, occurring when piston 32 starts moving, thanks to the presence of recirculation fluid circuit 60 and actuator 70. In fact, according to the present disclosure, the fluid delivery system starts delivering the fluid (outside of the fluid delivery system) when recirculation of the fluid inside chamber 31 has already begun, therefore delivery will start when the piston is already moving inside chamber 31. This clearly means that the start of fluid delivery is not simultaneous with the start of piston movement since delivery of the fluid is started when the piston is already axially translating within chamber 31 for allowing said fluid recirculation to be performed.

Furthermore, as already mentioned above, the Applicant has also found that recirculation of the fluid within chamber 31, by letting the fluid flowing through recirculation fluid circuit 60 and actuator 70 associated thereto, can remarkably reduce or even completely eliminate the latency time of the fluid delivery system. The latency time is the technical time which the fluid delivery system inevitably requires in order to be ready to deliver the fluid. In fact, as soon as processor P instructs to deliver electric current to driving unit M, typically said electric current builds up an electromagnetic field which acts on rotor magnets that generate a torque on the gears, thereby causing the piston to start its movement. When the piston starts moving, fluid pressure starts building up and it still needs some additional time to reach and overcome the pressure threshold value which is set up for first and second outlet fluid circuit valves 55, 56. The sum of all these times is called "latency time" and it is far from being negligible, thereby inevitably causing a delay in fluid delivery out of the fluid delivery system. Thanks to the presence of recirculation fluid circuit 60 and actuator 70 associated thereto, fluid delivery system 100 of the present disclosure can overcome or reduce said latency time since, in order to perform fluid recirculation within chamber 31, piston 32 starts moving well in advance to fluid delivery. Therefore, as soon as processor P closes actuator 70 for starting delivery the fluid (arrow B), the fluid pressure immediately increases and very quickly overcomes the pressure threshold value which is set up for first and second outlet fluid circuit valves 55, 56. Consequently, the fluid is delivered by the system very soon after processor P has ordered to start delivering.

Figure 5:
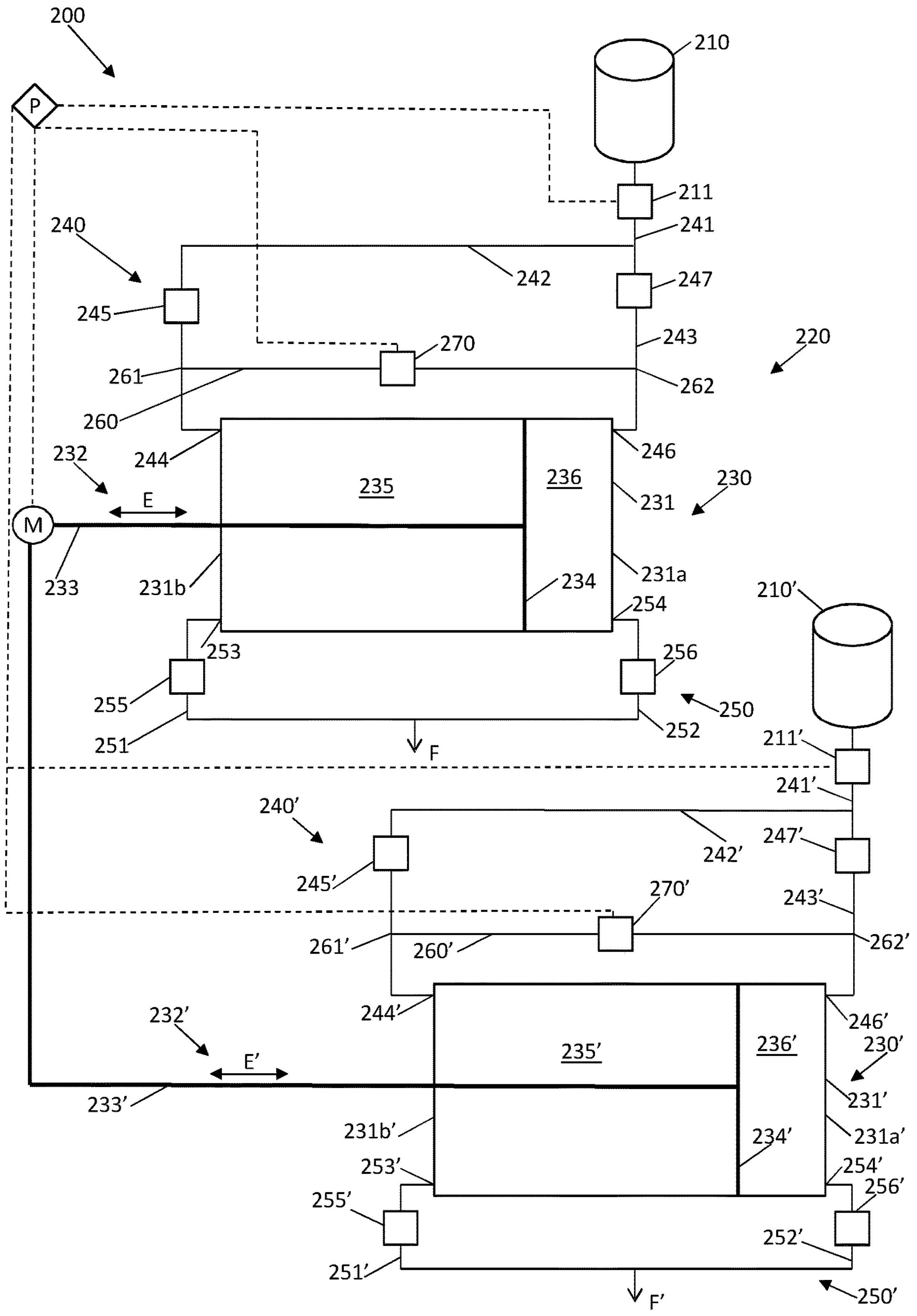
FIG. 5 shows a schematic representation of an alternative fluid delivery system to which an embodiment of the present disclosure can be applied.

With reference to FIG. 5, a schematic representation is shown of a further fluid delivery system 200 according to an alternative embodiment of the present disclosure in which two pump modules 230, 230' are arranged in parallel. Fluid delivery system 200 is used for delivering a first fluid contained in a first supply station 210 and a second fluid contained in a second supply station 210', wherein said first fluid and said second fluid are different from each other.

In case fluid delivery system 200 is an injection system for being used in the medical field, the first fluid contained in first supply station 210 and to be injected into a patient's vascular system can be, for instance, a contrast agent while the second fluid contained in second supply station 210' can be a saline solution comprising a physiological or isotonic solution (e.g. sodium chloride). Alternatively, said first fluid and/or said second fluid can be a liquid medicament or a drug.

As already mentioned above, fluid delivery system 200 of the present disclosure can be used for delivering fluids in many technological fields, not necessarily strictly correlated to the medical/diagnostic field. For instance, the first fluid and the second fluid contained, respectively, in first and second supply stations 210, 210' can be two or more components of a glue formulation, of a painting formulation, of a coating formulation, or of a substance/formulation for which a delivery property (e.g. temperature) is requested to be properly reached/controlled.

Fluid delivery system 200 comprises a pressurizing unit 220 which operates on the first fluid and the second fluid so that, alternately, they will be delivered outside of the fluid delivery system (at a predetermined pressure and flow rate, previously set up by the operator or by the fluid delivery system processor/control unit, based on the requirements designed for the specific delivery use) and recirculated within the fluid delivery system, as it will be disclosed in detail in the following of the present description. Pressurizing unit 220 comprises first pump module 230, second pump module 230' and a driving unit M which is associated to the two pump modules for operation/actuation thereof. Each pump module 230, 230' respectively comprises a chamber 231, 231' within which a piston 232, 232' is reciprocated (i.e. moved back and forth—see double arrows E, E') by driving unit M. According to the embodiment shown in the figures, chambers 231, 231' are represented as cylindrical barrels (e.g.

like a syringe barrel); however other different configurations suitable for the purpose can be envisaged as well. Each piston 232, 232' respectively comprises a piston rod 233, 233' and a plunger 234, 234', the plunger being arranged to be substantially perpendicular to the piston rod and having a radial extension which substantially corresponds to the chamber radial extension (i.e. to chamber width). Therefore, in cooperation with the internal walls of said chambers 231, 231', each plunger 234, 234' defines respective first sub-chambers 235, 235' on one side of the plunger (on the left side of the plungers in the embodiment of FIG. 5) and respective second sub-chambers 236, 236' on the opposite side of the plunger (on the right side of the plungers in the embodiment of FIG. 5). During operation of fluid delivery system 200, piston 232, 232' is moved back and forth (see double arrow E, E') and thus the overall volume of said first 235, 235' and second 236, 236' sub-chambers is continuously and alternately changed, these sub-chambers being variable-volume sub-chambers. For instance, when piston 232, 232' is moved to the right in FIG. 5, the volume of first sub-chambers 235, 235' is increased while the volume of second sub-chambers 236, 236' is decreased; on the contrary, when piston 232, 232' is moved to the left in FIG. 5, the volume of second sub-chambers 236, 236' is increased while the volume of first sub-chambers 235, 235' is decreased. According to the embodiment shown in FIG. 5, plunger 234, 234' is provided at an axial end of piston rod 233, 233' (i.e. at the axial end opposite to the axial end that is connected to driving unit M). Alternatively, plunger 234, 234' can be provided at a different position along the longitudinal extension of piston rod 233, 233' (embodiment not shown in the figures) with the proviso that base walls 231*a*, 231*b* of chamber 231 as well as base walls 231*a*', 231*b*' of chamber 231' allow a sealed axial movement of piston rod 233, 233' therethrough (i.e. through said chambers).

Fluid delivery system 200 of the present disclosure further comprises a first inlet fluid circuit 240 and a second inlet fluid circuit 240'. In detail, first inlet fluid circuit 240 is in fluid communication with first supply station 210 and with first pump module 230, while, analogously, second inlet fluid circuit 240' is in fluid communication with second supply station 210' and with second pump module 230'. First inlet fluid circuit 240 comprises inlet fluid pathways which supply the first fluid (contained in first supply station 210) to first variable-volume sub-chamber 235 and to second variable-volume sub-chamber 236 so that chamber 231 is filled with a suitable volume amount of the first fluid to be delivered outside fluid delivery system 200 (arrow F). Analogously, second inlet fluid circuit 240' comprises inlet fluid pathways which supply the second fluid (contained in second supply station 210') to first variable-volume sub-chamber 235' and to second variable-volume sub-chamber 236' so that chamber 231' is filled with a suitable volume amount of the second fluid to be delivered outside fluid delivery system 200 (arrow F').

In detail, first and second inlet fluid circuits 240, 240' comprise a first inlet fluid pathway 241, 241' which is in fluid communication with supply station 210, 210', said first inlet fluid pathway 241, 241' including a supply station valve 211, 211' that allows the respective fluid to be discharged from supply station 210, 210'. Supply station valve 211, 211' is an active valve that is operated by the fluid delivery system, as it will be explained in detail in the following of the present description.

Downstream from supply station valve 211, 211', first and second inlet fluid circuits 240, 240' branch into a second inlet fluid pathway 242, 242' and a third inlet fluid pathway 243, 243' which are in fluid communication with first sub-chamber 235, 235' and second sub-chamber 236, 236', respectively. First sub-chamber 235, 235' is provided with a first inlet port 244, 244' which allows second inlet fluid pathway 242, 242' to be in fluid communication with first sub-chamber 235, 235'. Analogously, second sub-chamber 236, 236' is provided with a second inlet port 246, 246' which allows third inlet fluid pathway 243, 243' to be in fluid communication with second sub-chamber 236, 236'.

Upstream from the first inlet port 244, 244', second inlet fluid pathway 242, 242' is provided with a first inlet fluid circuit valve 245, 245' which allows the respective fluid (i.e. the first fluid exiting from first supply station 210 and the second fluid exiting from second supply station 210') to flowing into first sub-chamber 235, 235' through second inlet fluid pathway 242, 242'. According to an embodiment of the present disclosure, first inlet fluid circuit valve 245, 245' is a check valve, i.e. a one-way valve which allows the fluid to flow through it in only one direction, specifically from supply station 210, 210' towards first sub-chamber 235, 235', and avoiding that the fluid flows back towards supply station 210, 210'.

Analogously, upstream from second inlet port 246, 246', third inlet fluid pathway 243, 243' is provided with a second inlet fluid circuit valve 247, 247' which allows the respective fluid (i.e. the first fluid exiting from first supply station 210 and the second fluid exiting from second supply station 210') to flow into second sub-chamber 236, 236' through third inlet fluid pathway 243, 243'. According to an embodiment of the present disclosure, second inlet fluid circuit valve 247, 247' is a check valve, i.e. a one-way valve which prevents reverse flow, thereby allowing the fluid to flow through it in only one direction, specifically from supply station 210, 210' towards second sub-chamber 236, 236', and avoiding that the fluid flows back towards supply station 210, 210'.

Preferably, first 245, 245' and second 247, 247' inlet fluid circuit valves are ball check valves wherein a ball is present inside the body valve for regulating the fluid flow.

Fluid delivery system 200 of the present disclosure further comprises a first outlet fluid circuit 250 (which is separate from first inlet fluid circuit 240) and a second outlet fluid circuit 250' (which is separate from second inlet fluid circuit 240'). In detail, first outlet fluid circuit 250 is in fluid communication with first pump module 230, and analogously second outlet fluid circuit 250' is in fluid communication with second pump module 230'. Both first and second outlet fluid circuits 250, 250' comprise a first outlet fluid pathway 251, 251' and a second outlet fluid pathway 252, 252' that allow fluid delivery system 200 to discharge the first fluid from chamber 231 (see arrow F) and the second fluid from chamber 231' (see arrow F'), respectively. In detail, first sub-chamber 235, 235' is provided with a first outlet port 253, 253' which allows first outlet fluid pathway 251, 251' to be in fluid communication with said first sub-chamber 235, 235'. Analogously, second sub-chamber 236, 236' is provided with a second outlet port 254, 254' which allows second outlet fluid pathway 252, 252' to be in fluid communication with said second sub-chamber 236, 236'. As it will be described in detail in the following of the present disclosure, in operation first 251, 251' and second 252, 252' outlet fluid pathways of outlet fluid circuit 250, 250' alternatively discharge the first fluid from first sub-chamber 235 and from second sub-chamber 236 as well as the second fluid from first sub-chamber 235' and from second sub-chamber 236'.

Downstream from first outlet port 253, 253', first outlet fluid pathway 251, 251' is provided with a first outlet fluid circuit valve 255, 255' which allows first and second fluids to being discharged respectively from first sub-chamber 235, 235' through first outlet fluid pathway 251, 251' and from second sub-chamber 236, 236' through second outlet fluid pathway 252, 252'. According to an embodiment of the present disclosure, first outlet fluid circuit valve 255, 255' is a check valve, i.e. a one-way valve which prevents reverse flow, thereby allowing the fluid to flow through it in only one direction, specifically exiting from first sub-chamber 235, 235', and avoiding that the fluid flows back into said first sub-chamber 235, 235'.

Analogously, downstream from second outlet port 254, 254', second outlet fluid pathway 252, 252' is provided with a second outlet fluid circuit valve 256, 256' which allows first and second fluids to being discharged, respectively, from second sub-chamber 236, 236' through second outlet fluid pathway 252, 252'. According to an embodiment of the present disclosure, second outlet fluid circuit valve 256, 256' is a check valve, i.e. a one-way valve which allows the fluid to flow through it in only one direction, specifically exiting from second sub-chamber 236, 236', thereby avoiding that the fluid flows back into said second sub-chamber 236, 236'.

Preferably, first 255, 255' and second 256, 526' outlet fluid circuit valves are spring loaded check valves wherein a spring component is used to support valve operation by eliminating the effect of gravity on the check valve function. More preferably, first 255, 255' and second 256, 256' outlet fluid circuit valves are spring loaded ball check valves.

According to the embodiment shown in FIG. 5, fluid delivery system 200 of the present disclosure further comprises a first recirculation fluid circuit 260 and a second recirculation fluid circuit 260', said recirculation fluid circuits being also indicated in the present description as additional fluid circuits (i.e. additional fluid circuits with respect to inlet and outlet fluid circuits mentioned above). In detail, first recirculation fluid circuit 260 fluidically connects first and second variable-volume sub-chambers 235, 236 of chamber 231 of first pump module 230, said first recirculation fluid circuit 260 cooperating with a first actuator 270 (possessed by said first recirculation fluid circuit 260) for managing the passage of the first fluid in both directions between said first and second variable-volume sub-chambers 235, 236. Analogously, second recirculation fluid circuit 260' fluidically connects first and second variable-volume sub-chambers 235', 236' of chamber 231' of second pump module 230', said second recirculation fluid circuit 260' cooperating with a second actuator 270' (possessed by said second recirculation fluid circuit 260') for managing the passage of the second fluid in both directions between said first and second variable-volume sub-chambers 235', 236'.

According to the embodiment shown in FIG. 5, first and second recirculation fluid circuits 260, 260' are external to chambers 231, 231' and they fluidically connect, respectively, separate branches of first and second inlet fluid circuits 240, 240' upstream from the inlet ports 244, 244' and 246, 246' of respective sub-chambers 235, 235' and 236, 236'. In detail, with reference to first pump module 230, a first axial end 261 of first recirculation fluid circuit 260 fluidically connects with second inlet fluid pathway 242 of first inlet fluid circuit 240 downstream from first inlet fluid circuit valve 245 thereof, while a second axial end 262 of first recirculation fluid pathway 260 fluidically connects with third inlet fluid pathway 243 of first inlet fluid circuit 240 downstream from second inlet fluid circuit valve 247 thereof. Analogously, with reference to second pump module 230', a first axial end 261' of second recirculation fluid circuit 260' fluidically connects with second inlet fluid pathway 242' of second inlet fluid circuit 240' downstream from first inlet fluid circuit valve 245' thereof, while a second axial end 262' of second recirculation fluid circuit 260' fluidically connects with third inlet fluid pathway 243' of second inlet fluid circuit 240' downstream from second inlet fluid circuit valve 247' thereof.

First and second actuators 270, 270' are active valves that are operated by fluid delivery system 200, as it will be explained in detail in the following of the present description. Preferably, first and second actuators 270, 270' are electro-mechanical driven valves that are automatically controlled and operated by a processor or control unit P of fluid delivery system 200. As schematically shown in the figures, processor P controls and operates first and second actuators 270, 270', driving unit M as well as first and second supply station valves 211, 211'.

Figure 6:
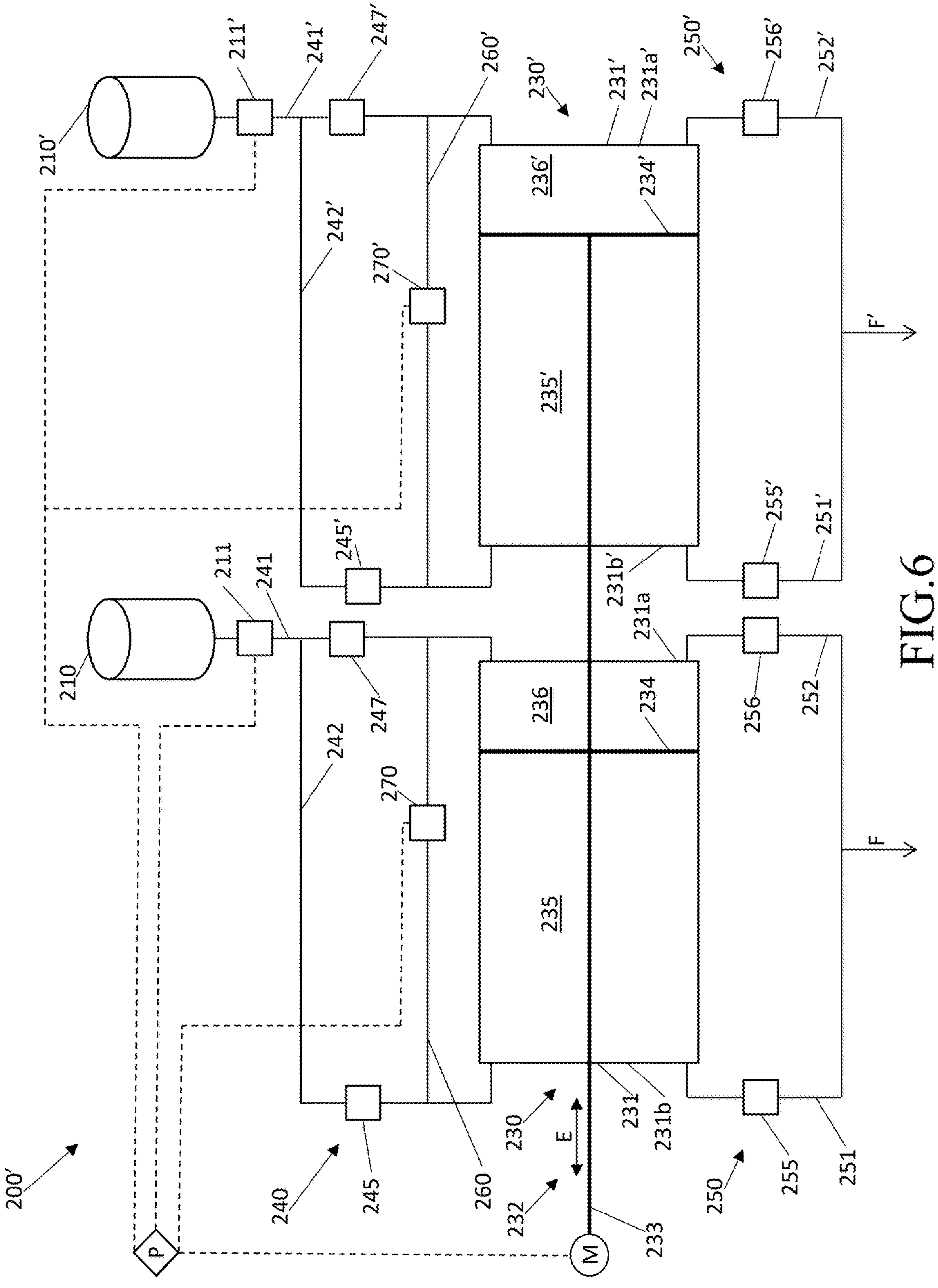
FIG. 6 shows a schematic representation of a further alternative fluid delivery system to which an embodiment of the present disclosure can be applied.

According to an alternative embodiment shown in FIG. 6, a fluid delivery system 200' is schematically represented in which said two pump modules 230, 230' are arranged in series and not in parallel as shown in the embodiment of FIG. 5. In this alternative embodiment the two chambers 231, 231' are separate and spaced apart from each other, while a common piston rod 233 with two spaced apart plungers 234, 234' is provided to said chambers 231, 231', thereby defining respective first 235, 235' and second 236, 236' variable-volume sub-chambers. All the remaining components (as well as functioning thereof) of said alternative embodiment are identical to respective components of fluid delivery system 100 shown in FIG. 5 and thus are indicated with same reference numbers.

Operation of said alternative fluid delivery system represented in FIG. 6 according to the present disclosure will be illustrated in the following with reference to applications related to the medical field, more specifically to alternate or simultaneous injection of a contrast agent and a saline solution for diagnostic purposes. However, as already mentioned above in the present description, a fluid delivery system according to the present disclosure can be used in other technological areas not correlated to medical/healthcare applications. Moreover, the general operational principles—that will be illustrated herein below with reference to some embodiments of the delivery system of the present disclosure—are applicable to the plurality of embodiments disclosed in the present description and/or shown in the figures correlated thereto.

Figure 7:
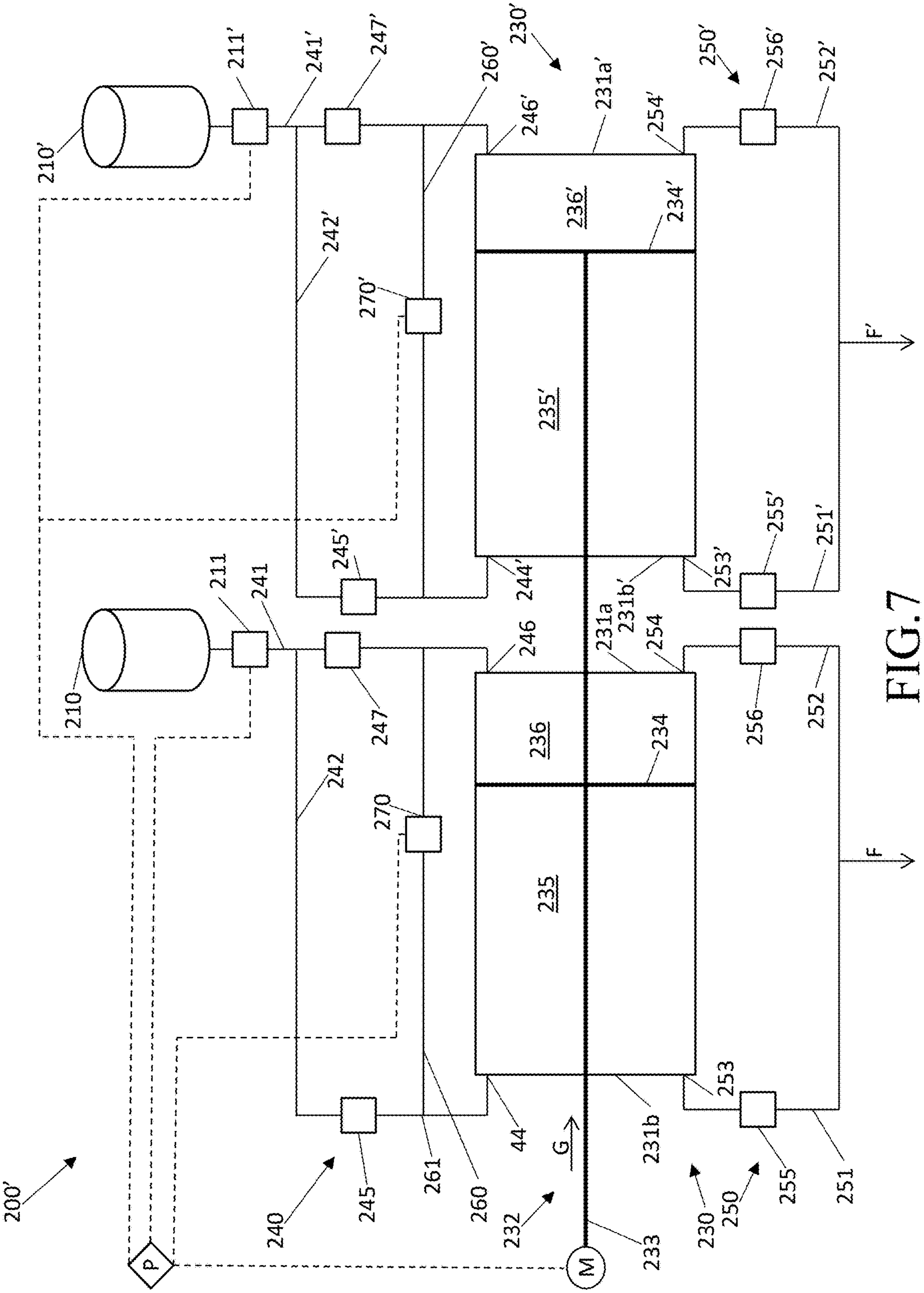
FIG. 7 and FIG. 8 show a schematic representation of the operation steps of the fluid delivery system shown in FIG. 6.
Figure 8:
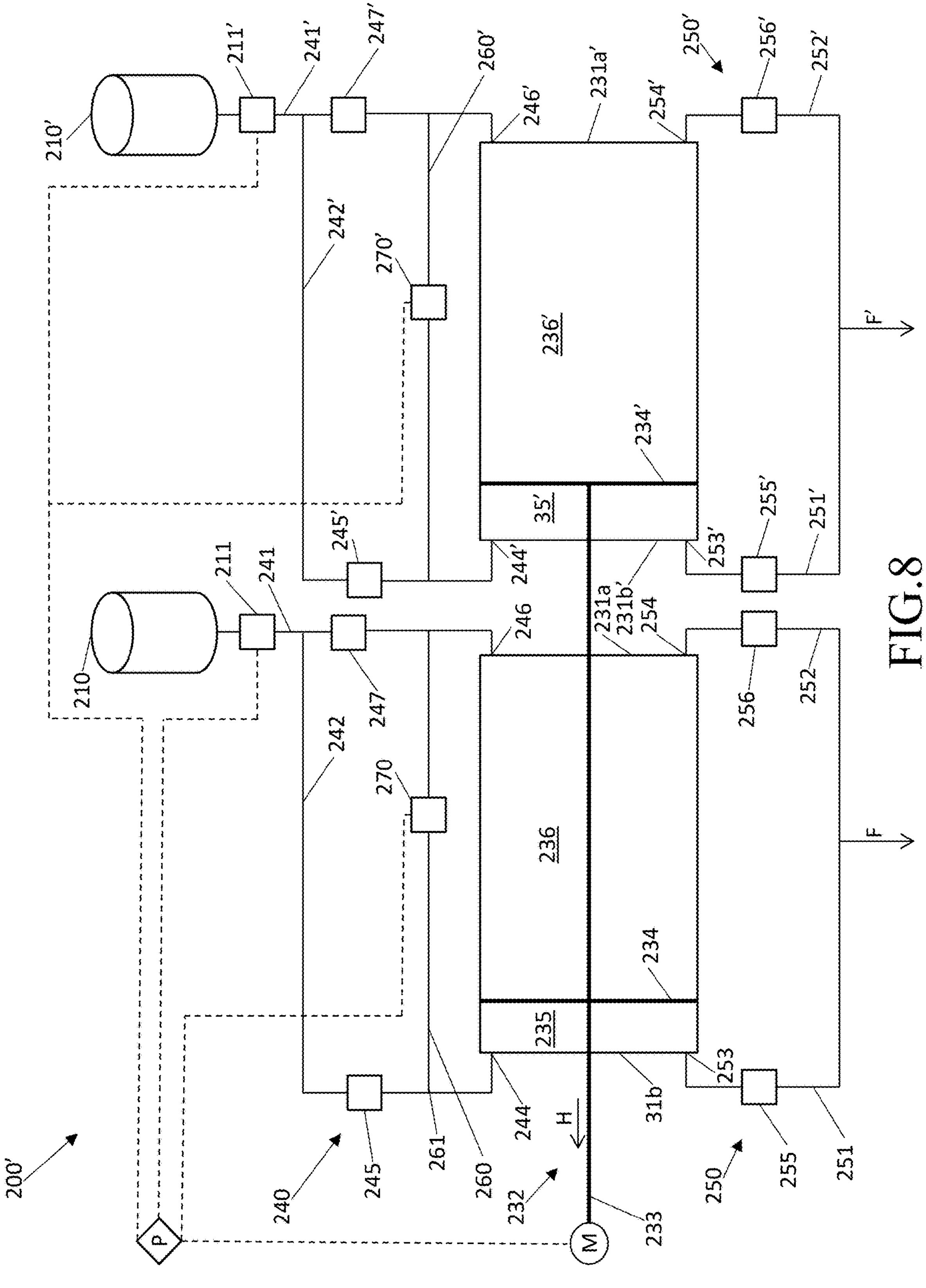

As an example of a method of operating said alternative fluid delivery system according to the present disclosure, reference is made to FIG. 7 and FIG. 8 in which fluid delivery system 200' according to the embodiment shown in FIG. 6 is exemplified.

Supply station 210 contains a first fluid (not shown), for instance a contrast agent, which is requested to be injected to a patient by delivery system 200' (see arrow F), while supply station 210' contains a second fluid (not shown), for instance a saline solution, which is requested to be injected to the patient by said delivery system 200' (see arrow F'). Typically, first fluid exiting at F and second fluid exiting at F' are conveyed to the patient through a common tubing (patient line—not shown) which is mechanically and fluidically connected to a catheter and/or a needle for accessing patient's vasculature.

As a first initiation step, the method of delivery according to the present disclosure comprises the step of filling first and second sub-chambers 235, 236 of first pump module 230 with the first fluid and, analogously, the step of filling first and second sub-chambers 235', 236' of second pump module 230' with the second fluid. In order to perform said filling steps, processor P opens supply station valves 211, 211', it closes actuators 270, 270' of first and second recirculation fluid circuits 260, 260' and it acts on driving unit M for reciprocating common piston 232 within chambers 231, 231', thereby allowing the first and the second fluids to exit supply stations 210, 210' respectively, and to flow through first inlet fluid circuit 240 and through second inlet fluid circuit 240'. In detail, as soon as piston 232 is axially translated along a first direction (e.g. arrow G of FIG. 7), under-pressure is generated in the first sub-chambers (e.g. sub-chambers 235, 235') which are increasing their volume due to the piston axial movement. Therefore, the respective fluids are allowed to flow through first 241, 241' and second 242, 242' of first and second inlet fluid circuits 240, 240', through the corresponding first inlet fluid circuit valves (e.g. first inlet fluid circuit valves 245, 245'), and then they enter and fill said first sub-chambers. At the same time, the air contained within the second sub-chambers (e.g. sub-chambers 236, 236')—which are decreasing their volume due to the piston axial movement (arrow G)—is primed away from the fluid delivery system through venting means possessed by the opposite second inlet fluid circuit valves (e.g. second inlet fluid circuit valves 247, 247'). In fact, the air contained in said first sub-chambers 235, 235' is generally forced to exit said sub-chambers by passing through first inlet ports 244, 244', then through second inlet fluid pathways 242, 242' and finally through said first inlet fluid circuit valves 245, 245'. Successively, in order to fill the second sub-chambers with the respective fluids and to prime the first sub-chambers (i.e. expelling air therefrom), processor P acts on driving unit M for inverting the piston movement so that the piston is axially translated along a second direction opposite to the first direction (e.g. arrow H of FIG. 8). Since actuators 270, 270' are kept closed while the piston is moving during the filling and priming steps, under-pressure is generated in the second sub-chambers (e.g. sub-chambers 236, 236') which are increasing their volume due to the piston axial movement (arrow H). Therefore, the first and second fluids are allowed to flow through first 241, 241' and third 243, 243' inlet fluid pathways of first and second inlet fluid circuits 240, 240' respectively, through the corresponding second inlet fluid circuit valves (e.g. second inlet fluid circuit valves 247, 247'), and then they enter and fill said second sub-chambers. At the same time, the air still contained within the first sub-chambers (e.g. sub-chambers 235, 235')—which are decreasing their volume due to the piston axial movement (arrow H)—is primed away from the fluid delivery system through venting means possessed by the corresponding first inlet fluid circuit valves (e.g. first inlet fluid circuit valves 245, 245'). In fact, the air contained in said second sub-chambers 236, 236' is generally forced to exit said sub-chambers by passing through second inlet ports 246, 246', then through third inlet fluid pathways 243, 243' and finally through second inlet fluid circuit valves 247, 247'. During the priming steps some amounts of the first fluid and of the second fluid exit from the fluid delivery system through first 250 and second 250' outlet fluid circuits, so that priming of also said first 250 and second 250' outlet fluid circuits can be suitably performed.

Alternatively, air priming of the fluid delivery system is performed by dedicated venting means (not shown in the drawings) which is separate from the fluid circuit valves. According to an alternative embodiment, a dedicated venting means is associated with each valve of the fluid delivery system. According to a further alternative embodiment, a dedicated venting means is associated with each actuator 270, 270' of first and second recirculation fluid circuits 260, 260'.

As soon as chambers 231, 231' are filled up with the first fluid and the second fluid, respectively, and priming of the fluid delivery system is completed, processor P closes supply station valves 211, 211' and it opens actuators 270, 720' of first and second recirculation fluid circuits 260, 260', while driving unit M is still operated, thereby keeping piston 232 axially translating (arrows G and H) within chambers 231, 231'. Alternatively, processor P opens actuators 270, 270' of first and second recirculation fluid circuits 260, 260' while supply station valves 211, 211' are kept in their open working state when the two fluids are recirculated inside their respective chambers 231, 231'.

By keeping actuators 270, 270' of first and second recirculation fluid circuits 260, 260' in their open working state, fluid delivery system 200' is prevented from delivering the first and the second fluids outside thereof. In fact, thanks to the open working state of actuators 270, 270' and to the axial translation of piston 232, the first fluid is continuously recirculated within first chamber 231 through first recirculation fluid circuit 260, while the second fluid is continuously recirculated within second chamber 231' through second recirculation fluid circuit 260'. In detail, when piston 232 is moved in a first direction (e.g. arrow G of FIG. 7), the first fluid contained in second sub-chamber 236 is pushed through second inlet port 246 thereof and then through first recirculation fluid circuit 260 and through first actuator 270 to enter first sub-chamber 235 at first inlet port 244 thereof. At the same time, the second fluid contained in second sub-chamber 236' is pushed through second inlet port 246' thereof and then through second recirculation fluid circuit 260' and through second actuator 270' to enter first sub-chamber 235' at first inlet port 244' thereof.

Thereafter, when piston 232 has reached its first end-stop, i.e. plunger 234 has completed its axial translation in said first direction (right direction of FIG. 7—see arrow G) and it has arrived in proximity of base wall 231*a* of chamber 231 and, simultaneously, plunger 234' has arrived in proximity of base wall 231*a'* of chamber 231', processor P acts on driving unit M to reverse piston axial translation (left direction of FIG. 8—see arrow H). Analogously to the piston first run described above, the first fluid contained in first sub-chamber 235 is pushed through first inlet port 244 thereof and then through first recirculation fluid circuit 260 and through first actuator 270 to enter second sub-chamber 236 at second inlet port 246 thereof. At the same time, the second fluid contained in first sub-chamber 235' is pushed through first inlet port 244' thereof and then through second recirculation fluid circuit 260' and through second actuator 270' to enter second sub-chamber 236' at second inlet port 246' thereof.

Then, as soon as piston 232 has reached its second end-stop, i.e. plungers 234, 234' have completed their axial translations in the second direction (left direction in FIG. 8—see arrow H) and they arrive in proximity of base walls 231*b*, 231*b'* of respective chambers 231, 231' (so that first sub-chambers 235, 235' contain a substantially small volume of respective fluids while second sub-chamber 236, 236' contain a large volume of respective fluids), processor P acts on driving unit M to reverse again piston axial translation (right direction in FIG. 7—see arrow G), thereby starting a new charge/discharge cycle of chambers 231, 231' of fluid delivery system 200'. Of course, any number of cycles can be arranged for, said number depending on the requirements of the specific fluids to be delivered and on the specific application in which the fluid delivery system is implemented. As already mentioned above, said initial recirculating steps of the two fluids within their respective chambers are particularly advantageous since they allow keeping the two fluids moving within the fluid delivery system, thereby ensuring proper and homogeneous shaking of each single fluid before delivery thereof.

It has to be pointed out that the fluids contained in second sub-chambers 236, 236' and pushed by plungers 234, 234' are allowed neither to flowing back into supply stations 210, 210' nor to accessing second outlet fluid pathways 252, 252' of first and second outlet fluid circuits 250, 250'. In fact, preferably supply station valves 211, 211' are closed and, moreover, both first 245, 245' and second 247, 247' inlet fluid circuit valves are one-way valves which allow the fluids flowing from supply stations 210, 210' into respective chambers 231, 231', but not vice versa, thereby avoiding the fluids discharged from first 235, 235' and second 236, 236' sub-chambers to flowing back through first 241, 241' and second 242, 242' inlet fluid pathways of first and second inlet fluid circuits 240, 240'. Moreover, since first 255, 255' and second 256, 256' outlet fluid circuit valves automatically open only when the fluids discharged respectively from first 235, 235' and second 236, 236' sub-chamber have a sufficiently high pressure for overcoming the internal resilience of said valves (preferably, first and second outlet fluid circuit valves are ball spring-loaded check valves), when actuators 270, 270' are in the open state the fluids discharged from first 235, 235' and second 236, 236' sub-chambers do not have enough force to overcome the internal resilience of first 255, 255' and second 256, 256' outlet fluid circuit valves, and thus the fluids are not delivered outside of fluid delivery system 200', but they are recirculated inside their respective sub-chambers.

It is apparent from the above that said alternative embodiment of the fluid delivery system of the present disclosure allows a continuous and predefined movement (e.g. in terms of volumes, piston translational speed) of one fluid or both fluids before exiting the fluid delivery system. As already mentioned above, this aspect of the present disclosure is particularly advantageous in case a specific fluid property (e.g. composition homogeneity, temperature, viscosity, mixture, fluidity) is requested to be achieved and/or maintained before starting delivery of that fluid. In fact, the fluid delivery system according to the present disclosure allows the fluids introduced into first 231 and second 231' chambers to be continuously recirculated by being alternately charged/discharged between first 235, 235' and second 236, 236' sub-chambers when fluid delivery system 200' is not delivering, i.e. the fluids are not definitely exiting the fluid delivery system. Thanks to first 260 and second 260' recirculation fluid circuits, and first 270 and second 270' actuators associated thereto, recirculation of the fluids and redistribution thereof between the two sub-chambers contributes in balancing the pressure therein. This aspect is particularly advantageous since it allows to operate the system at a limited (low) pressure, at least in the initial stage when the delivery system is not yet delivering the fluids outside the system, thereby limiting the technical constraints which would need to be implemented if the system were required to operate at higher pressure values.

As soon as recirculation is completed (e.g. the desired homogeneity of one fluid or of both fluids is successfully reached and, at a certain point in time, the delivery of the first fluid and/or of the second fluid is requested to be started), processor P suitably acts on first or second actuators 270, 270' to close it/them and to stop the recirculation step of at least one of said first and second fluids.

For example, in case the first fluid contained within supply station 210 is requested to be delivered first, processor P closes first actuator 270 of first recirculation fluid circuit 260, while second actuator 270' of second recirculation fluid circuit 260' is still kept in its open working condition so that delivery (arrow F) of the first fluid can be performed while the second fluid is kept recirculating inside its respective chamber 231'. This is the case, for instance, in which at a given time of an injection/infusion process performed on a given patient undergoing an examination procedure (e.g. a CT diagnostic examination), fluid delivery system 200' is requested to deliver only the first fluid (e.g. contrast agent) contained within supply station 210, while recirculation of the second fluid (e.g. saline solution) is performed (i.e. the second fluid is not delivered outside of the fluid delivery system at that moment in time).

Therefore, the method of delivery according to the present disclosure comprises the step of starting delivery (i.e. outside of the fluid delivery system) of the first fluid contained within first chamber 231. In order to perform said step, as mentioned above processor P closes first actuator 270 of first recirculation fluid circuit 260 and it opens first supply station valve 211. During delivery of the first fluid (fluid exiting the fluid delivery system—see arrow F), first supply station valve 211 is maintained in its open state because it is important to refill sub-chambers 235, 236 of first chamber 231 with new first fluid in order to avoid fluidic perturbations possibly impacting on the correct functioning of the piston and, consequently, of the overall fluid delivery system. Since closing first actuator 270 prevents first fluid from flowing through first recirculation fluid circuit 260 (while, as already mentioned above, first and second inlet fluid circuit valves 245, 247 do not allow any flow back of the first fluid towards first supply station 210), pushing first plunger 234 in the first direction (arrow G of FIG. 7) and in the second opposite direction (arrow H of FIG. 8) allows the first fluid to exit, respectively, second outlet port 254 and first outlet port 253 of first chamber 231. Therefore, when the first fluid is pushed to pass through second outlet port 254 (arrow G), the first fluid flows into second outlet fluid pathway 252 of first outlet fluid circuit 250 and then it passes through second outlet fluid circuit valve 256 because at this stage of the procedure, since first actuator 270 is closed, the fluid pressure is sufficiently high to overcome the internal resilience of said second outlet fluid circuit valve 256. Analogously, when the first fluid is pushed to pass through first outlet port 253 (arrow H), the first fluid flows into first outlet fluid pathway 251 of first outlet fluid circuit 250 and then it passes through first outlet fluid circuit valve 255 because at this stage of the procedure, since first actuator 270 is closed, the fluid pressure is sufficiently high to overcome the internal resilience of said first outlet fluid circuit valve 255. Consequently, the first fluid is finally delivered (arrow F) by sequentially discharging it from first and second sub-chambers 235, 236 of first chamber 231. In fact, since first and second outlet fluid circuit valves 255, 256 are one-way valves, the first fluid cannot flow back through the under-pressurized pathway and thus it is necessarily forced to be delivered (arrow F).

It can be pointed out that the method of delivery according to the present disclosure does not necessarily require that sub-chambers 235, 236 are fully filled with the first fluid or that they are fully discharged of the first fluid. In other words, it is not mandatory that, during its back and forth axial translations, first plunger 234 reaches base walls **231*a*, 231*b* of first chamber 231. This means that the method of delivery according to the present disclosure can comprise partial charging/discharging steps of the first fluid into/from the respective sub-chambers of the first chamber, especially in case a defined (and typically small) volume of first fluid is requested to be delivered in one shot (i.e. along a single translational movement of the first plunger without reversing thereof). Of course, this aspect mentioned above can analogously apply also to sub-chambers 235', 236' of second chamber 231'**.

As mentioned above, during the step of delivering the first fluid (arrow F), first supply station valve 211 is kept open so that new first fluid can alternately enter the two sub-chambers of the first chamber and undesired perturbations effects would not occur while the piston is axially translating within said first chamber 231. Even though the new first fluid entering the system during the step of delivering has not passed through first actuator 270 and first recirculation fluid circuit 260, it can be noted that the new first fluid is not instantly delivered. In fact, the new first fluid enters the under-pressurized sub-chamber, while the first fluid that is delivered by the system is the one contained in the pressurized sub-chamber. Therefore, before being delivered, the new first fluid is permanently moving and mixing within the respective sub-chamber thanks to the piston axial translation, thereby ensuring that the desired delivery conditions are reached before finally exiting the system.

As already mentioned above, the Applicant has found that recirculation of the first fluid within first chamber 231, by letting the first fluid flowing through first recirculation fluid circuit 260 and first actuator 270 associated thereto, can remarkably reduce or even completely remove the risk of pressure pulsations when the first fluid is being delivered, especially at the beginning of the fluid delivery procedure. Indeed, the fluid delivery system according to the present disclosure can properly control pressure drops or pressure spikes, occurring when piston 232 starts moving, thanks to the presence of first recirculation fluid circuit 60 and first actuator 270. In fact, according to the present disclosure, the fluid delivery system starts delivering the first fluid (outside of the fluid delivery system—arrow F) when recirculation of the first fluid inside first chamber 231 has already begun, therefore delivery will start when the piston is already moving inside first chamber 231. This clearly means that the start of fluid delivery is not simultaneous with the start of piston movement since delivery of the first fluid is started when the piston is already axially translating within first chamber 231 for allowing the first fluid recirculation step to be performed.

Furthermore, as already mentioned above, the Applicant has also found that recirculation of the first fluid within first chamber 231, by letting the first fluid flowing through first recirculation fluid circuit 260 and first actuator 270 associated thereto, can remarkably reduce or even completely eliminate the latency time of the fluid delivery system. The latency time is the technical time which the fluid delivery system inevitably requires in order to be ready to deliver the fluid. In fact, as soon as processor P instructs to deliver electric current to driving unit M, typically said electric current builds up an electromagnetic field which acts on rotor magnets that generate a torque on the gears, thereby causing the piston to start its movement. When the piston starts moving, fluid pressure starts building up and it still needs some additional time to reach and overcome the pressure threshold value which is set up for first and second outlet fluid circuit valves 255, 256. The sum of all these times is called "latency time" and it is far from being negligible, thereby inevitably causing a delay in fluid delivery out of the fluid delivery system. Thanks to the presence of first recirculation fluid circuit 260 and first actuator 270 associated thereto, fluid delivery system 200' of the present disclosure can overcome or reduce said latency time since, in order to perform recirculation of the first fluid within first chamber 231, piston 232 starts moving well in advance to fluid delivery. Therefore, as soon as processor P closes first actuator 270 for starting delivery of the first fluid (arrow F), the fluid pressure immediately increases and very quickly overcomes the pressure threshold value which is set up for first and second outlet fluid circuit valves 255, 256. Consequently, the first fluid is delivered by the system very soon after processor P has ordered to start delivering.

As soon as delivery of the first fluid (e.g. contrast agent) contained within first supply station 210 is requested to be terminated and delivery of the second fluid (e.g. saline solution) contained within second supply station 210' is requested to be started, processor P opens first actuator 270 of first recirculation fluid circuit 260 and it closes second actuator 270' of second recirculation fluid circuit 260' so that delivery (arrow F') of the second fluid is performed while the first fluid is recirculated inside its respective chamber 231.

Therefore, the method of delivery according to the present disclosure further comprises the step of starting delivery (i.e. outside of the fluid delivery system) of the second fluid contained within first chamber 231'. In order to perform said step, as mentioned above processor P closes second actuator 270' of second recirculation fluid circuit 260' and it opens second supply station valve 211'. During delivery of the second fluid (fluid exiting the fluid delivery system—see arrow F'), second supply station valve 211' is maintained in its open state because it is important to refill sub-chambers 235', 236' of second chamber 231' with new second fluid in order to avoid fluidic perturbations possibly impacting on the correct functioning of the piston and, consequently, of the overall fluid delivery system. Since closing second actuator 270' prevents second fluid from flowing through second recirculation fluid circuit 260' (while, as already mentioned above, first and second inlet fluid circuit valves 245', 247' do not allow any flow back of the second fluid towards second supply station 210'), pushing second plunger 234' in the first direction (arrow G of FIG. 7) and in the second opposite direction (arrow H of FIG. 8) allows the second fluid to exiting, respectively, second outlet port 254' and first outlet port 253' of second chamber 231'. Therefore, when the second fluid is pushed to pass through second outlet port 254' (arrow G), the second fluid flows into second outlet fluid pathway 252' of second outlet fluid circuit 250' and then it passes through second outlet fluid circuit valve 256' because at this stage of the procedure, since second actuator 270' is closed, the fluid pressure is sufficiently high to overcome the internal resilience of said second outlet fluid circuit valve 256'. Analogously, when the second fluid is pushed to pass through first outlet port 253' (arrow H), the second fluid flows into first outlet fluid pathway 251' of second outlet fluid circuit 250' and then it passes through first outlet fluid circuit valve 255' because at this stage of the procedure, since second actuator 270' is closed, the fluid pressure is sufficiently high to overcome the internal resilience of said first outlet fluid circuit valve 255'. Consequently, the second fluid is finally delivered (arrow F') by sequentially discharging it from first and second sub-chambers 235', 236' of second chamber 231'. In fact, since first and second outlet fluid circuit valves 255', 256' are one-way valves, the second fluid cannot flow back through the under-pressurized pathway and thus it is necessarily forced to be delivered (arrow F').

As mentioned above, the present disclosure relates to a modular fluid delivery system comprising at least one disposable pump module assembly. In detail, in order to better adjusting to the many and various customers' needs, the modular fluid delivery system according to the present disclosure may have one or more disposable pump module assemblies and each disposable pump module assembly may have one or more fluid circuits as specified in the following of the present description.

Figure 9:
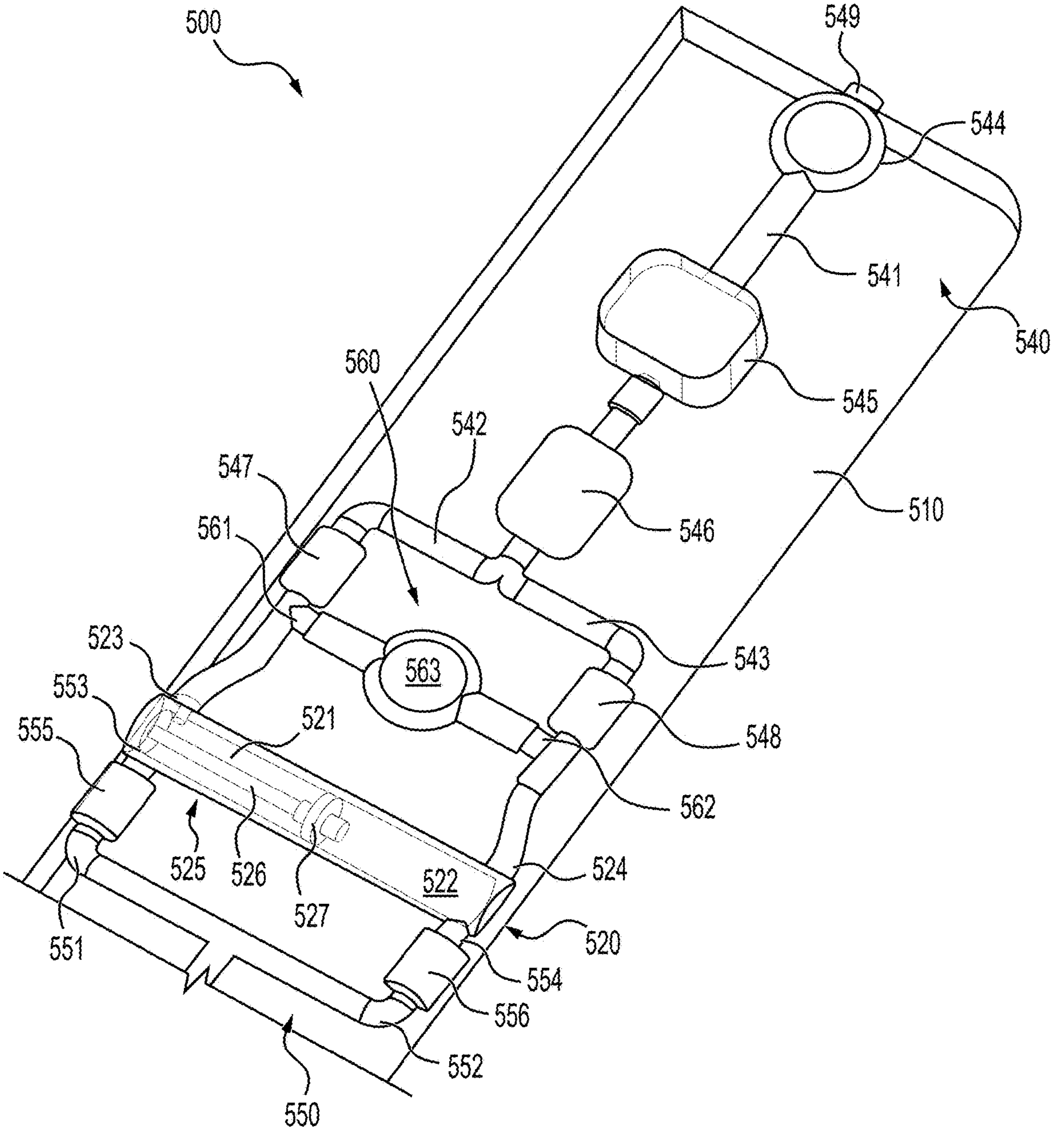
FIG. 9 shows a partially transparent perspective view of an embodiment of a disposable pump module of the present disclosure in which a single fluid circuit pathway is envisaged.

FIG. 9 shows a perspective view of a first embodiment of a disposable pump module 500 of a modular fluid delivery system according to the present disclosure. Disposable pump module 500 comprises only one single fluid circuit pathway (as better detailed herein below) and it represents the simplest pump module solution which can be used in a modular fluid delivery system of the present disclosure, for example according to fluid delivery system 100 schematically shown in FIG. 1 and already disclosed in detail herein above. Disposable pump module 500 comprises a supporting element 510 which includes at least the following components: a chamber 520, an inlet fluid circuit pathway 540 entering said chamber, an outlet fluid circuit pathway 550 exiting from said chamber and a recirculation fluid circuit pathway 560 connecting two separate opposite branches of said inlet fluid circuit pathway 540. Typically, supporting element 510 is obtained by associating together (e.g. by UV gluing, thermal gluing, solvent bonding, US welding, laser welding, spin welding) two distinct layers, each layer being provided with suitably sized recesses which form the above components once the two layers are integrally engaged together. Therefore, the so formed components result in being fully embedded within the supporting element thickness. Preferably, said layers are molded plastic layers.

Figure 13:
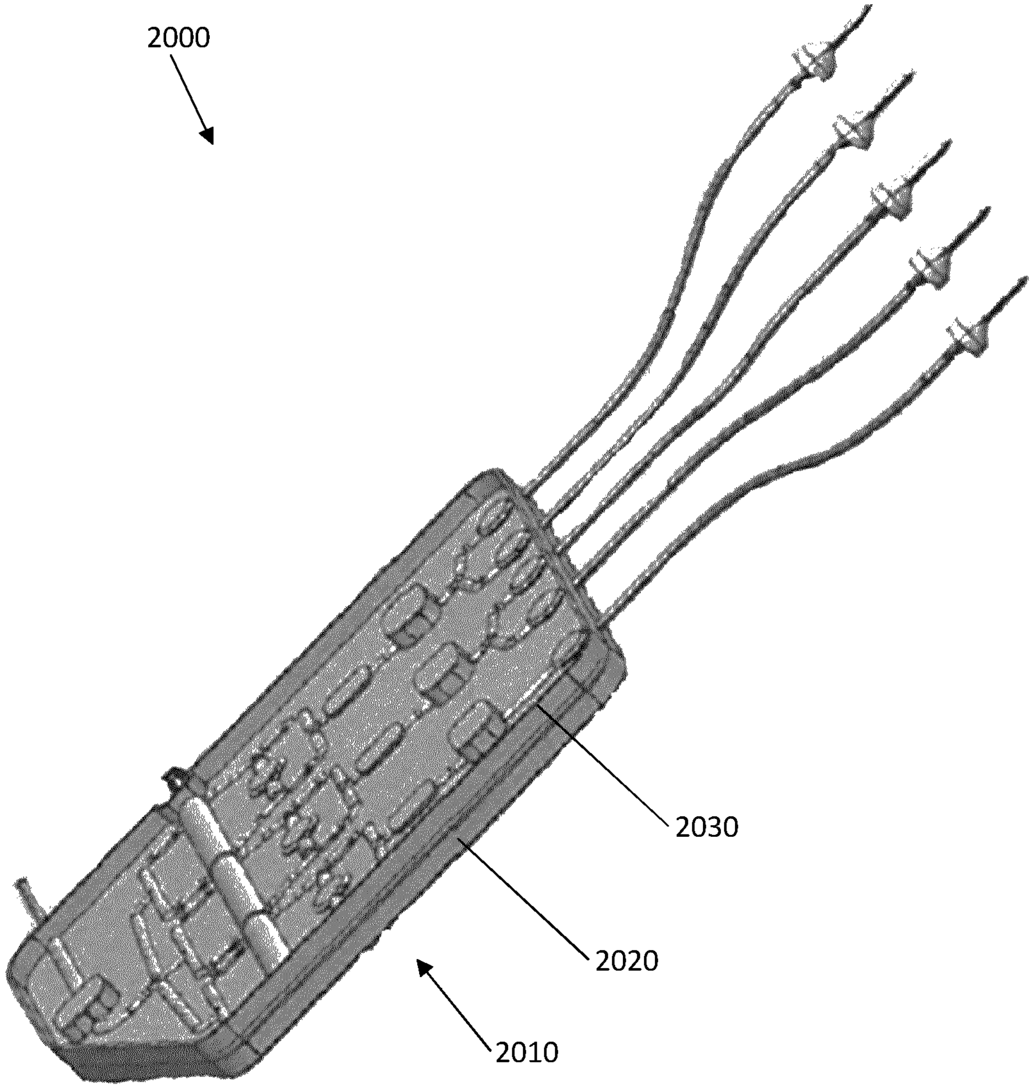
FIG. 13 and FIG. 14 show perspective views of a further embodiment of a disposable pump module assembly of the present disclosure in which three distinct fluid circuits pathways are envisaged.

As a further clarification, said two separate layers are not completely visible in FIG. 9, but they are clearly shown in FIG. 13, for instance. In fact, FIG. 9 shows the disposable pump module with some transparency indicating the presence of the second bottom layer positioned below the first layer, the latter being clearly visible in the foreground.

Inlet fluid circuit pathway 540 is in fluid communication with a fluid supply station (not shown in FIG. 9) and with chamber 520. In detail, inlet fluid circuit pathway 540 comprises a first inlet pathway 541 which successively branches into a second inlet pathway 542 and a third inlet pathway 543 that are in fluid communication, respectively, with a first sub-chamber 521 and a second sub-chamber 522 of chamber 520. In fact, disposable pump module 500 further comprises a piston 525 which is reciprocated (i.e. moved back and forth by a driving unit M—not shown in FIG. 9) within chamber 520. Piston 525 comprises a piston rod 526 and a plunger 527, the plunger being arranged to be substantially perpendicular to the piston rod and having a radial extension which substantially corresponds to the chamber width. Therefore, in cooperation with internal walls of chamber 520, plunger 527 defines said first variable-volume sub-chamber 521 on one side of the plunger (e.g. on the left side of the plunger in the embodiment of FIG. 9) and a second variable-volume sub-chamber 522 on the opposite side of the plunger (e.g. on the right side of the plunger in the embodiment of FIG. 9).

First inlet pathway 541 further comprises a first seat 544 for receiving a supply station valve (not shown in FIG. 9) that allows the fluid to be suitably discharged from the supply station. The supply station valve is an active valve that is directly operated by a processor P of the fluid delivery system, as previously explained for instance with reference to FIG. 1.

Preferably, the supply station valve is not part of disposable pump module 500 and, typically, it is a component possessed by the modular fluid delivery system. For instance, in case the modular fluid delivery system is a powered injector suitable for being used in the medical field, the supply station valve is typically received within the injector head.

Alternatively, the supply station valve is part of disposable pump module 500 and it is received within first seat 544 of supporting element 510.

Typically, first inlet pathway 541 further comprises a second seat 545 for receiving an air bubble detector (not shown in FIG. 9) which is possessed by the modular fluid delivery system (and thus it is not part of disposable pump module 500) and which is used for detecting the presence of air bubbles possibly contained in the fluid discharged from the supply station. The air bubble detector can be of any type known in the art, e.g. an ultrasonic or a capacitive sensor.

First inlet pathway 541 further comprises a third seat 546 for receiving a filtering unit (not shown in FIG. 9) which can be used, if necessary, for guaranteeing absence of impurities or any additional substance which should not be contained in the fluid(s) to be delivered. The filtering unit is an optional component and the presence thereof depends on the fluid(s) nature/characteristics.

Downstream from third seat 546, first inlet pathway 541 branches into second inlet pathway 542 and third inlet pathway 543 which are in fluid communication with first sub-chamber 521 and second sub-chamber 522, respectively. First sub-chamber 521 is provided with a first inlet port 523 which allows second inlet pathway 542 to be in fluid communication with first sub-chamber 521. Analogously, second sub-chamber 522 is provided with a second inlet port 524 which allows third inlet pathway 543 to be in fluid communication with second sub-chamber 522.

Upstream from first inlet port 523, second inlet pathway 542 is provided with a seat 547 for receiving a first inlet fluid circuit valve (not shown in FIG. 9) which allows the fluid to flowing into first sub-chamber 521 through second inlet pathway 542. According to an embodiment of the present disclosure, first inlet fluid circuit valve is a check valve, i.e. a one-way valve which allows the fluid to flow through it in only one direction, specifically from the supply station towards first sub-chamber 521, thereby avoiding that the fluid flows back towards the supply station.

Analogously, upstream from second inlet port 524, third inlet pathway 543 is provided with a seat 548 for receiving a second inlet fluid circuit valve (not shown in FIG. 9) which allows the fluid to flowing into second sub-chamber 522 through third inlet pathway 543. According to an embodiment of the present disclosure, second inlet fluid circuit valve is a check valve, i.e. a one-way valve which prevents reverse flow allowing the fluid to flow through it in only one direction, specifically from the supply station towards second sub-chamber 522, thereby avoiding that the fluid flows back towards the supply station.

Preferably, first and second inlet fluid circuit valves are ball check valves in which a ball is present inside the body valve for regulating the fluid flow.

As mentioned above, disposable pump module 500 further comprises outlet fluid circuit pathway 550 which is separate from inlet fluid circuit pathway 540. Outlet fluid circuit pathway 550 is in fluid communication with chamber 520 and it comprises a first outlet pathway 551 and a second outlet pathway 552 for discharging the fluid from chamber 520. In detail, first sub-chamber 521 is provided with a first outlet port 553 which allows first outlet pathway 551 to be in fluid communication with first sub-chamber 521. Analogously, second sub-chamber 522 is provided with a second outlet port 554 which allows second outlet pathway 552 to be in fluid communication with second sub-chamber 522. As already described above with reference to FIG. 1, in operation first and second outlet pathways 551, 552 of outlet fluid circuit pathway 550 discharge the fluid alternatively from first sub-chamber 521 and from second sub-chamber 522.

Downstream from first outlet port 553, first outlet pathway 551 is provided with a seat 555 for receiving a first outlet fluid circuit valve (not shown in FIG. 9) which allows the fluid to being discharged from first sub-chamber 521 through first outlet pathway 551. According to an embodiment of the present disclosure, the first outlet fluid circuit valve is a check valve, i.e. a one-way valve which prevents reverse flow allowing the fluid to flow through it in only one direction, specifically exiting from first sub-chamber 521, thereby avoiding that the fluid flows back into said first sub-chamber 521.

Analogously, downstream from second outlet port 554, second outlet pathway 552 is provided with a seat 556 for receiving a second outlet fluid circuit valve (not shown in FIG. 9) which allows the fluid to being discharged from second sub-chamber 522 through second outlet pathway 552. According to an embodiment of the present disclosure, the second outlet fluid circuit valve is a check valve, i.e. a one-way valve which allows the fluid to flow through it in only one direction, specifically exiting from second sub-chamber 522, thereby avoiding that the fluid flows back into said second sub-chamber 522.

Preferably, first and second outlet fluid circuit valves are spring loaded check valves wherein a spring component is used to support valve operation by eliminating the effect of gravity on the check valve function. More preferably, first and second outlet fluid circuit valves are spring loaded ball check valves.

According to the present disclosure, disposable pump module 500 further comprises a recirculation fluid circuit pathway 560 fluidically connecting said first and second variable-volume sub-chambers 521, 522, said recirculation fluid circuit 560 cooperating with an actuator (not shown in FIG. 9) for managing the fluid passage in both directions between said first and second variable-volume sub-chambers 521, 522.

According to the embodiment shown in FIG. 9, recirculation fluid circuit pathway 560 is external to chamber 520 and it fluidically connects separate branches 542, 543 of inlet fluid circuit pathway 540 upstream from first and second inlet ports 523, 524 of sub-chambers 521, 522. In detail, a first axial end 561 of recirculation fluid circuit pathway 560 fluidically connects with second inlet pathway 542 of inlet fluid circuit pathway 540 downstream from seat 547 of the first inlet fluid circuit valve. Analogously, a second axial end 562 of recirculation fluid circuit pathway 560 fluidically connects with third inlet pathway 543 of inlet fluid circuit pathway 540 downstream from seat 548 of the second inlet fluid circuit valve.

Recirculation fluid circuit pathway 560 further comprises a seat 563 suitable for receiving an actuator (not shown in FIG. 9) which typically is an active valve operated by the modular fluid delivery system as already explained above with reference for instance to the embodiment shown in FIG. 1. Preferably, said actuator is an electro-mechanical driven valve that is automatically controlled and operated by a processor (processor P in FIG. 1) of the modular fluid delivery system. As schematically shown in the figures, processor P controls and operates said actuator, driving unit M and the supply station valve.

According to an embodiment of the present disclosure, said actuator is not part of disposable pump module 500, the latter being only provided with seat 563 for receiving the actuator which preferably is a component possessed by the modular fluid delivery system. For instance, in case the modular fluid delivery system is a powered injector suitable for being used in the medical field, the actuator of recirculation fluid circuit pathway 560 is typically located at the injector head.

Alternatively, said actuator is part of disposable pump module 500 and it is received within its seat 563 that is formed within supporting element 510.

Figure 10:
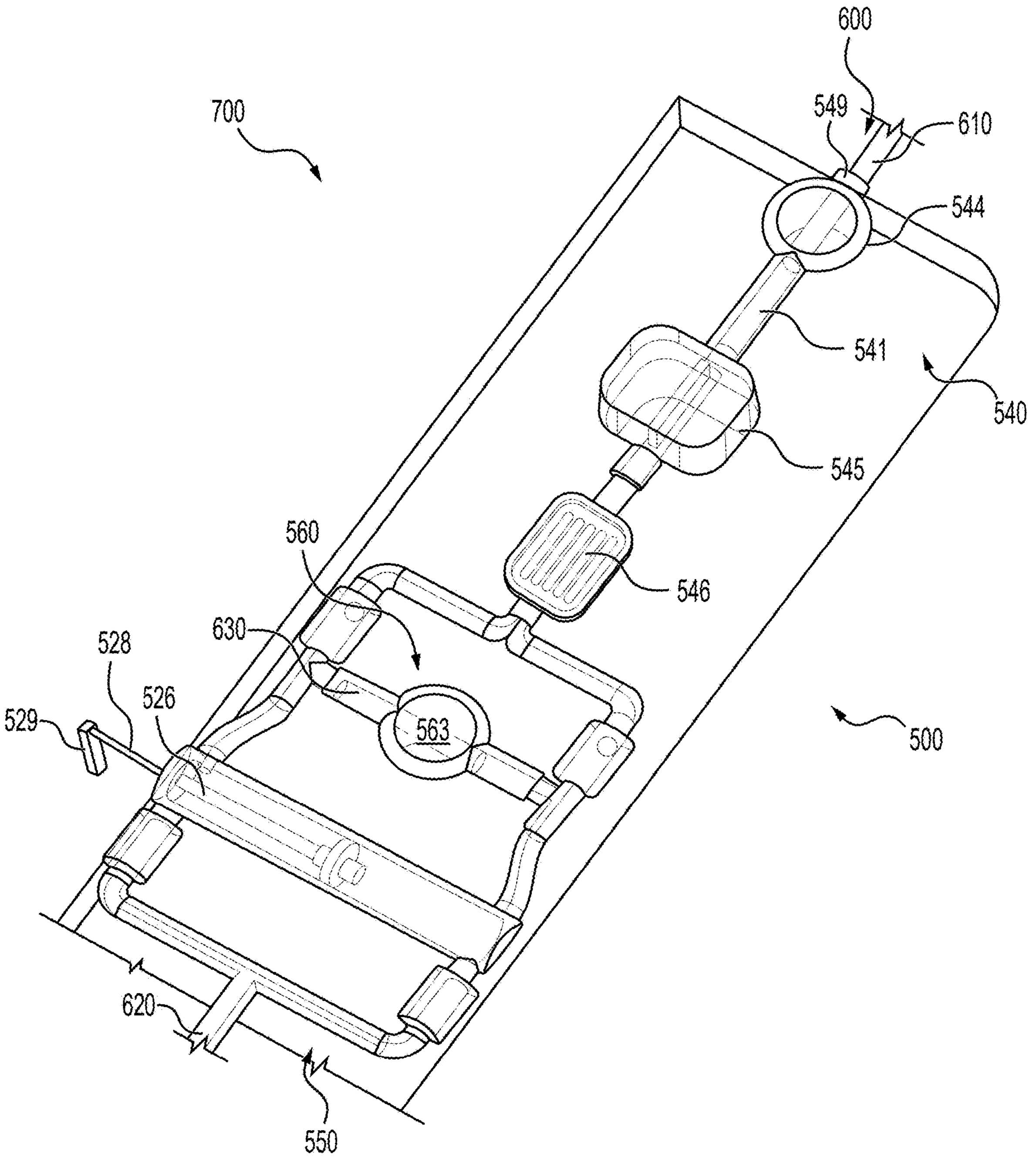
FIG. 10 shows a perspective view of a disposable pump module assembly comprising the disposable pump module of the embodiment shown in FIG. 9.

FIG. 10 shows a perspective view of a disposable pump module assembly 700 according to an embodiment of the present disclosure. In detail, FIG. 10 shows disposable pump module 500 of FIG. 9 in combination with a fluid circuit tubing 600 suitable for connecting to a fluid supply reservoir (not shown), for conveying said fluid along the various pathways possessed by the disposable pump module (as previously described with reference to FIG. 9) and, finally, for discharging said fluid outside the disposable pump module at a predetermined pressurized state (i.e. at desired pressure and flow rate values).

Disposable pump module 500 of FIG. 9 and disposable pump module assembly 700 of FIG. 10 are designed and configured to receive and discharge only one typology of fluid.

Fluid circuit tubing 600 comprises, respectively, an inlet fluid circuit tubing 610 (whose branches are received within corresponding first, second and third inlet pathways 541, 542,543), an outlet fluid circuit tubing 620 (whose branches are received within first and second outlet pathways 551, 552) and a recirculation fluid circuit tubing 630 (which is received within recirculation fluid circuit pathway 560).

According to a first embodiment, inlet fluid circuit tubing 610 comprises two distal ends and a proximal end. In detail, the two distal ends connect, respectively, with first inlet port 523 of first sub-chamber 521 and with second inlet port 524 of second sub-chamber 522, while the proximal end is provided with a connector (not shown in FIG. 10) for fluidically engaging the fluid supply station (not shown in FIG. 10).

Moreover, outlet fluid circuit tubing 620 comprises two proximal ends and a distal end. In detail, the two proximal ends connect, respectively, with first outlet port 553 of first sub-chamber 521 and with second outlet port 554 of second sub-chamber 522, while the distal end is typically provided with a connector (not shown in FIG. 10) for discharging the pressurized fluid exiting the disposable pump module assembly. In case the latter is applied to the medical field (e.g. for injecting a given substance—e.g. contrast agent, medicament, drug—into a patient's vasculature or organ), typically the connector of said distal end fluidically engages an additional tubing (generally indicated as patient line) which ensures that the disposable pump module assembly is not cross-contaminated when a new patient is connected to a disposable pump module assembly that has already been used for a previous patient. In fact, the additional tubing is disposed after each single use while the disposable pump module assembly is kept in operation for a given number of patients and/or for a predetermined period of time as mentioned above.

Alternatively, the proximal end of inlet fluid circuit tubing 610 terminates flush with proximal port 549 of inlet fluid circuit pathway 540, and a connector is directly associated with said proximal port 549 for fluidically connecting to the fluid supply station.

According to a second embodiment (shown in FIG. 10), fluid circuit tubing 600 does not require to be a continuous tubing or an uninterrupted sequence of continuous tubing branches that are received along the longitudinal extension of the whole inlet, outlet and recirculation fluid circuit pathways. In fact, a major part of the fluid circuit pathways (which are created when making supporting element 510, e.g. by associating together the two molded parts which form said supporting element) already define a conduit which per se is suitable for vehiculating the fluid while it flows inside and along the disposable pump module. Therefore, according to said second embodiment, fluid circuit tubing 600 only comprises few and very short tubing portions that are mainly provided at sensitive locations of the disposable pump module where detection of a fluid specific property should occur or a specific action is requested to be performed onto the fluid flow. For instance, a tubing portion is typically requested to be present in correspondence of first seat 544 where a supply station valve (not shown in FIG. 9 and FIG. 10) is operated to act (e.g. to clamp) on said tubing portion for regulating the fluid to enter or to not enter the disposable pump module. As a further example, a tubing portion is typically requested to be present also in correspondence of second seat 545 where an air bubble detector (not shown in FIG. 9 and FIG. 10) is operated for checking presence, number and/or size of air bubbles contained within the flowing fluid. As a further example, a tubing portion is typically requested to be present also in correspondence of seat 563 where an actuator (not shown in FIG. 9 and FIG. 10) is operated to act (e.g. to clamp) on said tubing portion for regulating the fluid to pass through or to not pass through recirculation fluid circuit pathway 560.

It can be understood that several technical solutions can be used for intercepting a fluid flow, for alternately blocking and releasing it, or for making a specific measurement (like detecting air bubbles) on the flowing fluid. Therefore, based on the technical solution which is chosen to be implemented, it is apparent that, in a predetermined part of fluid circuit tubing 600, a tubing portion can be avoided or it is absolutely strictly necessary. For example, in case an electromagnetic closure or a rotary valve (which could be actuated by a processor possessed by the fluid delivery system) is positioned within (i.e. internally to) a fluid circuit pathway, the latter can be suitably used as conduit for the fluid flowing. Therefore, in this case the conduit created when the fluid circuit pathway is formed (i.e. the fluid track that is generated when the two separate layers are assembled together) is sufficient for properly guiding and intercepting the fluid flow without any need of providing additional tubing portions.

FIG. 10 shows also an extension 528 of piston rod 526 which engages a suitable gear 529 (not shown in detail) for connecting piston 525 to driving unit M (not shown in FIG.

10). Preferably, gear 529 is not part of disposable pump module assembly 700 and it is contained in the modular fluid delivery system (therefore, in case the latter is an injector for being used in the medical field, gear 529 is part of the injector head).

As it will be explained more in detail with reference to FIG. 16, the modular fluid delivery system according to an embodiment of the present disclosure comprises at least one disposable pump module assembly 700. For instance, in case two distinct fluids are requested to be suitably delivered, the modular fluid delivery system according to an embodiment of the present disclosure can comprise a first disposable pump module assembly 700 for delivering a first fluid, and a second disposable pump module assembly 700 for delivering a second fluid, said second fluid being different from said first fluid.

According to an embodiment of the modular fluid delivery system of the present disclosure, the first disposable pump module assembly 700 for delivering the first fluid and the second disposable pump module assembly 700 for delivering the second fluid are arranged in series, said first and second pump module assemblies being connected to a common driving unit M of the modular fluid delivery system (like fluid delivery system 200' shown in FIG. 6).

According to an alternative embodiment of the modular fluid delivery system of the present disclosure, the first disposable pump module assembly 700 for delivering the first fluid and the second disposable pump module assembly 700 for delivering the second fluid are arranged in parallel to each other. According to an embodiment of said parallel arrangement, said first and second pump module assemblies are connected to a common driving unit M of the modular fluid delivery system (like fluid delivery system 200 shown in FIG. 5). According to an alternative embodiment of said parallel arrangement, said first pump module assembly is connected to a first driving unit of the modular fluid delivery system and said second pump module assembly is connected to a second driving unit of the modular fluid delivery system, said first and second driving units being separate and distinct driving units.

Figure 11:
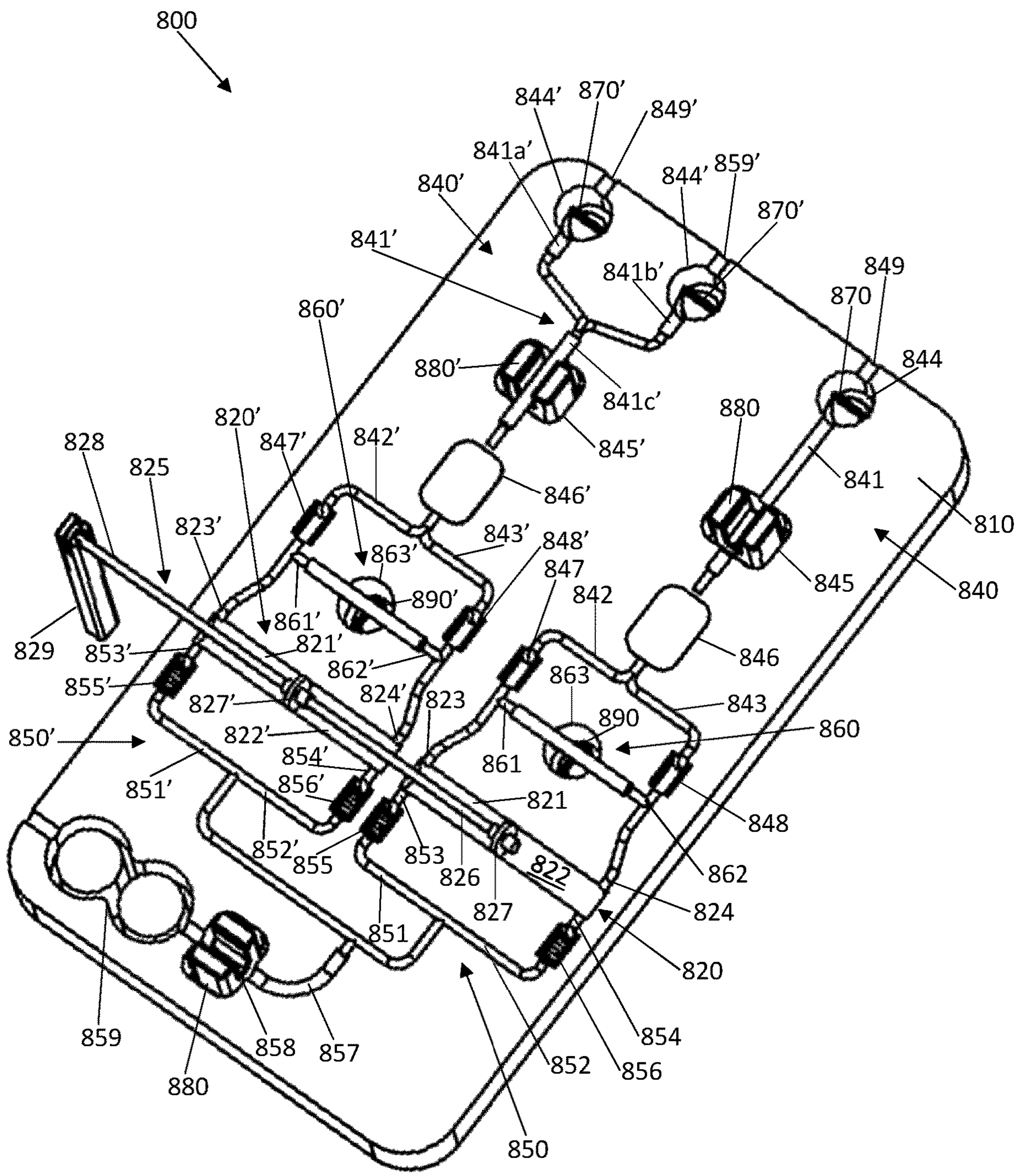
FIG. 11 and FIG. 12 show perspective views of a further embodiment of a disposable pump module and a disposable pump module assembly, respectively, of the present disclosure in which two distinct fluid circuits pathways are envisaged.
Figure 12:
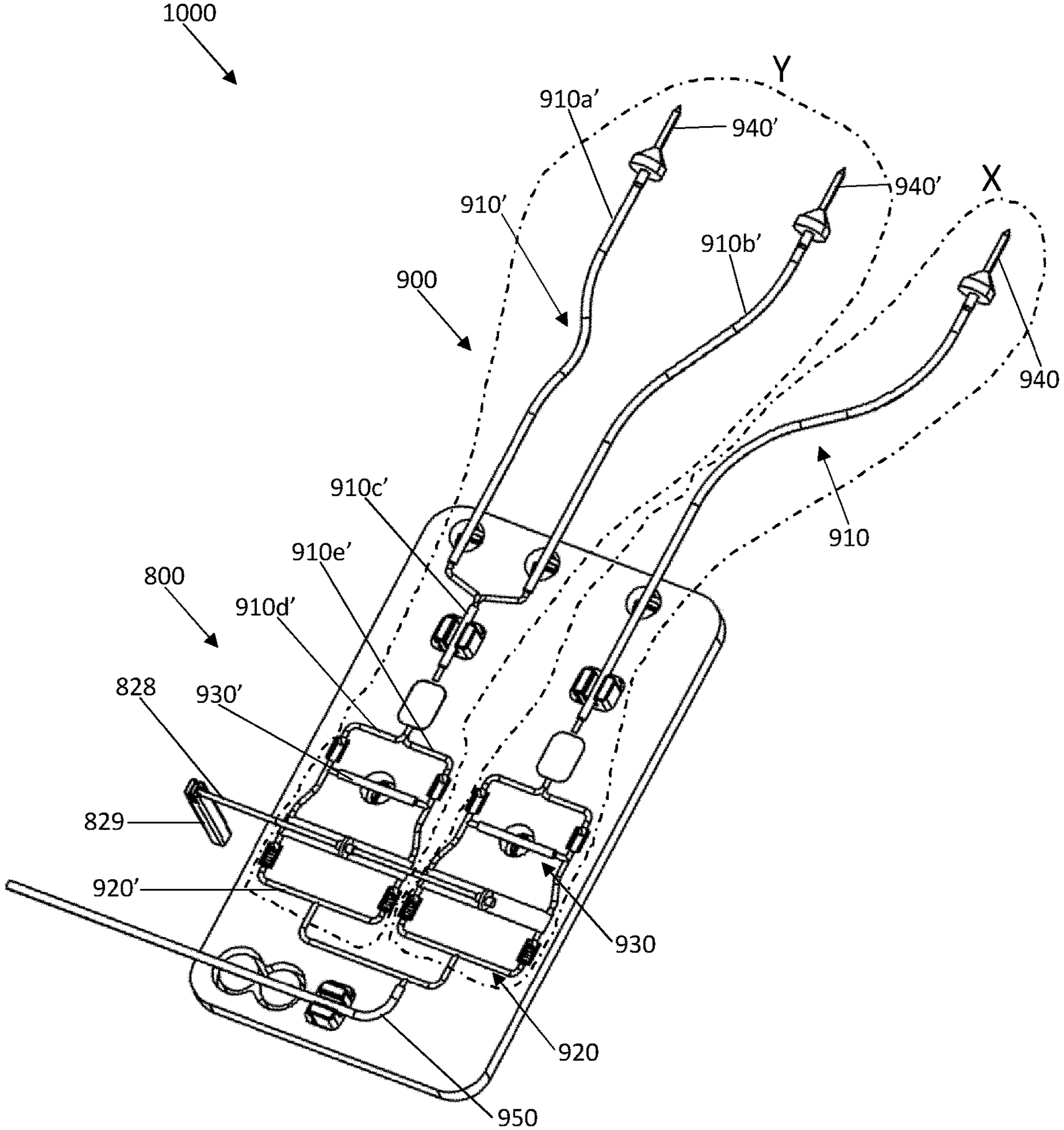

According to a further alternative embodiment of the present disclosure, a modular fluid delivery system for delivering a first fluid (contained in a first reservoir or first supply station) and a second fluid (contained in a second reservoir or second supply station), said first fluid and said second fluid being different from each other, is provided with a single disposable pump module assembly that comprises two distinct fluid circuits X, Y arranged in series as shown in FIG. 11 and FIG. 12, said single disposable pump module assembly being designed to accomplish, for instance, fluid delivery system 200' of FIG. 6.

In detail, FIG. 11 shows a perspective view of an embodiment of a disposable pump module 800 of a modular fluid delivery system according to the present disclosure. Disposable pump module 800 comprises two separate fluid circuits X, Y (shown in FIG. 12) for managing and pressurizing two distinct fluids, i.e. a first fluid being provided to first fluid circuit X and a second fluid being provided to second fluid circuit Y. Analogously to disposable pump module 500 of FIG. 9, disposable pump module 800 comprises a supporting element 810 which includes, for each fluid circuit X, Y, at least the following components: a chamber 820, 820' (first chamber 820 being associated to first fluid circuit X and second chamber 820' being associated to second fluid circuit Y), an inlet fluid circuit pathway 840, 840' entering said chamber (first inlet fluid circuit pathway 840 being associated to first fluid circuit X and entering first chamber 820, and second inlet fluid circuit pathway 840' being associated to second fluid circuit Y and entering second chamber 820'), an outlet fluid circuit pathway 850, 850' (first outlet fluid circuit pathway 850 being associated to first fluid circuit X and exiting from first chamber 820, and second outlet fluid circuit pathway 850' being associated to second fluid circuit Y and exiting from second chamber 820') and a recirculation fluid circuit pathway 860, 860' (first recirculation fluid circuit pathway 860 being associated to first fluid circuit X and connecting two separate opposite branches of said first inlet fluid circuit pathway 840, and second recirculation fluid circuit pathway 860' being associated to second fluid circuit Y and connecting two separate opposite branches of said second inlet fluid circuit pathway 840').

Typically, supporting element 810 is obtained by associating together two distinct layers (not visible in FIG. 11, but clearly shown in FIG. 13, for instance), each layer being provided with suitably sized recesses, thereby forming the above components of the two fluid circuits X, Y once the two layers are integrally engaged together so that said formed components result in being embedded in the supporting element thickness. Preferably, said layers are molded plastic layers.

Inlet fluid circuit pathways 840, 840' are in fluid communication with corresponding fluid supply stations (not shown in FIG. 11) and with respective chambers 820, 820'.

With reference to first fluid circuit X, in detail first inlet fluid circuit pathway 840 comprises a first inlet pathway 841 which successively branches into a second inlet pathway 842 and a third inlet pathway 843 that are in fluid communication, respectively, with a first variable-volume sub-chamber 821 and a second variable-volume sub-chamber 822 of first chamber 820. In fact, disposable pump module 800 further comprises a piston 825 which is reciprocated (i.e. moved back and forth by a driving unit M) within first chamber 820. Piston 825 comprises a piston rod 826 and a first plunger 827, the plunger being arranged to be substantially perpendicular to the piston rod and having a radial extension which substantially corresponds to first chamber width. Therefore, in cooperation with internal walls of first chamber 820, first plunger 827 defines said first sub-chamber 821 on one side of the plunger (on the left side of the first plunger in the embodiment of FIG. 11) and a second sub-chamber 822 on the opposite side of the plunger (on the right side of the first plunger in the embodiment of FIG. 11).

First inlet pathway 841 further comprises a first seat 844 for receiving a supply station valve 870 (which is shown in FIG. 11 for a better understanding of its positioning and interaction with disposable pump module 800) that allows the first fluid to be suitably discharged from the first supply station. The supply station valve is an active valve that is directly operated by the fluid delivery system, as previously explained with reference to FIG. 6.

Preferably, the supply station valve is not part of disposable pump module 800 and, typically, it is a component possessed by the modular fluid delivery system. For instance, in case the modular fluid delivery system is a powered injector suitable for being used in the medical field, the supply station valve is typically received within the injector head.

Alternatively, supply station valve 870 is part of disposable pump module 800 and it is received within first seat 844 of supporting element 810.

In some applications, first inlet pathway 841 further comprises a second seat 845 for receiving an air bubble detector 880 (which is shown in FIG. 11 for a better understanding of its positioning and interaction with disposable pump module 800) which is possessed by the modular fluid delivery system (and thus it is not part of disposable pump module 800) and which is used for detecting the presence of air bubbles possibly contained in the first fluid discharged from the first supply station. The air bubble detector can be of any type known in the art, e.g. an ultrasonic or a capacitive sensor.

First inlet pathway 841 further comprises a third seat 846 for receiving a filtering unit (not shown in FIG. 11) which can be used, if necessary, for guaranteeing absence of impurities or any additional substance which should not be contained in the fluid(s) to be delivered. The filtering unit is an optional component and the presence thereof depends on the fluid(s) nature/characteristics.

Downstream from third seat 846, first inlet pathway 841 branches into second inlet pathway 842 and third inlet pathway 843 which are in fluid communication with first sub-chamber 821 and second sub-chamber 822, respectively. First sub-chamber 821 is provided with a first inlet port 823 which allows second inlet pathway 842 to be in fluid communication with first sub-chamber 821. Analogously, second sub-chamber 822 is provided with a second inlet port 824 which allows third inlet pathway 843 to be in fluid communication with second sub-chamber 822.

Upstream from first inlet port 823, second inlet pathway 842 is provided with a seat 847 for receiving a first inlet fluid circuit valve (not shown in FIG. 11) which allows the first fluid to flowing into first sub-chamber 821 through second inlet pathway 842. According to an embodiment of the present disclosure, first inlet fluid circuit valve is a check valve, i.e. a one-way valve which allows the fluid to flow through it in only one direction, specifically from the first supply station towards first sub-chamber 821, thereby avoiding that the first fluid flows back towards the first supply station.

Analogously, upstream from second inlet port 824, third inlet pathway 843 is provided with a seat 848 for receiving a second inlet fluid circuit valve (not shown in FIG. 11) which allows the first fluid to flowing into second sub-chamber 822 through third inlet pathway 843. According to an embodiment of the present disclosure, second inlet fluid circuit valve is a check valve, i.e. a one-way valve which prevents reverse flow allowing the first fluid to flow through it in only one direction, specifically from the first supply station towards second sub-chamber 822, thereby avoiding that the first fluid flows back towards the first supply station.

Preferably, first and second inlet fluid circuit valves are ball check valves in which a ball is present inside the body valve for regulating the fluid flow.

As mentioned above, disposable pump module 800 further comprises outlet fluid circuit pathway 850 which is separate from inlet fluid circuit pathway 840. Outlet fluid circuit pathway 850 is in fluid communication with chamber 820 and it comprises a first outlet pathway 851 and a second outlet pathway 852 for discharging the first fluid from chamber 820. In detail, first sub-chamber 821 is provided with a first outlet port 853 which allows first outlet pathway 851 to be in fluid communication with first sub-chamber 821. Analogously, second sub-chamber 822 is provided with a second outlet port 854 which allows second outlet pathway 852 to be in fluid communication with second sub-chamber 822. As already described above with reference to FIG. 6, in operation first and second outlet pathways 851, 852 of outlet fluid circuit pathway 850 discharge the first fluid alternatively from first sub-chamber 821 and from second sub-chamber 822.

Downstream from first outlet port 853, first outlet pathway 851 is provided with a seat 855 for receiving a first outlet fluid circuit valve (not shown in FIG. 11) which allows the first fluid to being discharged from first sub-chamber 821 through first outlet pathway 851. According to an embodiment of the present disclosure, the first outlet fluid circuit valve is a check valve, i.e. a one-way valve which prevents reverse flow allowing the first fluid to flow through it in only one direction, specifically exiting from first sub-chamber 821, thereby avoiding that the first fluid flows back into said first sub-chamber 821.

Analogously, downstream from second outlet port 854, second outlet pathway 852 is provided with a seat 856 for receiving a second outlet fluid circuit valve (not shown in FIG. 11) which allows the first fluid to being discharged from second sub-chamber 822 through second outlet pathway 852. According to an embodiment of the present disclosure, the second outlet fluid circuit valve is a check valve, i.e. a one-way valve which allows the first fluid to flow through it in only one direction, specifically exiting from second sub-chamber 822, thereby avoiding that the first fluid flows back into said second sub-chamber 822.

Preferably, first and second outlet fluid circuit valves are spring loaded check valves wherein a spring component is used to support valve operation by eliminating the effect of gravity on the check valve function. More preferably, first and second outlet fluid circuit valves are spring loaded ball check valves.

According to the present disclosure, disposable pump module 800 further comprises a recirculation fluid circuit pathway 860 fluidically connecting said first and second variable-volume sub-chambers 821, 822, said recirculation fluid circuit 860 cooperating with an actuator 890 (which is shown in FIG. 11 for a better understanding of its positioning and interaction with disposable pump module 800) for managing the fluid passage in both directions between said first and second variable-volume sub-chambers 821, 822.

According to the embodiment shown in FIG. 11, recirculation fluid circuit pathway 860 is external to chamber 820 and it fluidically connects separate branches 842, 843 of inlet fluid circuit pathway 840 upstream from first and second inlet ports 823, 824 of sub-chambers 821, 822. In detail, a first axial end 861 of recirculation fluid circuit pathway 860 fluidically connects with second inlet pathway 842 of inlet fluid circuit pathway 840 downstream from seat 847 of the first inlet fluid circuit valve. Analogously, a second axial end 862 of recirculation fluid circuit pathway 860 fluidically connects with third inlet pathway 843 of inlet fluid circuit pathway 840 downstream from seat 848 of the second inlet fluid circuit valve.

Recirculation fluid circuit pathway 860 further comprises a seat 863 suitable for receiving said actuator 890 which typically is an active valve operated by the modular fluid delivery system as already explained above with reference to the embodiment shown in FIG. 6. Preferably, said actuator is an electro-mechanical driven valve that is automatically controlled and operated by a processor (processor P in FIG. 6) of the modular fluid delivery system. As schematically shown in the figures, processor P controls and operates said actuator, driving unit M and the supply station valve.

According to an embodiment of the present disclosure, said actuator 890 is not part of disposable pump module 800, the latter being only provided with seat 863 for receiving the actuator that preferably is a component possessed by the modular fluid delivery system. For instance, in case the modular fluid delivery system is a powered injector suitable for being used in the medical field, the actuator of recirculation fluid circuit pathway 860 is typically located at the injector head.

Alternatively, said actuator 890 is part of disposable pump module 800 and it is received within its seat 863 that is formed within supporting element 810.

With reference to second fluid circuit Y, in detail second inlet fluid circuit pathway 840' comprises a first inlet pathway 841' which successively branches into a second inlet pathway 842' and a third inlet pathway 843' that are in fluid communication, respectively, with a first sub-chamber 821' and a second sub-chamber 822' of second chamber 820'. In fact, piston 825 is reciprocated (i.e. moved back and forth by a driving unit M) not only within first chamber 820, but also within second chamber 820', said first and second chambers being arranged in series. Piston rod 826 comprises a second plunger 827' which is arranged substantially perpendicular to the piston rod and which has a radial extension substantially corresponding to second chamber width. Therefore, in cooperation with internal walls of second chamber 820', second plunger 827' defines said first sub-chamber 821' on one side of the plunger (on the left side of the second plunger in the embodiment of FIG. 11) and a second sub-chamber 822' on the opposite side of the plunger (on the right side of the second plunger in the embodiment of FIG. 11).

According to the embodiment shown in FIG. 11, first inlet pathway 841' comprises two opposite and separate branches 841'*a*, 841'*b* which convey into a common branch 841'*c* upstream from second inlet pathway 842' and third inlet pathway 843'. Each branch 841'*a*, 841'*b* comprises a first seat 844' for receiving a corresponding supply station valve 870' (the supply station valves 870' are shown in FIG. 11 for a better understanding of their positioning and interaction with disposable pump module 800) that allows the second fluid to be suitably discharged from two distinct second supply stations (not shown in FIG. 11). The supply station valve is an active valve that is directly operated by the fluid delivery system, as previously explained with reference to FIG. 6.

In some applications, common branch 841'*c* of first inlet pathway 841' further comprises a second seat 845' for receiving an air bubble detector 880' (which is shown in FIG. 11 for a better understanding of its positioning and interaction with disposable pump module 800) which is possessed by the modular fluid delivery system (and thus it is not part of disposable pump module 800) and which is used for detecting the presence of air bubbles possibly contained in the second fluid discharged from the second supply stations.

First inlet pathway 841' further comprises a third seat 846' for receiving a filtering unit (not shown in FIG. 11).

Downstream from third seat 846', first inlet pathway 841' branches into second inlet pathway 842' and third inlet pathway 843' which are in fluid communication with first sub-chamber 821' and second sub-chamber 822', respectively. First sub-chamber 821' is provided with a first inlet port 823' which allows second inlet pathway 842' to be in fluid communication with first sub-chamber 821'. Analogously, second sub-chamber 822' is provided with a second inlet port 824' which allows third inlet pathway 843' to be in fluid communication with second sub-chamber 822'.

Upstream from first inlet port 823', second inlet pathway 842' is provided with a seat 847' for receiving a first inlet fluid circuit valve (not shown in FIG. 11) which allows the second fluid to flowing into first sub-chamber 821' through second inlet pathway 842'. According to an embodiment of the present disclosure, first inlet fluid circuit valve is a check valve, i.e. a one-way valve which allows the fluid to flow through it in only one direction, specifically from the selected and operated second supply station towards first sub-chamber 821', thereby avoiding that the second fluid flows back towards the operated second supply station.

Analogously, upstream from second inlet port 824', third inlet pathway 843' is provided with a seat 848' for receiving a second inlet fluid circuit valve (not shown in FIG. 11) which allows the second fluid to flowing into second sub-chamber 822' through third inlet pathway 843'. According to an embodiment of the present disclosure, second inlet fluid circuit valve is a check valve, i.e. a one-way valve which prevents reverse flow allowing the second fluid to flow through it in only one direction, specifically from the selected and operated second supply station towards second sub-chamber 822', thereby avoiding that the second fluid flows back towards the operated second supply station.

Preferably, first and second inlet fluid circuit valves are ball check valves in which a ball is present inside the body valve for regulating the fluid flow.

As mentioned above, disposable pump module 800 further comprises outlet fluid circuit pathway 850' which is separate from inlet fluid circuit pathway 840'. Outlet fluid circuit pathway 850' is in fluid communication with chamber 820' and it comprises a first outlet pathway 851' and a second outlet pathway 852' for discharging the second fluid from chamber 820'. In detail, first sub-chamber 821' is provided with a first outlet port 853' which allows first outlet pathway 851' to be in fluid communication with first sub-chamber 821'. Analogously, second sub-chamber 822' is provided with a second outlet port 854' which allows second outlet pathway 852' to be in fluid communication with second sub-chamber 822'. As already described above with reference to FIG. 6, in operation first and second outlet pathways 851', 852' of outlet fluid circuit pathway 850' discharge the second fluid alternatively from first sub-chamber 821' and from second sub-chamber 822'.

Downstream from first outlet port 853', first outlet pathway 851' is provided with a seat 855' for receiving a first outlet fluid circuit valve (not shown in FIG. 11) which allows the second fluid to being discharged from first sub-chamber 821' through first outlet pathway 851'. According to an embodiment of the present disclosure, the first outlet fluid circuit valve is a check valve, i.e. a one-way valve which prevents reverse flow allowing the second fluid to flow through it in only one direction, specifically exiting from first sub-chamber 821', thereby avoiding that the second fluid flows back into said first sub-chamber 821'.

Analogously, downstream from second outlet port 854', second outlet pathway 852' is provided with a seat 856' for receiving a second outlet fluid circuit valve (not shown in FIG. 11) which allows the second fluid to being discharged from second sub-chamber 822' through second outlet pathway 852'. According to an embodiment of the present disclosure, the second outlet fluid circuit valve is a check valve, i.e. a one-way valve which allows the second fluid to flow through it in only one direction, specifically exiting from second sub-chamber 822', thereby avoiding that the second fluid flows back into said second sub-chamber 822'.

According to the present disclosure, disposable pump module 800 further comprises a recirculation fluid circuit pathway 860' fluidically connecting said first and second variable-volume sub-chambers 821', 822', said recirculation fluid circuit 860' cooperating with an actuator 890' (which is shown in FIG. 11 for a better understanding of its positioning and interaction with disposable pump module 800) for managing the fluid passage in both directions between said first and second variable-volume sub-chambers 821', 822'.

According to the embodiment shown in FIG. 11, recirculation fluid circuit pathway 860' is external to chamber 820' and it fluidically connects separate branches 842', 843' of inlet fluid circuit pathway 840' upstream from first and second inlet ports 823', 824' of sub-chambers 821', 822'. In detail, a first axial end 861' of recirculation fluid circuit pathway 860' fluidically connects with second inlet pathway 842' of inlet fluid circuit pathway 840' downstream from seat 847' of the first inlet fluid circuit valve. Analogously, a second axial end 862' of recirculation fluid circuit pathway 860' fluidically connects with third inlet pathway 843' of inlet fluid circuit pathway 840' downstream from seat 848' of the second inlet fluid circuit valve.

Recirculation fluid circuit pathway 860' further comprises a seat 863' suitable for receiving said actuator 890' which typically is an active valve operated by the modular fluid delivery system as already explained above with reference to the embodiment shown in FIG. 6. Preferably, said actuator is an electro-mechanical driven valve that is automatically controlled and operated by a processor (processor P in FIG. 6) of the modular fluid delivery system. As schematically shown in the figures, processor P controls and operates said actuator, driving unit M and the supply station valve.

According to an embodiment of the present disclosure, said actuator 890' is not part of disposable pump module 800, the latter being only provided with seat 863' for receiving the actuator that preferably is a component possessed by the modular fluid delivery system. For instance, in case the modular fluid delivery system is a powered injector suitable for being used in the medical field, the actuator of recirculation fluid circuit pathway 860' is typically located at the injector head.

Alternatively, said actuator 890' is part of disposable pump module 800 and it is received within its seat 863' that is formed within supporting element 810'.

According to the embodiment of the present disclosure shown in FIG. 11, first and second outlet fluid circuit pathways 850, 850' finally convey into a common outlet pathway 857 which defines a suitable track for allowing the first and second fluids to exiting disposable pump module 800.

Along its longitudinal extension, common outlet pathway 857 comprises a seat 858 for receiving an additional air bubble detector 880 (which is shown in FIG. 11 for a better understanding of its positioning and interaction with disposable pump module 800) that is operated to perform a final check on the fluid flow at the exit of disposable pump module 800.

Downstream from seat 858, common outlet pathway 857 further comprises a seat 859 for receiving at least one pressure sensor (not shown in FIG. 11) for suitably checking correctness of the pressure value of the two (first and second) pressurized fluids alternately and sequentially exiting disposable pump module 800. In the embodiment of FIG. 11, it can be noted that seat 859 is designed to receive two redundant pressure sensors, said pressure sensors being doubled for safety reasons.

It can be underlined that at least one pressure sensor is envisaged also in a modular fluid delivery system in which one or more disposable pump module assemblies provided with a single fluid circuit (e.g. like disposable pump module assembly 700 of FIG. 10) are envisaged. In this case (like modular fluid delivery system 5000 of FIG. 17 detailed in the following of the present description), the at least one pressure sensor is not received within the single or each single disposable pump module assembly, but it is located inside the modular fluid delivery system (e.g. in the injector head in case the modular fluid delivery system is an injector to be used in the medical field).

FIG. 12 shows a perspective view of a disposable pump module assembly 1000 according to an embodiment of the present disclosure. In detail, FIG. 12 shows disposable pump module 800 of FIG. 11 in combination with a fluid circuit tubing 900 suitable for connecting to first and second fluid supply stations (not shown in FIG. 12), for conveying said first and second fluids along the several pathways possessed by the disposable pump module (as previously described with reference to FIG. 11) and, finally, for discharging said first and second fluids outside of the disposable pump module at a predetermined pressurized state (i.e. at desired pressure and flow rate values).

Disposable pump module 800 of FIG. 11 and disposable pump module assembly 1000 of FIG. 12 are designed and configured to receive and discharge two different typologies of fluids, i.e. a first fluid and a second fluid, said second fluid being different from said first fluid, said first fluid being received within first fluid circuit X (shown in FIG. 12) and said second fluid being received within second fluid circuit Y (shown in FIG. 12).

With reference to first fluid circuit X and analogously to the embodiment already described in connection with FIG. 10, fluid circuit tubing 900 comprises, respectively, a first inlet fluid circuit tubing 910 (whose branches are received within corresponding first, second and third inlet pathways 841,842,843), a first outlet fluid circuit tubing 920 (whose branches are received within first and second outlet pathways 851,852) and a first recirculation fluid circuit tubing 930 (which is received within recirculation fluid circuit pathway 860).

According to a first embodiment, first inlet fluid circuit tubing 910 comprises two distal ends and a proximal end. In detail, the two distal ends connect, respectively, with first inlet port 823 of first sub-chamber 821 and with second inlet port 824 of second sub-chamber 822, while the proximal end is provided with a first connector 940 for fluidically engaging the fluid supply reservoir or fluid supply station (not shown) of the first fluid.

Moreover, first outlet fluid circuit tubing 920 comprises two proximal ends and a distal end. In detail, the two proximal ends connect, respectively, with first outlet port 853 of first sub-chamber 821 and with second outlet port 854 of second sub-chamber 822, while the distal end conveys into a common outlet tubing 950.

With reference to second fluid circuit Y, fluid circuit tubing 900 comprises a second inlet fluid circuit tubing 910', a second outlet fluid circuit tubing 920' and a second recirculation fluid circuit tubing 930'.

In detail, second inlet fluid circuit tubing 910' comprises two inlet tubings 910'*a*, 910'*b* which convey into a common intermediate inlet tubing 910'*c*, the latter finally branching again into two distinct final inlet tubings 910'*d*, 910'*e*. Each inlet tubing 910'*a*, 910'*b* is provided with a suitable connector 940' for fluidically engaging second inlet fluid circuit tubing 910' with two distinct supply stations of a second fluid which is requested to flow into second fluid circuit Y. Second inlet fluid circuit tubing 910' is provided with two distinct inlet tubings 910'*a*, 910'*b* so that two reservoirs of the same second fluid are always available in case the operated reservoir is approaching an empty state and a quick switch to a new full reservoir is requested for guaranteeing continuous supply of the second fluid without interruption of the modular fluid delivery system operation. Inlet tubings 910'*a*, 910'*b* are at least partially received within corresponding branches 841'*a*, 841'*b* of second inlet fluid circuit pathway 840' of disposable pump module 800. Furthermore, common intermediate inlet tubing 910'*c* is received within common branch 841'*c* of second inlet fluid circuit pathway 840', and final inlet tubings 910'*d*, 910'*e* are received within corresponding branches 842', 843' of said second inlet fluid circuit pathway 840'.

Moreover, the two separate branches possessed by second outlet fluid circuit tubing 920' are received, respectively, within first outlet pathway 851' and second outlet pathway 852', while second recirculation fluid circuit tubing 930' is received within second recirculation fluid circuit pathway 860'.

According to a first embodiment, first inlet fluid circuit tubing 910 of first fluid circuit X comprises two distal ends and a proximal end. In detail, the two distal ends connect, respectively, with first inlet port 823 of first sub-chamber 821 and with second inlet port 824 of second sub-chamber 822, while the proximal end is provided with a first connector 940 for fluidically engaging the fluid supply reservoir or fluid supply station (not shown) of the first fluid. On the contrary, second inlet fluid circuit tubing 910' of second fluid circuit Y comprises two distal ends and two proximal ends. In detail, the two distal ends connect, respectively, with second inlet port 823' of first sub-chamber 821' of second chamber 820', and with second inlet port 824' of second sub-chamber 822' of second chamber 820', while the two proximal ends are each provided with a second connector 940' for fluidically engaging the fluid supply reservoir or fluid supply station (not shown) of the second fluid.

Moreover, first outlet fluid circuit tubing 920 comprises two proximal ends and a distal end. In detail, the two proximal ends connect, respectively, with first outlet port 853 of first sub-chamber 821 and with second outlet port 854 of second sub-chamber 822, while the distal end conveys into a common outlet tubing 950.

According to an alternative embodiment, the distal ends of first inlet fluid circuit tubing 910 and of second inlet fluid circuit tubing 910' terminate flush with proximal port 849 of first inlet fluid circuit pathway 840 and with proximal ports 849' of second inlet fluid circuit pathway 840', so that first and second connectors 940, 940' are directly associated with said proximal ports for fluidically connecting and directly engaging the first fluid and the second fluid supply reservoirs.

According to the embodiment shown in FIG. 12, common outlet tubing 950 is received within common outlet pathway 857 as well as within seat 858 and seat 859 so that air bubble detector 880 and pressure sensor(s) can perform their relevant detections and measurements on first and second fluids pressurized by the disposable pump module assembly 1000, and in proximity of exit thereof.

Preferably, axial end of common outlet tubing 950 is provided with a further connector (not shown in FIG. 12) for discharging the pressurized fluid exiting the disposable pump module assembly 1000. In case the latter is applied to the medical field (e.g. for injecting contrast agent and saline into a patient's vasculature or organ for suitable imaging thereof), the connector of said distal end can fluidically engage an additional tubing (typically indicated as patient line) which ensures that the disposable pump module assembly is not cross-contaminated when a new patient is connected to the same disposable pump module assembly that has already been used for one or more previous patients.

According to a further embodiment (for instance shown in FIG. 12), fluid circuit tubing 900 does not require to be a continuous tubing or an uninterrupted sequence of continuous tubing branches that are received along the longitudinal extension of the whole inlet, outlet and recirculation fluid circuit pathways. In fact, a major part of the fluid circuit pathways (which are created when making supporting element 810, e.g. by associating together the two molded parts which form said supporting element) already define a conduit which per se is able to vehiculate the fluids while they flow inside and along the disposable pump module. Therefore, according to said further embodiment, fluid circuit tubing 900 only comprises few and very short tubing portions that are requested to be provided mainly at sensitive locations of the disposable pump module where detection and measurement of some specific properties of the fluids should be performed, or where a specific action is requested to be undergone on the fluid flow. For instance, a tubing portion is typically requested to be present in correspondence of first seats 844, 844' where supply station valves 870 are operated to act (e.g. to clamp) on said tubing portion for regulating the fluids to enter or to not enter the disposable pump module. As a further example, a tubing portion is typically requested to be present also in correspondence of second seats 845, 845' as well of seat 858 where air bubble detectors 880 are operated for checking presence, number and/or size of air bubbles contained within the flowing fluids. As a further example, a tubing portion is typically requested to be present also in correspondence of seats 863, 863' where actuators 890 are operated to act (e.g. to clamp) on said tubing portion for regulating the fluids to pass through or to not pass along first and second recirculation fluid circuit pathways 860, 860'. Moreover, a tubing portion is typically requested to be present also in correspondence of seats 859 where at least one pressure sensor is received for measuring pressure value of the flowing fluids.

FIG. 11 and FIG. 12 also show an extension 828 of piston rod 826 which engages a suitable gear 829 (schematically shown) for connecting piston 825 to driving unit M. Preferably, gear 829 is not part of disposable pump module assembly 1000 and it is contained in the modular fluid delivery system (therefore, in case the latter is an injector for being used in the medical field, gear 829 is part of the injector head).

It can be pointed out that disposable pump module assembly 1000 can be used not only in case one fluid or two distinct fluids are envisaged to be delivered, but it can be advantageously used also in case a mixture of two distinct fluids is envisaged to be delivered. This option can be suitably achieved thanks to the fact that, according to the embodiment shown in FIG. 12, second inlet fluid circuit tubing 910' of second fluid circuit Y comprises two inlet tubing 910'*a*, 910'*b* which not necessary are requested to connect to two supply stations containing the same fluid. In fact, as an alternative embodiment, inlet tubing 910'*a* can connect to a supply station containing a given first fluid and inlet tubing 910'*b* can connect to a supply station containing a given second fluid which is different from said given first fluid. Therefore, the modular fluid delivery system of the present disclosure can be operated (by suitably acting on the supply valves 870, 870' received within corresponding seats 844 and 844') so that an amount of said given first fluid and an amount of said given second fluid are supplied to first and second sub-chambers 821', 822' and, thanks to fluids recirculation through second recirculation fluid circuit tubing 930', said given first and second fluids are mixed together and thus a mixture thereof is suitably discharged from second outlet fluid circuit tubing 920'.

This aspect is particularly advantageous in case the modular fluid delivery system of the present disclosure is an injector suitable for being used in the medical field and the first fluid flowing into first fluid circuit X is a saline solution, while inlet tubing 910'*a* connects to a supply station containing a predetermined contrast agent and inlet tubing 910'*b* connects to a supply station containing said saline solution. Therefore, by suitably acting on the supply valves 870' received within corresponding seats 844', a predetermined amount of saline solution and a predetermined amount of contrast agent are suitably supplied to first and second sub-chambers 821', 822'. Thus, thanks to recirculation of these fluids through second recirculation fluid circuit tubing 930', the saline solution and the contrast agent can be mixed together at a given ratio, thereby making on site an amount of contrast agent at the desired concentration which is advantageously tailored to the specific patient under examination. Therefore, said modular fluid delivery system can be suitably used for sequentially injecting (according to a predetermined injection protocol) a saline solution through first fluid circuit X and a contrast agent at a desired concentration through second fluid circuit Y.

Figure 14:
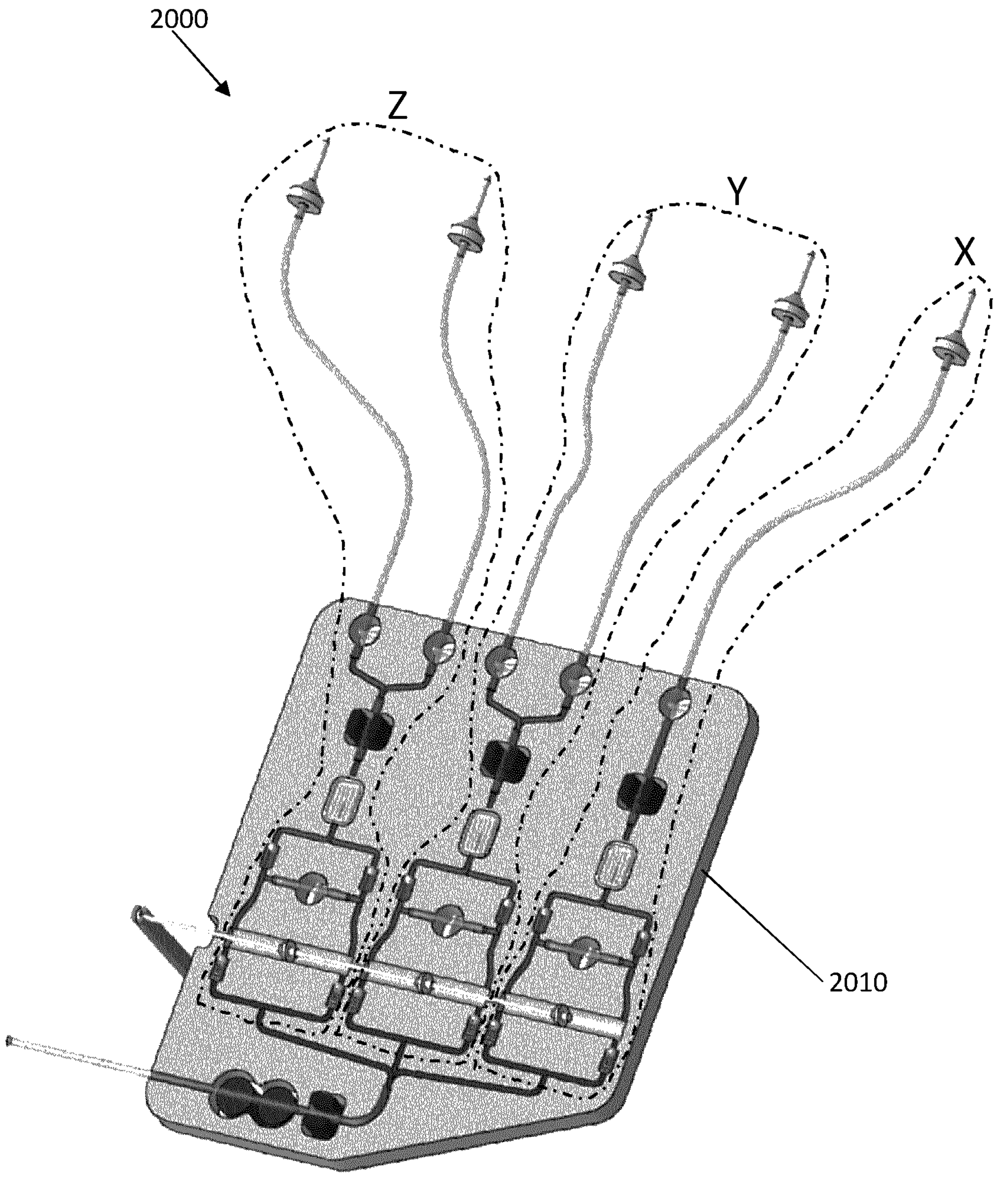

According to a further embodiment of the present disclosure shown in FIG. 13 and FIG. 14, a disposable pump module assembly 2000 comprises three distinct fluid circuits X, Y, Z that are arranged in series and provided on a same common supporting element 2010. FIG. 13 clearly shows that supporting element 2010 is preferably formed of two distinct layers 2020, 2030 that are associated together according to any suitable technique as mentioned above. Each layer is provided with predetermined recesses (i.e. tracks or grooves) that are properly designed and sized to form the main components possessed by the disposable pump module (e.g. the chambers, the various fluid pathways, the various seats for receiving valves, actuators, detectors, sensors, filters) once the two distinct layers 2020, 2030 are irreversibly combined to each other and said components result in being embedded in the thickness of supporting element 2010.

Disposable pump module assembly 2000 will not be described in detail in order to avoid useless and lengthy repetitions. However, the various components of each single fluid circuit X, Y, Z as well as operations thereof are identical or very similar to those shown in FIG. 9-12 and previously explained in the present description in relation to said figures.

According to said embodiment, disposable pump module assembly 2000 can be employed in a modular fluid delivery system of the present disclosure in which three different fluids can be chosen to be delivered, each fluid being provided to flow within a predetermined fluid circuit. For example, in case said modular fluid delivery system is an injector suitable for being used in the medical field, a first fluid flowing into first fluid circuit X can be a saline solution, a second fluid flowing into second fluid circuit Y can be a first contrast agent and a third fluid flowing into third fluid circuit Z can be a second contrast agent, said second contrast agent being different from said first contrast agent. Alternatively, the first contrast agent and the second contrast agent are the same contrast agent (i.e. the same chemical compound), but at different concentrations of the same active substance (e.g. Isovue® manufactured by Bracco is available on the market as Isovue®-200, Isovue®-250, Isovue®-300 and Isovue®-370 on the basis of the Iopamidol concentration contained therein). Therefore, by providing the modular fluid delivery system of the present disclosure equipped with disposable pump module assembly 2000, the operator can select which fluid or which fluids or which mixture of fluids can be injected on the basis of the specific needs that can be tailored on a given patient and on the examination which is requested to be performed. As mentioned above with respect to further embodiments of the present disclosure, the high flexibility of the modular fluid delivery system allows the operator to possibly select among many procedural options, like injecting one single contrast agent with a flushing of a saline solution (as it typically occurs in an MM procedure), or sequentially injecting a saline solution and a given contrast agent according to a predetermined injection protocol (as it typically occurs in a CT procedure) potentially choosing among more than one immediately available contrast agent, or even previously mixing a saline solution with a given contrast agent at a predetermined ratio so as to successively inject a patient with a tailored concentration of said contrast agent. According to a particularly advantageous configuration of said embodiment, the modular fluid delivery system of the present disclosure can be provided with a saline solution supply station and with only one contrast agent supply station, said contrast agent being selected (among those having the same desired chemical composition suitable for the examination to be performed) at highest available concentration. In fact, thanks to the mixing procedure mentioned above, by suitably calculating the saline solution and contrast agent ratio, it is possible to dilute the highly concentrated contrast agent so as to obtain the contrast agent at the desired concentration value.

Figure 15:
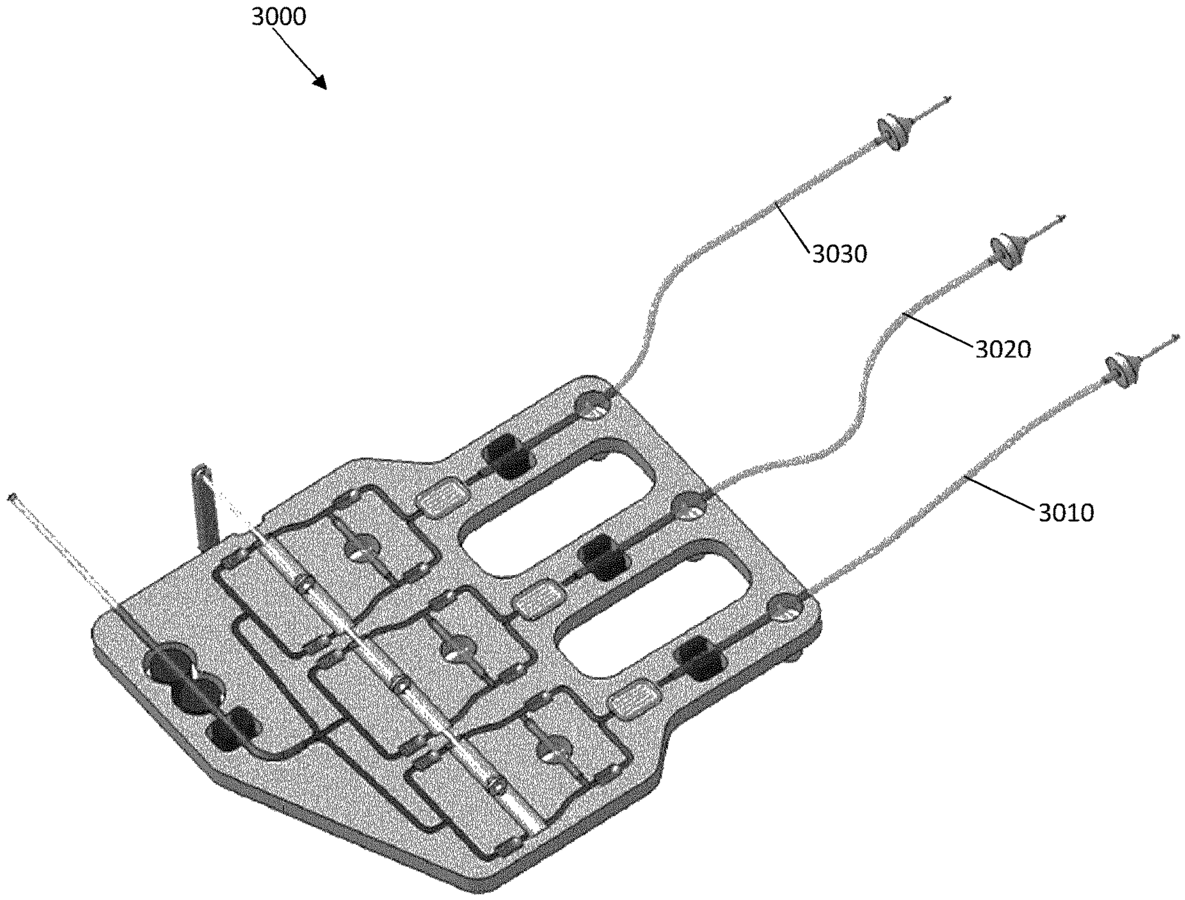
FIG. 15 shows a perspective view of an alternative of the disposable pump module assembly embodiment represented in FIG. 12 and FIG. 13, and FIG. 16 and FIG. 17 show schematic representations of modular fluid delivery systems according to the present disclosure.

According to a further alternative embodiment, FIG. 15 shows a disposable pump module assembly 3000 which, analogously to the embodiment shown in FIG. 14, comprises three distinct fluid circuits. However, each inlet fluid circuit tubing 3010, 3020, 3030 of each fluid circuit has only one single tubing for connecting to a corresponding fluid supply station (not shown).

As already mentioned above, the Applicant has perceived the need of providing a modular fluid delivery system which is extremely flexible for complying with the many and various operative applications that can be requested by a given customer. For instance, in case the fluid delivery system is an injector suitable for being used in the medical field, the Applicant has perceived the need of providing a single device which is designed and based on a modularity conception which makes said single device versatile and adjustable to many different operative conditions as well as to many different uses.

Figure 16:
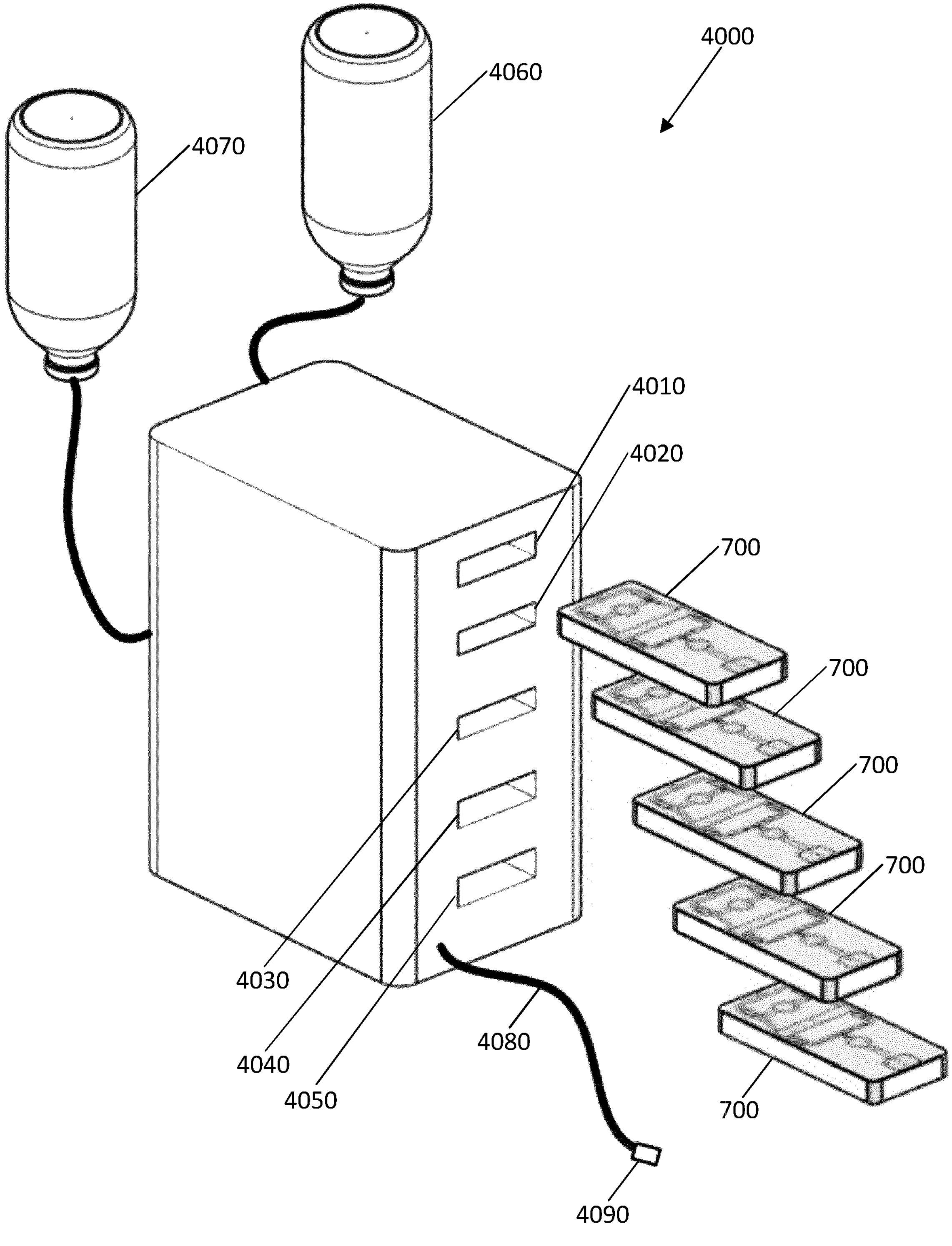

FIG. 16 shows a very schematic perspective view of an embodiment of a modular fluid delivery system 4000 according to the present disclosure. In detail, the modularity concept of modular fluid delivery system 4000 is obtained by envisaging a plurality of slots 4010, 4020, 4030, 4040, 4050, each slot being suitable for receiving, for instance, a disposable pump module assembly 700 of FIG. 10. According to this specific embodiment, all the available slots are identical to each other, and each slot is designed and sized to receive a disposable pump module assembly 700 which represents the most basic and simplest configuration since it envisages only one single fluid circuit within which a single predetermined fluid is allowed to flow. It can be appreciated that said modular fluid delivery system represents a scalable solution which satisfactorily and very easily adjusts to many situations where many and different fluids are possibly requested to be managed and delivered. For example, in case the modular fluid delivery system 4000 is an injector suitable for being used in the medical field, said injector can be provided with a plurality of fluid supply stations (only two 4060, 4070 being shown in FIG. 16) (e.g. a reservoir containing a saline solution, a plurality of reservoirs each containing a different contrast agent, a plurality of reservoirs each containing the same contrast agent but at different concentrations, a reservoir containing a specific medicament, . . . ) and with a desired number of disposable pump module assemblies which are fluidically connected to one or more of said fluid supply stations depending on the particular examination to be performed on a given patient. As indicated above, FIG. 16 represents a sketch (not a technical drawing) of the modular fluid delivery system, therefore fluid supply stations 4060, 4070 and fluid circuit tubings connected thereto, as well as the necessary mechanical connections (e.g. through gears) to one or more driving units are only partially shown or not shown at all. For instance, outlet tubing 4080 exiting the modular fluid delivery system 4000 is provided—at its free axial end—with a connector 4090 which can be used to fluidically connect the modular fluid delivery system to a patient line or a catheter (not shown in FIG. 16).

Figure 17:
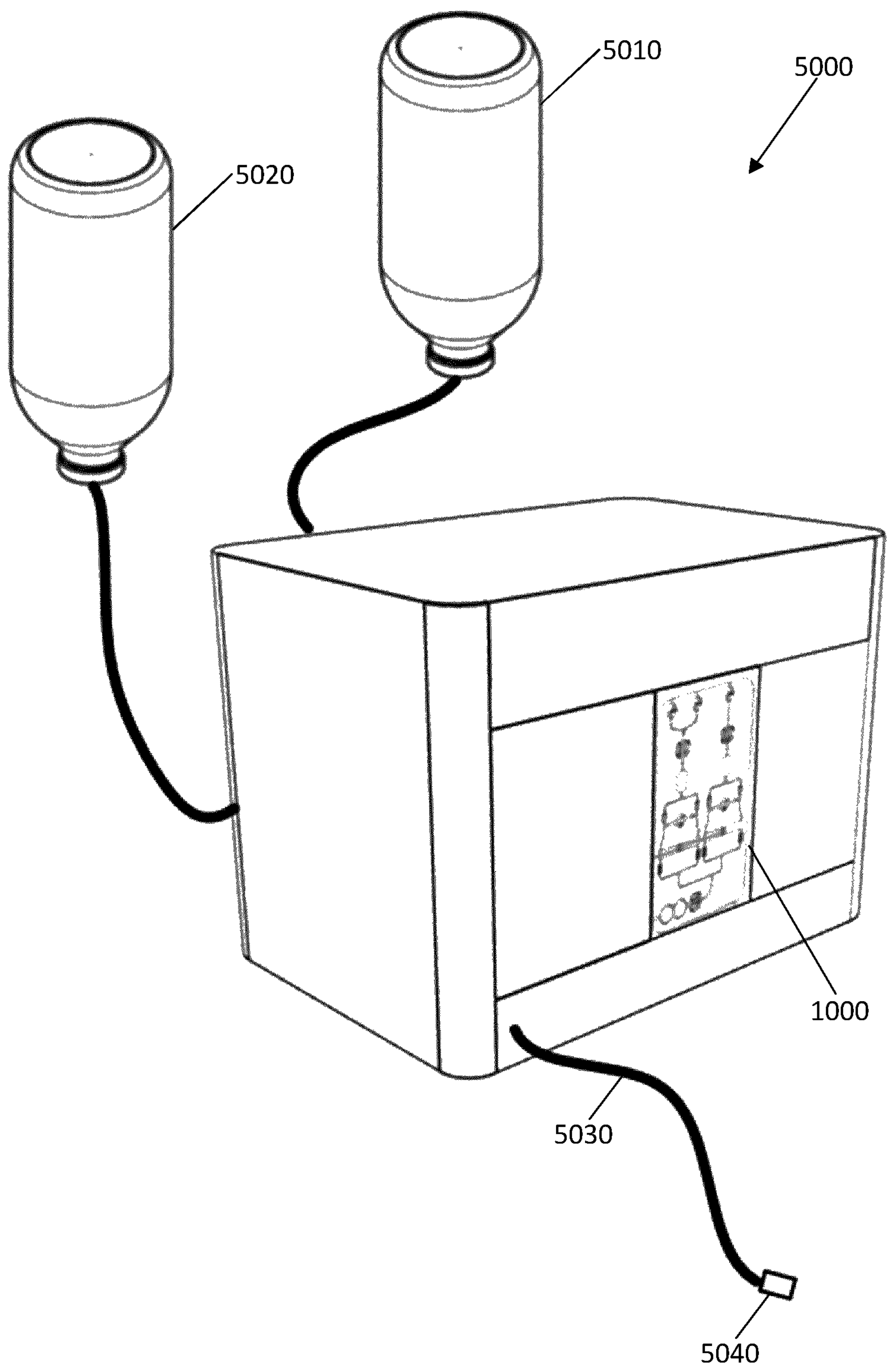

According to a further embodiment shown in FIG. 17, a modular fluid delivery system 5000 is designed to receive and fit any typology of the several disposable pump module assemblies disclosed above. For example, FIG. 17 shows disposable pump module assembly 1000 of FIG. 12 loaded onto (i.e. housed into) a modular fluid delivery system 5000. However, any other disposable pump module assembly can be loaded onto the modular fluid delivery system of the present disclosure for allowing the operator to comply with all the possible needs/requests from the field during his daily working activities. Therefore, the modular fluid delivery system of the present disclosure can be advantageously used for managing and delivering different fluids (as mentioned above), and it can also be operated in very different contexts. For instance, in case a medical field application is taken into consideration, said modular fluid delivery system can be envisaged to selectively perform CT, MR and/or Angiography examinations according to the specific medical needs of a given patient to be treated. It should be underlined that said typologies of examinations require rather different operative and environmental conditions, so that they are traditionally carried out by using distinct and dedicated injectors (i.e. a CT injector, an MRI injector or an Angiographic injector). On the contrary, the modular fluid delivery system of the present disclosure can be provided with dedicated engagements (e.g. slots or housings) that are suitable for receiving thereinto disposable pump module assemblies, each one being devoted to a specific examination. Thus, it is apparent that the modular fluid delivery system of the present disclosure is extremely versatile and one single device (e.g. injector) can be used for performing very different examinations, like CT, MR and Angiographic procedures.

Modular fluid delivery system 5000 of FIG. 17 represents only a sketch. Therefore, fluid supply stations 5010, 5020 and fluid circuit tubings connected thereto, as well as all the necessary mechanical connections (e.g. through gears) to one or more driving units are only partially shown or not shown at all. For instance, outlet tubing 5030 exiting the modular fluid delivery system 5000 is provided—at its free axial end—with a connector 5040 which can be used to fluidically connect the modular fluid delivery system to a patient line or a catheter (not shown in FIG. 17).

Modifications

In order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary details. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items); the terms based on, dependent on, according to, function of (and any forms thereof) should be intended as a non-exclusive relationship (i.e., with possible further variables involved); the term a/an should be intended as one or more items (unless expressly indicated otherwise); the term means for (or any means-plus-function formulation) should be intended as any structure adapted or configured for carrying out the relevant function.

According to an embodiment of the present disclosure (not shown in the figures), the volume of the supply station is remarkably greater than the volume of the chamber of the fluid delivery system. This aspect is particularly advantageous since it ensures that a high number of deliveries (e.g. of injections) can be performed without requesting frequent changes of the fluid reservoir and, moreover, it ensures that the overall size of the fluid delivery system can be advantageously minimized, thereby making it more flexible, less cumbersome, portable (if needed) and less expensive too.

According to an embodiment of the present disclosure, the modularity of the fluid delivery system can advantageously allow to select a disposable pump module assembly whose relevant components have a size which is properly correlated to the amount of fluid(s) that is requested to be delivered in the specific application under consideration. For example, in case the modular fluid delivery system of the present disclosure is used in substitution of a traditional powered injector for Mill procedures, due to the fact that an MM contrast agent is typically injected in a small amount with respect to a CT contrast agent, the volume (i.e. the size) of the chamber of the disposable pump module which receives and manages the MM contrast agent can be designed to be suitably small. This aspect is particularly advantageous not only because the overall size of the disposable pump module assembly can be properly reduced (thereby making it less expensive and handier for the operator), but also because it contributes in avoiding waste of the expensive contrast agent since the fluid delivery system will operate (i.e. supply from the relevant supply station, distribute along the relevant fluid circuit, manage within and deliver from the chamber) substantially only the contrast volume amount that is requested to be injected.

According to a further embodiment of the present disclosure (not shown in the figures), in case a disposable pump module assembly comprises more than one chamber, said chambers can have different volumes from each other. For example, the chamber appointed to receive a contrast agent can have a smaller volume than an adjacent chamber appointed to receive a saline solution, since an injection protocol for a CT examination (for instance) typically requests a higher amount of saline solution with respect to the used amount of contrast agent.

Moreover, independently from the specific fluid to be delivered, the volume of the chamber(s) possessed by the disposable pump module assembly can be sized to a minimum volume (thereby getting benefit from the advantages mentioned above) even though the volume of the delivered fluid is considerably high. This aspect can be achieved thanks to the design of the disposable pump module assembly of the present disclosure, i.e. the arrangement of its relevant components as well as their reciprocal interconnection and their coupling with other relevant components of the modular delivery system (e.g. the driving unit(s) and the processor). For instance, a delivered fluid high volume, while making use of a rather small volume chamber of said fluid, can be obtained by increasing the back and forth axial speed of the piston within said chamber.

As mentioned above, the disposable pump module assembly shown in FIG. 12 comprises one common piston 825 which is axially reciprocated within first and second chambers 820, 820'. According to an alternative embodiment (not shown in the figures), each distinct fluid circuit X, Y is provided with a chamber having a corresponding dedicated piston. Each dedicated and separate piston can be connected (e.g. through a suitable gearbox) to the same driving unit, or, as a further alternative, each dedicated and separate piston is connected to two distinct driving units. Of course, the same concept can be applied to a disposable pump module assembly which comprises more than two fluid circuits (e.g. to disposable pump module assembly 2000 of FIG. 14).

The disposable pump module assembly of the present disclosure can be connected to a driving unit of the modular fluid delivery system by providing the free axial end of the piston rod (i.e. the end of the piston rod which is outside the relevant chamber and which is not integral with the piston flange) with a connecting element (e.g. an external flange) engageable by any suitable holding mechanism, or holding and locking mechanism controlled by the driving unit.

According to an alternative embodiment (not shown) of the modular fluid delivery system of the present disclosure, a different arrangement of the slots, and thus of the corresponding disposable pump module assemblies received therein, is envisaged. The different spatial configuration (e.g. different from the vertical alignment shown in FIG. 16) can contribute not only to provide a different shape and encumbrance to the modular fluid delivery system, but also to identify different technical solutions. For example, according to the embodiment of FIG. 16, it could be envisaged that the disposable pump module assemblies are arranged (and thus are operated) in parallel to each other. On the contrary, according to said further alternative embodiment some slots can be aligned in a vertical configuration and some others can be aligned in a horizontal configuration. Therefore, the disposable pump module assemblies that lie on the same horizontal plane can be arranged in series and their respective pistons can be connected to the same gear (not shown) and/or to the same driving unit (not shown).

According to a further embodiment of the modular fluid delivery system of the present disclosure (not shown in the figures), instead of arranging the disposable pump module assemblies in suitable slots (i.e. properly sized seats for receiving as well as safely and properly engaging said assemblies, e.g. housings created inside the body of the modular fluid delivery system) which are distributed in multiple rows configurations (e.g. along one line in a vertical sequence or in a horizontal sequence, or multiple lines with a combination of vertical and horizontal sequences), said assemblies can be arranged along a circular path (e.g. like the cylinder of a revolver) that is rotatable and that defines a delivery position in which the selected assembly (i.e. selected on the basis of the specific application under consideration) is positioned for being operated by the system.

The following are preferred aspects and embodiments of the present disclosure.

1. A modular fluid delivery system (4000; 5000) comprising:
   - at least one supply station (4060; 4070; 5010; 5020) for supplying at least one fluid, and
   - a pressurizing unit (20; 220) for pressurizing said at least one fluid, said pressurizing unit comprising at least one driving unit (M) and at least one disposable pump module assembly (700; 1000; 2000; 3000), characterized in that said at least one disposable pump module assembly comprises:
   - at least one disposable pump module (500; 800) which comprises a supporting element (510; 810; 2010) defining:
     - at least one chamber (520; 820; 820') receiving a piston (525; 825) therein, said piston having a plunger (527; 827; 827') that, in cooperation with internal walls of said chamber, defines first (521; 821; 821') and second (522; 822; 822') variable-volume sub-chambers;
     - at least one inlet fluid circuit pathway (540; 840; 840');
     - at least one outlet fluid circuit pathway (550; 850; 850'), and
     - at least one recirculation fluid circuit pathway (560; 860; 860'), and
   - a fluid circuit tubing (600; 900) which comprises:
     - at least one inlet fluid circuit tubing (610; 910; 910') at least partially received within said at least one inlet fluid circuit pathway (540; 840; 840'), said at least one inlet fluid circuit tubing (610; 910; 910') being in fluid communication with said at least one supply station and with said at least one chamber for supplying said at least one fluid to said first and second variable-volume sub-chambers;
     - at least one outlet fluid circuit tubing (620; 920; 920') at least partially received within said at least one outlet fluid circuit pathway (550; 850; 850'), said at least one outlet fluid circuit tubing (620; 920; 920') being in fluid communication with said at least one chamber for discharging the fluid alternatively from said first and second variable-volume sub-chambers, said outlet fluid circuit tubing being separate from said inlet fluid circuit tubing, and
     - at least one recirculation fluid circuit tubing (630; 930; 930') at least partially received within said at least one recirculation fluid circuit pathway (560; 860; 860'), said at least one recirculation fluid circuit tubing fluidically connecting said first and second variable-volume sub-chambers.
2. The modular fluid delivery system (4000; 5000) according to Embodiment 1, characterized in that the at least one inlet fluid circuit pathway (540; 840; 840') comprises a first inlet pathway (541; 841; 841') which branches into a second inlet pathway (542; 842; 842') and a third inlet pathway (543; 843; 843') that are in fluid communication, respectively, with said first sub-chamber (521; 821; 821') and with said second sub-chamber (522; 822; 822').

3. The modular fluid delivery system (4000; 5000) according to Embodiment 2, characterized in that said first inlet pathway (541; 841; 841') comprises a first seat (544; 844; 844') for receiving a supply station valve (870; 870').

4. The modular fluid delivery system (4000; 5000) according to Embodiment 2, characterized in that said first inlet pathway (541; 841; 841') comprises a second seat (545; 845; 845') for receiving an air bubble detector (880; 880').

5. The modular fluid delivery system (4000; 5000) according to Embodiment 2, characterized in that said first inlet pathway (541; 841; 841') comprises a third seat (546; 846; 846') for receiving a filtering unit.

6. The modular fluid delivery system (4000; 5000) according to Embodiment 2, characterized in that said second inlet pathway (542; 842; 842') comprises a seat (547; 847; 847') for receiving a first inlet fluid circuit valve.

7. The modular fluid delivery system (4000; 5000) according to Embodiment 2, characterized in that said third inlet pathway (543; 843; 843') comprises a seat (548; 848; 848') for receiving a second inlet fluid circuit valve.

8. The modular fluid delivery system (4000; 5000) according to Embodiment 1, characterized in that said at least one outlet fluid circuit pathway (550; 850; 850') comprises a first outlet pathway (551; 851; 851') and a second outlet pathway (552; 852; 852').

9. The modular fluid delivery system (4000; 5000) according to Embodiment 8, characterized in that said first outlet pathway (551; 851; 851') comprises a seat (555; 855; 855') for receiving a first outlet fluid circuit valve.

10. The modular fluid delivery system (4000; 5000) according to Embodiment 8, characterized in that said second outlet pathway (552; 852; 852') comprises a seat (556; 856; 856') for receiving a second outlet fluid circuit valve.

11. The modular fluid delivery system (4000; 5000) according to Embodiment 2, characterized in that said at least one recirculation fluid circuit pathway (560; 860; 860') is external to said at least one chamber (520; 820; 820') and it fluidically connects said second inlet pathway (542; 842; 842') to said third inlet pathway (543; 843; 843').

12. The modular fluid delivery system (4000; 5000) according to Embodiment 1, characterized in that said at least one recirculation fluid circuit pathway (560; 860; 860') comprises a seat (563; 863; 863') for receiving an actuator (890;

13. The modular fluid delivery system (4000; 5000) according to Embodiment 12, characterized in that said actuator is an electro-mechanical driven valve automatically controlled and operated by a processor (P) of the modular fluid delivery system.

14. The modular fluid delivery system (4000; 5000) according to Embodiment 1, characterized in that said fluid circuit tubing (600; 900) comprises few and short tubing portions that are provided at sensitive locations of the disposable pump module where detection of a fluid specific property should occur or a specific action is requested to be performed onto the fluid flow.

15. The modular fluid delivery system (4000; 5000) according to any of the preceding Embodiments, characterized in that it comprises at least one first disposable pump module assembly (700; 1000; 2000; 3000) for delivering at least one first fluid and at least one second disposable pump module assembly (700; 1000; 2000; 3000) for delivering at least one second fluid, said second fluid being different from said first fluid.

16. The modular fluid delivery system (4000; 5000) according to Embodiment 15, characterized in that said at least one first disposable pump module assembly and said at least one second disposable pump module assembly are arranged in series and are connected to a common driving unit (M).

17. The modular fluid delivery system (4000; 5000) according to Embodiment 15, characterized in that said at least one first disposable pump module assembly and said at least one second disposable pump module assembly are arranged in parallel and are connected to a common driving unit (M).

18. The modular fluid delivery system (4000; 5000) according to Embodiment 15, characterized in that said at least one first disposable pump module assembly and said at least one second disposable pump module assembly are arranged in parallel, and said at least one first pump module assembly is connected to a first driving unit of the modular fluid delivery system while said at least one second pump module assembly is connected to a second driving unit of the modular fluid delivery system.

19. The modular fluid delivery system (4000; 5000) according to Embodiment 1, characterized in that said at least one disposable pump module assembly (1000; 2000; 3000) comprises at least two distinct fluid circuits (X; Y; Z) arranged in series for delivering at least one first fluid and at least one second fluid, said first fluid being different from said second fluid.

20. The modular fluid delivery system (4000; 5000) according to Embodiment 8, characterized in that said first outlet pathway (551; 851; 851') and said second outlet pathway (552; 852; 852') convey into a common outlet pathway (857).

21. The modular fluid delivery system (4000; 5000) according to Embodiment 20, characterized in that said common outlet pathway (857) comprises a seat (858) for receiving an additional air bubble detector (880).

22. The modular fluid delivery system (4000; 5000) according to Embodiment 20, characterized in that said common outlet pathway (857) comprises a seat (859) for receiving at least one pressure sensor.

23. The modular fluid delivery system (4000) according to Embodiment 1, characterized in that it comprises a plurality of slots (4010, 4020, 4030, 4040, 4050), each slot being dedicated to receiving a disposable pump module assembly (700; 1000; 2000; 3000).

24. The modular fluid delivery system according to Embodiment 1, characterized in that it comprises at least two disposable pump module assemblies (700; 1000; 2000; 3000) that are arranged along a circular path that is rotatable and that defines a delivery position in which a selected assembly is positioned for being operated by the modular fluid delivery system.

25. The modular fluid delivery system according to Embodiments 14 and 19, characterized in that said fluid circuits (X; Y; Z) are formed by combining tubing portions of said fluid circuit tubing (600; 900) and portions of said at least one inlet fluid circuit pathway (540; 840; 840'), of said at least one inlet fluid circuit pathway (540; 840; 840') and of said at least one recirculation fluid circuit pathway (560; 860; 860').

The invention claimed is:

1. A modular fluid delivery system (4000; 5000) comprising:

at least one supply station (4060; 4070; 5010; 5020) for supplying at least one fluid, and a pressurizing unit (20; 220) for pressurizing said at least one fluid, said pressurizing unit comprising at least one driving unit (M) and at least one disposable pump module assembly (700; 1000; 2000; 3000), characterized in that said at least one disposable pump module assembly comprises:

at least one disposable pump module (500; 800) which comprises a supporting element (510; 810; 2010) defining:

at least one chamber (520; 820; 820') receiving a piston (525; 825) therein, said piston having a plunger (527; 827; 827') that, in cooperation with internal walls of said chamber, defines first (521; 821; 821') and second (522; 822; 822') variable-volume sub-chambers;

at least one inlet fluid circuit pathway (540; 840; 840') comprising a first inlet pathway (541; 841; 841') which branches into a second inlet pathway (542; 842;

842') and a third inlet pathway (543; 843; 843') that are in fluid communication, respectively, with said first sub-chamber (521; 821; 821') and with said second sub-chamber (522; 822; 822'), wherein said first inlet pathway (541; 841; 841') comprises a first seat (544; 844; 844') for receiving a supply station valve (870;

870'), said second inlet pathway (542; 842; 842') comprises a seat (547; 847;

847') for receiving a first inlet fluid circuit valve, and said third inlet pathway (543; 843; 843') comprises a seat (548; 848; 848') for receiving a second inlet fluid circuit valve;

at least one outlet fluid circuit pathway (550; 850; 850') comprising a first outlet pathway (551; 851; 851') and a second outlet pathway (552; 852; 852'), wherein said first outlet pathway (551; 851; 851') comprises a seat (555; 855; 855') for receiving a first outlet fluid circuit valve and said second outlet pathway (552;

852; 852') comprises a seat (556; 856; 856') for receiving a second outlet fluid circuit valve, and at least one recirculation fluid circuit pathway (560; 860; 860') which comprises a seat (563; 863; 863') for receiving an actuator (890; 890'), said actuator being an active valve and managing the passage of said at least one fluid in both directions between said first and second variable-volume sub-chambers, and a fluid circuit tubing (600; 900) which comprises:

at least one inlet fluid circuit tubing (610; 910; 910') at least partially received within said at least one inlet fluid circuit pathway (540; 840; 840'), said at least one inlet fluid circuit tubing (610; 910; 910') being in fluid communication with said at least one supply station and with said at least one chamber for supplying said at least one fluid to said first and second variable-volume sub-chambers;

at least one outlet fluid circuit tubing (620; 920; 920') at least partially received within said at least one outlet fluid circuit pathway (550; 850; 850'), said at least one outlet fluid circuit tubing (620; 920; 920') being in fluid communication with said at least one chamber for discharging the fluid alternatively from said first and second variable-volume sub-chambers, said outlet fluid circuit tubing being separate from said inlet fluid circuit tubing, and at least one recirculation fluid circuit tubing (630; 930; 930') at least partially received within said at least one recirculation fluid circuit pathway (560; 860; 860'), said at least one recirculation fluid circuit tubing fluidically connecting said first and second variable-volume sub-chambers.

2. The modular fluid delivery system (4000; 5000) according to claim 1, characterized in that said at least one recirculation fluid circuit pathway (560; 860; 860') is external to said at least one chamber (520; 820; 820') and it fluidically connects said second inlet pathway (542; 842; 842') to said third inlet pathway (543; 843; 843').

3. The modular fluid delivery system (4000; 5000) according to claim 1, characterized in that said fluid circuit tubing (600; 900) comprises few and short tubing portions that are provided at sensitive locations of the disposable pump module where detection of a fluid specific property should occur or a specific action is requested to be performed onto the fluid flow.

4. The modular fluid delivery system (4000; 5000) according to claim 3, characterized in that said at least one disposable pump module assembly (1000; 2000; 3000) comprises at least two distinct fluid circuits (X; Y; Z) arranged in series for delivering at least one first fluid and at least one second fluid, said first fluid being different from said second fluid.

5. The modular fluid delivery system according to claim 4, characterized in that said fluid circuits (X; Y; Z) are formed by combining tubing portions of said fluid circuit tubing (600; 900) and portions of said at least one inlet fluid circuit pathway (540; 840; 840'), of said at least one inlet fluid circuit pathway (540; 840; 840') and of said at least one recirculation fluid circuit pathway (560; 860; 860').

6. The modular fluid delivery system (4000; 5000) according to claim 1, characterized in that it comprises at least one first disposable pump module assembly (700; 1000; 2000; 3000) for delivering at least one first fluid and at least one second disposable pump module assembly (700; 1000; 2000; 3000) for delivering at least one second fluid, said second fluid being different from said first fluid.

7. The modular fluid delivery system (4000; 5000) according to claim 1, characterized in that said at least one disposable pump module assembly (1000; 2000; 3000) comprises at least two distinct fluid circuits (X; Y; Z) arranged in series for delivering at least one first fluid and at least one second fluid, said first fluid being different from said second fluid.

8. The modular fluid delivery system (4000) according to claim 1, characterized in that it comprises a plurality of slots (4010, 4020, 4030, 4040, 4050), each slot being dedicated to receiving a disposable pump module assembly (700; 1000; 2000; 3000).

9. The modular fluid delivery system according to claim 1, characterized in that it comprises at least two disposable pump module assemblies (700; 1000; 2000; 3000) that are arranged along a circular path that is rotatable and that defines a delivery position in which a selected assembly is positioned for being operated by the modular fluid delivery system.

* * * * *